(12) United States Patent
Popovich et al.

(10) Patent No.: US 11,662,590 B2
(45) Date of Patent: May 30, 2023

(54) HOLOGRAPHIC WAVEGUIDE EYE TRACKER

(71) Applicant: DigiLens Inc., Sunnyvale, CA (US)

(72) Inventors: Milan Momcilo Popovich, Leicester (GB); Jonathan David Waldern, Los Altos Hills, CA (US); Alastair John Grant, San Jose, CA (US)

(73) Assignee: DigiLens Inc., Sunnyvale, CA (US)

( * ) Notice: Subject to any disclaimer, the term of this patent is extended or adjusted under 35 U.S.C. 154(b) by 0 days.

(21) Appl. No.: 17/646,843

(22) Filed: Jan. 3, 2022

(65) Prior Publication Data

US 2022/0236571 A1 Jul. 28, 2022

Related U.S. Application Data

(63) Continuation of application No. 16/922,858, filed on Jul. 7, 2020, now abandoned, which is a continuation
(Continued)

(51) Int. Cl.
*G02B 27/01* (2006.01)
*A61B 3/113* (2006.01)
(Continued)

(52) U.S. Cl.
CPC .......... *G02B 27/0172* (2013.01); *A61B 3/113* (2013.01); *G02B 6/34* (2013.01);
(Continued)

(58) Field of Classification Search
CPC ...... G02B 2027/014; G02B 2027/0138; G02B 2027/0123; G02B 2027/0118;
(Continued)

(56) References Cited

U.S. PATENT DOCUMENTS 1,043,938 A 11/1912 Huttenlocher
3,482,498 A 12/1969 Becker
(Continued)

FOREIGN PATENT DOCUMENTS

BR PI0720469 A2 1/2014
CA 2889727 A1 6/2014
(Continued)

OTHER PUBLICATIONS

International Search Report and Written Opinion for International Application No. PCT/US2021/034315, Search completed Aug. 13, 2021, dated Sep. 9, 2021, 18 Pgs.
(Continued)

*Primary Examiner* — Ryan A Lepisto
*Assistant Examiner* — Erin D Chiem
(74) *Attorney, Agent, or Firm* — KPPB LLP

(57) ABSTRACT

An eye tracker having a first waveguide for propagating illumination light along a first waveguide path and propagating image light reflected from at least one surface of an eye along a second waveguide path. At least one grating lamina for deflecting the illumination light out of the first waveguide path towards the eye and deflecting the image light into the second waveguide path towards a detector is disposed adjacent an optical surface of the waveguide.

20 Claims, 26 Drawing Sheets

Related U.S. Application Data of application No. 16/277,390, filed on Feb. 15, 2019, now Pat. No. 10,712,571, which is a continuation of application No. 14/903,249, filed as application No. PCT/GB2014/000197 on May 19, 2014, now Pat. No. 10,209,517.

(60) Provisional application No. 61/855,625, filed on May 20, 2013.

(51) Int. Cl.

| | |
|---|---|
| *G02B 6/34* | (2006.01) |
| *G02B 6/42* | (2006.01) |
| *G02F 1/29* | (2006.01) |
| *G02F 1/313* | (2006.01) |
| *G06K 9/62* | (2022.01) |
| *G06V 40/19* | (2022.01) |
| *G02F 1/31* | (2006.01) |
| *A61B 3/10* | (2006.01) |
| *G02B 27/00* | (2006.01) |
| *G06F 18/214* | (2023.01) |

(52) U.S. Cl.
CPC ....... *G02B 6/4206* (2013.01); *G02B 27/0093* (2013.01); *G02B 27/017* (2013.01); *G02F 1/292* (2013.01); *G02F 1/3132* (2013.01); *G06F 18/214* (2023.01); *G06V 40/19* (2022.01); *G02B 2027/014* (2013.01); *G02B 2027/0174* (2013.01); *G02B 2027/0187* (2013.01); *G02F 1/311* (2021.01)

(58) Field of Classification Search
CPC .... G02B 2027/0174; G02B 2027/0178; G02B 27/4272; G02B 27/0101; G02B 27/0174; G02B 27/0093; G02B 27/017; G02B 27/0081; G02B 27/0172; G02B 6/0035; G02B 6/0016; G02B 6/34; G02B 6/00; G02B 5/18; G02B 5/32
See application file for complete search history.

(56) References Cited

U.S. PATENT DOCUMENTS

| | | | |
|---|---|---|---|
| 3,741,716 A | 6/1973 | Johne et al. |
| 3,804,496 A | 4/1974 | Crane et al. |
| 3,843,231 A | 10/1974 | Borel et al. |
| 3,965,029 A | 6/1976 | Arora |
| 3,975,711 A | 8/1976 | McMahon |
| 4,028,725 A | 6/1977 | Lewis |
| 4,035,068 A | 7/1977 | Rawson |
| 4,066,334 A | 1/1978 | Fray et al. |
| 4,133,152 A | 1/1979 | Penrose |
| 4,248,093 A | 2/1981 | Andersson et al. |
| 4,251,137 A | 2/1981 | Knop et al. |
| 4,322,163 A | 3/1982 | Schiller |
| 4,386,361 A | 5/1983 | Simmonds |
| 4,389,612 A | 6/1983 | Simmonds et al. |
| 4,403,189 A | 9/1983 | Simmonds |
| 4,418,993 A | 12/1983 | Lipton |
| 4,472,037 A | 9/1984 | Lipton |
| 4,523,226 A | 6/1985 | Lipton et al. |
| 4,544,267 A | 10/1985 | Schiller |
| 4,562,463 A | 12/1985 | Lipton |
| 4,566,758 A | 1/1986 | Bos et al. |
| 4,583,117 A | 4/1986 | Lipton et al. |
| 4,643,515 A | 2/1987 | Upatnieks |
| 4,688,900 A | 8/1987 | Doane et al. |
| 4,711,512 A | 12/1987 | Upatnieks |
| 4,728,547 A | 3/1988 | Vaz et al. |
| 4,729,640 A | 3/1988 | Sakata et al. |
| 4,765,703 A | 8/1988 | Suzuki et al. |
| 4,791,788 A | 12/1988 | Simmonds et al. |
| 4,792,850 A | 12/1988 | Liptoh et al. |
| 4,811,414 A | 3/1989 | Fishbine et al. |
| 4,848,093 A | 7/1989 | Simmonds et al. |
| 4,852,988 A | 8/1989 | Velez et al. |
| 4,884,876 A | 12/1989 | Lipton et al. |
| 4,890,902 A | 1/1990 | Doane et al. |
| 4,933,976 A | 6/1990 | Fishbine et al. |
| 4,938,568 A | 7/1990 | Margerum et al. |
| 4,960,311 A | 10/1990 | Moss et al. |
| 4,964,701 A | 10/1990 | Dorschner et al. |
| 4,967,268 A | 10/1990 | Lipton et al. |
| 4,970,129 A | 11/1990 | Ingwall et al. |
| 4,971,719 A | 11/1990 | Vaz et al. |
| 4,994,204 A | 2/1991 | Doane et al. |
| 5,004,323 A | 4/1991 | West |
| 5,009,483 A | 4/1991 | Rockwell et al. |
| 5,033,814 A | 7/1991 | Brown et al. |
| 5,053,834 A | 10/1991 | Simmonds |
| 5,063,441 A | 11/1991 | Lipton et al. |
| 5,096,282 A | 3/1992 | Margerum et al. |
| 5,099,343 A | 3/1992 | Margerum et al. |
| 5,110,034 A | 5/1992 | Simmonds et al. |
| 5,117,302 A | 5/1992 | Lipton |
| 5,119,454 A | 6/1992 | McMahon et al. |
| 5,139,192 A | 8/1992 | Simmonds et al. |
| 5,142,357 A | 8/1992 | Lipton et al. |
| 5,142,644 A | 8/1992 | Vansteenkiste et al. |
| 5,148,302 A | 9/1992 | Nagano et al. |
| 5,181,133 A | 1/1993 | Lipton |
| 5,193,000 A | 3/1993 | Lipton et al. |
| 5,198,912 A | 3/1993 | Ingwall et al. |
| 5,200,861 A | 4/1993 | Moskovich et al. |
| 5,218,480 A | 6/1993 | Moskovich et al. |
| 5,224,198 A | 6/1993 | Jachimowicz et al. |
| 5,239,372 A | 8/1993 | Lipton |
| 5,240,636 A | 8/1993 | Doane et al. |
| 5,241,337 A | 8/1993 | Betensky et al. |
| 5,242,476 A | 9/1993 | Bartel et al. |
| 5,251,048 A | 10/1993 | Doane et al. |
| 5,264,950 A | 11/1993 | West et al. |
| 5,268,792 A | 12/1993 | Kreitzer et al. |
| 5,284,499 A | 2/1994 | Harvey et al. |
| 5,295,208 A | 3/1994 | Caulfield et al. |
| 5,296,967 A | 3/1994 | Moskovich et al. |
| 5,299,289 A | 3/1994 | Omae et al. |
| 5,309,283 A | 5/1994 | Kreitzer et al. |
| 5,313,330 A | 5/1994 | Betensky |
| 5,315,324 A | 5/1994 | Kubelik et al. |
| 5,315,419 A | 5/1994 | Saupe et al. |
| 5,315,440 A | 5/1994 | Betensky et al. |
| 5,327,269 A | 7/1994 | Tilton et al. |
| 5,329,363 A | 7/1994 | Moskovich et al. |
| 5,343,147 A | 8/1994 | Sager et al. |
| 5,368,770 A | 11/1994 | Saupe et al. |
| 5,371,626 A | 12/1994 | Betensky |
| 5,410,376 A | 4/1995 | Cornsweet et al. |
| 5,416,510 A | 5/1995 | Lipton et al. |
| 5,418,871 A | 5/1995 | Revelli et al. |
| 5,428,480 A | 6/1995 | Betensky et al. |
| 5,437,811 A | 8/1995 | Doane et al. |
| 5,452,385 A | 9/1995 | Izumi et al. |
| 5,453,863 A | 9/1995 | West et al. |
| 5,455,693 A | 10/1995 | Wreede et al. |
| 5,455,713 A | 10/1995 | Kreitzer et al. |
| 5,463,428 A | 10/1995 | Lipton et al. |
| 5,465,311 A | 11/1995 | Caulfield et al. |
| 5,476,611 A | 12/1995 | Nolan et al. |
| 5,481,321 A | 1/1996 | Lipton |
| 5,485,313 A | 1/1996 | Betensky |
| 5,493,430 A | 2/1996 | Lu et al. |
| 5,493,448 A | 2/1996 | Betensky et al. |
| 5,499,140 A | 3/1996 | Betensky |
| 5,500,769 A | 3/1996 | Betensky |
| 5,515,184 A | 5/1996 | Caulfield et al. |
| 5,516,455 A | 5/1996 | Jacobine et al. |
| 5,530,566 A | 6/1996 | Kumar |
| 5,532,875 A | 7/1996 | Betemsky |
| RE35,310 E | 8/1996 | Moskovich |
| 5,543,950 A | 8/1996 | Lavrentovich et al. |

(56) References Cited

U.S. PATENT DOCUMENTS

| | | |
|---|---|---|
| 5,559,637 A | 9/1996 | Moskovich et al. |
| 5,572,250 A | 11/1996 | Lipton et al. |
| 5,576,888 A | 11/1996 | Betensky |
| 5,585,035 A | 12/1996 | Nerad et al. |
| 5,593,615 A | 1/1997 | Nerad et al. |
| 5,619,586 A | 4/1997 | Sibbald et al. |
| 5,621,529 A | 4/1997 | Gordon et al. |
| 5,621,552 A | 4/1997 | Coates et al. |
| 5,625,495 A | 4/1997 | Moskovich et al. |
| 5,668,614 A | 9/1997 | Chien et al. |
| 5,677,797 A | 10/1997 | Betensky et al. |
| 5,680,231 A | 10/1997 | Grinberg et al. |
| 5,682,255 A | 10/1997 | Friesem et al. |
| 5,686,931 A | 11/1997 | Fuenfschilling et al. |
| 5,686,975 A | 11/1997 | Lipton |
| 5,691,795 A | 11/1997 | Doane et al. |
| 5,695,682 A | 12/1997 | Doane et al. |
| 5,706,136 A | 1/1998 | Okuyama et al. |
| 5,710,645 A | 1/1998 | Phillips et al. |
| 5,745,266 A | 4/1998 | Smith et al. |
| 5,745,301 A | 4/1998 | Betensky et al. |
| 5,748,272 A | 5/1998 | Tanaka et al. |
| 5,748,277 A | 5/1998 | Huang et al. |
| 5,751,452 A | 5/1998 | Tanaka et al. |
| 5,757,546 A | 5/1998 | Lipton et al. |
| 5,790,314 A | 8/1998 | Duck et al. |
| 5,798,641 A | 8/1998 | Spagna et al. |
| 5,808,804 A | 9/1998 | Moskovich |
| 5,822,089 A | 10/1998 | Phillips et al. |
| 5,825,448 A | 10/1998 | Bos et al. |
| 5,831,700 A | 11/1998 | Li et al. |
| 5,835,661 A | 11/1998 | Tai et al. |
| 5,841,587 A | 11/1998 | Moskovich et al. |
| 5,856,842 A | 1/1999 | Tedesco |
| 5,867,238 A | 2/1999 | Miller et al. |
| 5,870,228 A | 2/1999 | Kreitzer et al. |
| 5,875,012 A | 2/1999 | Crawford et al. |
| 5,877,826 A | 3/1999 | Yang et al. |
| 5,892,599 A | 4/1999 | Bahuguna |
| 5,900,987 A | 5/1999 | Kreitzer et al. |
| 5,900,989 A | 5/1999 | Kreitzer |
| 5,929,960 A | 7/1999 | West et al. |
| 5,930,433 A | 7/1999 | Williamson et al. |
| 5,936,776 A | 8/1999 | Kreitzer |
| 5,937,115 A | 8/1999 | Domash |
| 5,942,157 A | 8/1999 | Sutherland et al. |
| 5,949,508 A | 9/1999 | Kumar et al. |
| 5,956,113 A | 9/1999 | Crawford |
| 5,963,375 A | 10/1999 | Kreitzer |
| 5,966,223 A | 10/1999 | Friesem et al. |
| 5,969,874 A | 10/1999 | Moskovich |
| 5,969,876 A | 10/1999 | Kreitzer et al. |
| 5,973,727 A | 10/1999 | McGrew et al. |
| 5,974,162 A | 10/1999 | Metz et al. |
| 5,986,746 A | 11/1999 | Metz et al. |
| 5,999,089 A | 12/1999 | Carlson et al. |
| 5,999,282 A | 12/1999 | Suzuki et al. |
| 6,014,187 A | 1/2000 | Taketomi et al. |
| 6,023,375 A | 2/2000 | Kreitzer |
| 6,046,585 A | 4/2000 | Simmonds |
| 6,052,540 A | 4/2000 | Koyama |
| 6,061,107 A | 5/2000 | Yang |
| 6,061,463 A | 5/2000 | Metz et al. |
| 6,069,728 A | 5/2000 | Huignard et al. |
| 6,094,311 A | 7/2000 | Moskovich |
| 6,097,551 A | 8/2000 | Kreitzer |
| 6,104,448 A | 8/2000 | Doane et al. |
| 6,115,152 A | 9/2000 | Popovich et al. |
| 6,124,954 A | 9/2000 | Popovich et al. |
| 6,128,058 A | 10/2000 | Walton et al. |
| 6,133,971 A | 10/2000 | Silverstein et al. |
| 6,133,975 A | 10/2000 | Li et al. |
| 6,141,074 A | 10/2000 | Bos et al. |
| 6,141,154 A | 10/2000 | Kreitzer et al. |
| 6,151,142 A | 11/2000 | Phillips et al. |
| 6,154,190 A | 11/2000 | Yang et al. |
| 6,169,594 B1 | 1/2001 | Aye et al. |
| 6,169,613 B1 | 1/2001 | Amitai et al. |
| 6,169,636 B1 | 1/2001 | Kreitzer et al. |
| 6,188,462 B1 | 2/2001 | Lavrentovich et al. |
| 6,191,887 B1 | 2/2001 | Michaloski et al. |
| 6,195,209 B1 | 2/2001 | Kreitzer et al. |
| 6,204,835 B1 | 3/2001 | Yang et al. |
| 6,211,976 B1 | 4/2001 | Popovich et al. |
| 6,268,839 B1 | 7/2001 | Yang et al. |
| 6,269,203 B1 | 7/2001 | Davies et al. |
| 6,275,031 B1 | 8/2001 | Simmonds et al. |
| 6,278,429 B1 | 8/2001 | Ruth et al. |
| 6,297,860 B1 | 10/2001 | Moskovich et al. |
| 6,301,056 B1 | 10/2001 | Kreitzer et al. |
| 6,301,057 B1 | 10/2001 | Kreitzer et al. |
| 6,317,228 B2 | 11/2001 | Popovich et al. |
| 6,320,563 B1 | 11/2001 | Yang et al. |
| 6,324,014 B1 | 11/2001 | Moskovich et al. |
| 6,330,109 B1 | 12/2001 | Ishii et al. |
| 6,351,273 B1 | 2/2002 | Lemelson et al. |
| 6,366,281 B1 | 4/2002 | Lipton et al. |
| 6,377,238 B1 | 4/2002 | McPheters |
| 6,377,321 B1 | 4/2002 | Khan et al. |
| 6,388,797 B1 | 5/2002 | Lipton et al. |
| 6,411,444 B1 | 6/2002 | Moskovich et al. |
| 6,414,760 B1 | 7/2002 | Lopez et al. |
| 6,417,971 B1 | 7/2002 | Moskovich et al. |
| 6,437,563 B1 | 8/2002 | Simmonds et al. |
| 6,445,512 B1 | 9/2002 | Moskovich et al. |
| 6,476,974 B1 | 11/2002 | Kreitzer et al. |
| 6,483,303 B2 | 11/2002 | Simmonds et al. |
| 6,504,629 B1 | 1/2003 | Popovich et al. |
| 6,509,937 B1 | 1/2003 | Moskovich et al. |
| 6,518,747 B2 | 2/2003 | Sager et al. |
| 6,519,088 B1 | 2/2003 | Lipton |
| 6,529,336 B1 | 3/2003 | Kreitzer et al. |
| 6,559,813 B1 | 5/2003 | DeLuca et al. |
| 6,563,648 B2 | 5/2003 | Gleckman et al. |
| 6,563,650 B2 | 5/2003 | Moskovich et al. |
| 6,567,573 B1 | 5/2003 | Domash et al. |
| 6,577,411 B1 | 6/2003 | David et al. |
| 6,577,429 B1 | 6/2003 | Kurtz et al. |
| 6,580,529 B1 | 6/2003 | Amitai et al. |
| 6,583,838 B1 | 6/2003 | Hoke et al. |
| 6,594,090 B2 | 7/2003 | Kruschwitz et al. |
| 6,597,176 B2 | 7/2003 | Simmonds et al. |
| 6,597,475 B1 | 7/2003 | Shirakura et al. |
| 6,600,590 B2 | 7/2003 | Roddy et al. |
| 6,618,104 B1 | 9/2003 | Date et al. |
| 6,625,381 B2 | 9/2003 | Roddy et al. |
| 6,646,772 B1 | 11/2003 | Popovich et al. |
| 6,667,134 B1 | 12/2003 | Sutherland et al. |
| 6,677,086 B1 | 1/2004 | Sutehrland et al. |
| 6,692,666 B2 | 2/2004 | Sutherland et al. |
| 6,699,407 B1 | 3/2004 | Sutehrland et al. |
| 6,706,086 B2 | 3/2004 | Emig et al. |
| 6,706,451 B1 | 3/2004 | Sutherland et al. |
| 6,730,442 B1 | 5/2004 | Sutherland et al. |
| 6,731,434 B1 | 5/2004 | Hua et al. |
| 6,738,105 B1 | 5/2004 | Hannah et al. |
| 6,747,781 B2 | 6/2004 | Trisnadi et al. |
| 6,791,629 B2 | 9/2004 | Moskovich et al. |
| 6,791,739 B2 | 9/2004 | Ramanujan et al. |
| 6,804,066 B1 | 10/2004 | Ha et al. |
| 6,805,490 B2 | 10/2004 | Levola |
| 6,821,457 B1 | 11/2004 | Natarajan et al. |
| 6,822,713 B1 | 11/2004 | Yaroshchuk et al. |
| 6,825,987 B2 | 11/2004 | Repetto et al. |
| 6,829,095 B2 | 12/2004 | Amitai |
| 6,830,789 B2 | 12/2004 | Doane et al. |
| 6,833,955 B2 | 12/2004 | Niv |
| 6,847,488 B2 | 1/2005 | Travis |
| 6,850,210 B1 | 2/2005 | Lipton et al. |
| 6,853,493 B2 | 2/2005 | Kreitzer et al. |
| 6,867,888 B2 | 3/2005 | Sutherland et al. |
| 6,878,494 B2 | 4/2005 | Sutehrland et al. |
| 6,927,570 B2 | 8/2005 | Simmonds et al. |
| 6,927,694 B1 | 8/2005 | Smith et al. |

(56) References Cited

U.S. PATENT DOCUMENTS

| | | |
|---|---|---|
| 6,950,173 B1 | 9/2005 | Sutherland et al. |
| 6,952,435 B2 | 10/2005 | Lai et al. |
| 6,958,868 B1 | 10/2005 | Pender |
| 6,963,454 B1 | 11/2005 | Martins et al. |
| 6,975,345 B1 | 12/2005 | Lipton et al. |
| 6,980,365 B2 | 12/2005 | Moskovich |
| 6,985,296 B2 | 1/2006 | Lipton et al. |
| 6,999,239 B1 | 2/2006 | Martins et al. |
| 7,002,618 B2 | 2/2006 | Lipton et al. |
| 7,002,753 B2 | 2/2006 | Moskovich et al. |
| 7,009,773 B2 | 3/2006 | Chaoulov et al. |
| 7,018,563 B1 | 3/2006 | Sutherland et al. |
| 7,018,686 B2 | 3/2006 | Sutehrland et al. |
| 7,019,793 B2 | 3/2006 | Moskovich et al. |
| 7,021,777 B2 | 4/2006 | Amitai |
| 7,026,892 B2 | 4/2006 | Kajiya |
| 7,054,045 B2 | 5/2006 | McPheters et al. |
| 7,068,405 B2 | 6/2006 | Sutherland et al. |
| 7,072,020 B1 | 7/2006 | Sutherland et al. |
| 7,075,273 B2 | 7/2006 | O'Gorman et al. |
| 7,077,984 B1 | 7/2006 | Natarajan et al. |
| 7,081,215 B2 | 7/2006 | Natarajan et al. |
| 7,088,457 B1 | 8/2006 | Zou et al. |
| 7,088,515 B2 | 8/2006 | Lipton |
| 7,099,080 B2 | 8/2006 | Lipton et al. |
| 7,108,383 B1 | 9/2006 | Mitchell et al. |
| 7,119,965 B1 | 10/2006 | Rolland et al. |
| 7,123,421 B1 | 10/2006 | Moskovich et al. |
| 7,133,084 B2 | 11/2006 | Moskovich et al. |
| 7,139,109 B2 | 11/2006 | Mukawa |
| RE39,424 E | 12/2006 | Moskovich |
| 7,145,729 B2 | 12/2006 | Kreitzer et al. |
| 7,149,385 B2 | 12/2006 | Parikka et al. |
| 7,167,286 B2 | 1/2007 | Anderson et al. |
| 7,175,780 B1 | 2/2007 | Sutherland et al. |
| 7,181,108 B2 | 2/2007 | Levola |
| 7,184,002 B2 | 2/2007 | Lipton et al. |
| 7,184,615 B2 | 2/2007 | Levola |
| 7,186,567 B1 | 3/2007 | Sutherland et al. |
| 7,198,737 B2 | 4/2007 | Natarajan et al. |
| 7,206,107 B2 | 4/2007 | Levola |
| 7,230,770 B2 | 6/2007 | Kreitzer et al. |
| 7,256,915 B2 | 8/2007 | Sutherland et al. |
| 7,265,882 B2 | 9/2007 | Sutherland et al. |
| 7,265,903 B2 | 9/2007 | Sutherland et al. |
| RE39,911 E | 11/2007 | Moskovich |
| 7,301,601 B2 | 11/2007 | Lin et al. |
| 7,312,906 B2 | 12/2007 | Sutherland et al. |
| 7,333,685 B2 | 2/2008 | Stone et al. |
| 7,375,886 B2 | 5/2008 | Lipton et al. |
| 7,391,573 B2 | 6/2008 | Amitai |
| 7,413,678 B1 | 8/2008 | Natarajan et al. |
| 7,413,679 B1 | 8/2008 | Sutherland et al. |
| 7,416,818 B2 | 8/2008 | Sutherland et al. |
| 7,418,170 B2 | 8/2008 | Mukawa et al. |
| 7,420,733 B1 | 9/2008 | Natarajan et al. |
| 7,453,612 B2 | 11/2008 | Mukawa |
| 7,454,103 B2 | 11/2008 | Parriaux |
| 7,457,040 B2 | 11/2008 | Amitai |
| 7,477,206 B2 | 1/2009 | Cowan et al. |
| 7,499,217 B2 | 3/2009 | Cakmakci et al. |
| 7,511,891 B2 | 3/2009 | Messerschmidt |
| 7,522,344 B1 | 4/2009 | Curatu et al. |
| 7,542,210 B2 | 6/2009 | Chirieleison |
| 7,570,322 B1 | 8/2009 | Sutherland et al. |
| 7,570,405 B1 | 8/2009 | Sutherland et al. |
| 7,577,326 B2 | 8/2009 | Amitai |
| 7,583,423 B2 | 9/2009 | Sutherland et al. |
| 7,589,901 B2 | 9/2009 | DeJong et al. |
| 7,605,882 B1 | 10/2009 | Sutherland et al. |
| 7,619,739 B1 | 11/2009 | Sutherland et al. |
| 7,639,208 B1 | 12/2009 | Ha et al. |
| 7,643,214 B2 | 1/2010 | Amitai |
| 7,672,055 B2 | 3/2010 | Amitai |
| 7,672,549 B2 | 3/2010 | Ghosh et al. |
| 7,710,622 B2 | 5/2010 | Takabayashi et al. |
| 7,724,443 B2 | 5/2010 | Amitai |
| 7,740,387 B2 | 6/2010 | Schultz et al. |
| 7,747,113 B2 | 6/2010 | Mukawa et al. |
| 7,751,122 B2 | 7/2010 | Amitai |
| 7,751,662 B2 | 7/2010 | Kleemann et al. |
| 7,764,413 B2 | 7/2010 | Levola |
| 7,777,819 B2 | 8/2010 | Simmonds |
| 7,843,642 B2 | 11/2010 | Shaoulov et al. |
| 7,866,869 B2 | 1/2011 | Karakawa |
| 7,872,707 B1 | 1/2011 | Sutherland et al. |
| 7,884,593 B2 | 2/2011 | Simmonds et al. |
| 7,884,985 B2 | 2/2011 | Amitai et al. |
| 7,907,342 B2 | 3/2011 | Simmonds et al. |
| 7,936,519 B2 | 5/2011 | Mukawa et al. |
| 7,944,616 B2 | 5/2011 | Mukawa |
| 7,949,214 B2 | 5/2011 | DeJong et al. |
| 7,969,657 B2 | 6/2011 | Cakmakci et al. |
| 8,000,020 B2 | 8/2011 | Amitai et al. |
| 8,014,050 B2 | 9/2011 | McGrew |
| 8,016,475 B2 | 9/2011 | Travis |
| 8,018,579 B1 | 9/2011 | Krah |
| 8,023,783 B2 | 9/2011 | Mukawa et al. |
| 8,073,296 B2 | 12/2011 | Mukawa et al. |
| 8,077,274 B2 | 12/2011 | Sutherland et al. |
| 8,093,451 B2 | 1/2012 | Spangenberg et al. |
| 8,098,439 B2 | 1/2012 | Amitai et al. |
| 8,107,023 B2 | 1/2012 | Simmonds et al. |
| 8,107,780 B2 | 1/2012 | Simmonds |
| 8,132,948 B2 | 3/2012 | Owen et al. |
| 8,134,434 B2 | 3/2012 | Diederichs et al. |
| 8,142,016 B2 | 3/2012 | Legerton et al. |
| 8,155,489 B2 | 4/2012 | Saarikko et al. |
| 8,160,411 B2 | 4/2012 | Levola et al. |
| 8,167,173 B1 | 5/2012 | Simmonds et al. |
| 8,194,325 B2 | 6/2012 | Levola et al. |
| 8,213,065 B2 | 7/2012 | Mukawa |
| 8,213,755 B2 | 7/2012 | Mukawa et al. |
| 8,220,966 B2 | 7/2012 | Mukawa |
| 8,224,133 B2 | 7/2012 | Popovich et al. |
| 8,233,204 B1 | 7/2012 | Robbins et al. |
| 8,294,749 B2 | 10/2012 | Cable |
| 8,310,327 B2 | 11/2012 | Willers et al. |
| 8,314,993 B2 | 11/2012 | Levola et al. |
| 8,320,032 B2 | 11/2012 | Levola |
| 8,325,166 B2 | 12/2012 | Akutsu et al. |
| 8,329,773 B2 | 12/2012 | Fäcke et al. |
| 8,335,040 B2 | 12/2012 | Mukawa et al. |
| 8,351,744 B2 | 1/2013 | Travis et al. |
| 8,354,640 B2 | 1/2013 | Hamre et al. |
| 8,355,610 B2 | 1/2013 | Simmonds |
| 8,369,019 B2 | 2/2013 | Baker et al. |
| 8,376,548 B2 | 2/2013 | Schultz |
| 8,382,293 B2 | 2/2013 | Phillips, III et al. |
| 8,384,504 B2 | 2/2013 | Diederichs et al. |
| 8,396,339 B2 | 3/2013 | Mukawa et al. |
| 8,422,840 B2 | 4/2013 | Large |
| 8,432,614 B2 | 4/2013 | Amitai |
| 8,441,731 B2 | 5/2013 | Sprague |
| 8,466,953 B2 | 6/2013 | Levola |
| 8,472,120 B2 | 6/2013 | Border et al. |
| 8,481,130 B2 | 7/2013 | Harding et al. |
| 8,482,858 B2 | 7/2013 | Sprague |
| 8,488,246 B2 | 7/2013 | Border et al. |
| 8,491,136 B2 | 7/2013 | Travis et al. |
| 8,493,662 B2 | 7/2013 | Noui |
| 8,494,229 B2 | 7/2013 | Jarvenpaa et al. |
| 8,520,309 B2 | 8/2013 | Sprague |
| 8,547,638 B2 | 10/2013 | Levola |
| 8,548,290 B2 | 10/2013 | Travers et al. |
| 8,565,560 B2 | 10/2013 | Popovich et al. |
| 8,582,206 B2 | 11/2013 | Travis |
| 8,593,734 B2 | 11/2013 | Laakkonen |
| 8,611,014 B2 | 12/2013 | Valera et al. |
| 8,634,120 B2 | 1/2014 | Popovich et al. |
| 8,639,072 B2 | 1/2014 | Popovich et al. |
| 8,643,948 B2 | 2/2014 | Amitai et al. |
| 8,649,099 B2 | 2/2014 | Schultz et al. |
| 8,654,420 B2 | 2/2014 | Simmonds |

(56) References Cited

U.S. PATENT DOCUMENTS

| | | |
|---|---|---|
| 8,659,826 B1 | 2/2014 | Brown et al. |
| D701,206 S | 3/2014 | Luckey et al. |
| 8,698,705 B2 | 4/2014 | Burke |
| 8,731,350 B1 | 5/2014 | Lin et al. |
| 8,736,963 B2 | 5/2014 | Robbins et al. |
| 8,746,008 B1 | 6/2014 | Mauritsen et al. |
| 8,786,923 B2 | 7/2014 | Chuang et al. |
| 8,810,913 B2 | 8/2014 | Simmonds et al. |
| 8,810,914 B2 | 8/2014 | Amitai |
| 8,817,350 B1 | 8/2014 | Robbins et al. |
| 8,824,836 B2 | 9/2014 | Sugiyama |
| 8,830,584 B2 | 9/2014 | Saarikko et al. |
| 8,842,368 B2 | 9/2014 | Simmonds et al. |
| 8,859,412 B2 | 10/2014 | Jain |
| 8,872,435 B2 | 10/2014 | Kreitzer et al. |
| 8,873,149 B2 | 10/2014 | Bohn et al. |
| 8,873,150 B2 | 10/2014 | Amitai |
| 8,885,997 B2 | 11/2014 | Nguyen et al. |
| 8,903,207 B1 | 12/2014 | Brown et al. |
| 8,906,088 B2 | 12/2014 | Pugh et al. |
| 8,913,865 B1 | 12/2014 | Bennett |
| 8,917,453 B2 | 12/2014 | Bohn |
| 8,929,589 B2 | 1/2015 | Publicover et al. |
| 8,937,771 B2 | 1/2015 | Robbins et al. |
| 8,950,867 B2 | 2/2015 | Macnamara |
| 8,964,298 B2 | 2/2015 | Haddick et al. |
| 8,965,152 B2 | 2/2015 | Simmonds |
| 8,985,803 B2 | 3/2015 | Bohn |
| 8,989,535 B2 | 3/2015 | Robbins |
| 9,019,595 B2 | 4/2015 | Jain |
| 9,025,253 B2 | 5/2015 | Hadad et al. |
| 9,035,344 B2 | 5/2015 | Jain |
| 9,075,184 B2 | 7/2015 | Popovich et al. |
| 9,081,178 B2 | 7/2015 | Simmonds et al. |
| 9,128,226 B2 | 9/2015 | Fattal et al. |
| 9,129,295 B2 | 9/2015 | Border et al. |
| 9,164,290 B2 | 10/2015 | Robbins et al. |
| 9,201,270 B2 | 12/2015 | Fattal et al. |
| 9,215,293 B2 | 12/2015 | Miller |
| 9,269,854 B2 | 2/2016 | Jain |
| 9,274,338 B2 | 3/2016 | Robbins et al. |
| 9,310,566 B2 | 4/2016 | Valera et al. |
| 9,329,325 B2 | 5/2016 | Simmonds et al. |
| 9,335,548 B1 | 5/2016 | Cakmakci et al. |
| 9,341,846 B2 | 5/2016 | Popovich et al. |
| 9,354,366 B2 | 5/2016 | Jain |
| 9,366,862 B2 | 6/2016 | Haddick et al. |
| 9,372,347 B1 | 6/2016 | Levola et al. |
| 9,377,623 B2 | 6/2016 | Robbins et al. |
| 9,389,415 B2 | 7/2016 | Fattal et al. |
| 9,400,395 B2 | 7/2016 | Travers et al. |
| 9,423,360 B1 | 8/2016 | Kostamo et al. |
| 9,429,692 B1 | 8/2016 | Saarikko et al. |
| 9,431,794 B2 | 8/2016 | Jain |
| 9,456,744 B2 | 10/2016 | Popovich et al. |
| 9,459,451 B2 | 10/2016 | Saarikko et al. |
| 9,465,213 B2 | 10/2016 | Simmonds |
| 9,494,799 B2 | 11/2016 | Robbins et al. |
| 9,513,480 B2 | 12/2016 | Saarikko et al. |
| 9,535,253 B2 | 1/2017 | Levola et al. |
| 9,541,383 B2 | 1/2017 | Abovitz et al. |
| 9,547,174 B2 | 1/2017 | Gao et al. |
| 9,551,874 B2 | 1/2017 | Amitai |
| 9,551,880 B2 | 1/2017 | Amitai |
| 9,612,403 B2 | 4/2017 | Abovitz et al. |
| 9,651,368 B2 | 5/2017 | Abovitz et al. |
| 9,664,824 B2 | 5/2017 | Simmonds et al. |
| 9,664,910 B2 | 5/2017 | Mansharof et al. |
| 9,727,772 B2 | 8/2017 | Popovich et al. |
| 9,746,688 B2 | 8/2017 | Popovich et al. |
| 9,804,389 B2 | 10/2017 | Popovich et al. |
| 10,209,517 B2 | 2/2019 | Popovich et al. |
| 10,234,696 B2 | 3/2019 | Popovich et al. |
| 10,241,330 B2 | 3/2019 | Popovich et al. |
| 10,330,777 B2 | 6/2019 | Popovich et al. |
| 10,423,222 B2 | 9/2019 | Popovich et al. |
| 10,437,051 B2 | 10/2019 | Popovich et al. |
| 10,437,064 B2 | 10/2019 | Popovich et al. |
| 10,569,449 B1 | 2/2020 | Curts et al. |
| 10,578,876 B1 | 3/2020 | Lam et al. |
| 10,598,938 B1 | 3/2020 | Huang et al. |
| 10,613,268 B1 | 4/2020 | Colburn et al. |
| 10,649,119 B2 | 5/2020 | Mohanty et al. |
| 10,690,831 B2 | 6/2020 | Calafiore |
| 10,712,571 B2 | 7/2020 | Popovich et al. |
| 10,732,266 B2 | 8/2020 | Popovich et al. |
| 10,732,351 B2 | 8/2020 | Colburn et al. |
| 10,823,887 B1 | 11/2020 | Calafiore et al. |
| 10,983,257 B1 | 4/2021 | Colburn et al. |
| 10,983,340 B2 | 4/2021 | Popovich et al. |
| 11,009,699 B2 | 5/2021 | Popovich et al. |
| 11,103,892 B1 | 8/2021 | Liao et al. |
| 11,107,972 B2 | 8/2021 | Diest et al. |
| 11,137,603 B2 | 10/2021 | Zhang |
| 11,194,159 B2 | 12/2021 | Popovich et al. |
| 11,243,333 B2 | 2/2022 | Ouderkirk et al. |
| 11,306,193 B1 | 4/2022 | Lane et al. |
| 11,307,357 B2 | 4/2022 | Mohanty |
| 11,340,386 B1 | 5/2022 | Ouderkirk et al. |
| 11,391,950 B2 | 7/2022 | Calafiore |
| 11,442,151 B2 | 9/2022 | Popovich et al. |
| 11,480,788 B2 | 10/2022 | Popovich et al. |
| 2001/0043163 A1 | 11/2001 | Waldern et al. |
| 2001/0050756 A1 | 12/2001 | Lipton et al. |
| 2002/0003509 A1 | 1/2002 | Lipton et al. |
| 2002/0009299 A1 | 1/2002 | Lipton |
| 2002/0011969 A1 | 1/2002 | Lipton et al. |
| 2002/0036825 A1 | 3/2002 | Lipton et al. |
| 2002/0047837 A1 | 4/2002 | Suyama et al. |
| 2002/0075240 A1 | 6/2002 | Lieberman et al. |
| 2002/0110077 A1 | 8/2002 | Drobot et al. |
| 2002/0126332 A1 | 9/2002 | Popovich |
| 2002/0167462 A1 | 11/2002 | Lewis et al. |
| 2002/0196332 A1 | 12/2002 | Lipton et al. |
| 2003/0007070 A1 | 1/2003 | Lipton et al. |
| 2003/0038912 A1 | 2/2003 | Broer et al. |
| 2003/0067685 A1 | 4/2003 | Niv |
| 2003/0086670 A1 | 5/2003 | Moridaira et al. |
| 2003/0107809 A1 | 6/2003 | Chen et al. |
| 2003/0184868 A1 | 10/2003 | Geist |
| 2003/0197157 A1 | 10/2003 | Sutherland et al. |
| 2003/0202247 A1 | 10/2003 | Niv et al. |
| 2004/0004767 A1 | 1/2004 | Song |
| 2004/0089842 A1 | 5/2004 | Sutehrland et al. |
| 2004/0108971 A1 | 6/2004 | Waldern et al. |
| 2004/0109234 A1 | 6/2004 | Levola |
| 2004/0112862 A1 | 6/2004 | Willson et al. |
| 2004/0141217 A1 | 7/2004 | Endo et al. |
| 2004/0175627 A1 | 9/2004 | Sutherland et al. |
| 2004/0179764 A1 | 9/2004 | Melikechi et al. |
| 2004/0263969 A1 | 12/2004 | Lipton et al. |
| 2004/0263971 A1 | 12/2004 | Lipton et al. |
| 2005/0018304 A1 | 1/2005 | Lipton et al. |
| 2005/0079663 A1 | 4/2005 | Masutani et al. |
| 2005/0105909 A1 | 5/2005 | Stone |
| 2005/0122395 A1 | 6/2005 | Lipton et al. |
| 2005/0134404 A1 | 6/2005 | Kajiya et al. |
| 2005/0141066 A1 | 6/2005 | Ouchi |
| 2005/0180687 A1 | 8/2005 | Amitai |
| 2005/0195276 A1 | 9/2005 | Lipton et al. |
| 2005/0232530 A1 | 10/2005 | Kekas |
| 2005/0265585 A1 | 12/2005 | Rowe |
| 2005/0271258 A1 | 12/2005 | Rowe |
| 2005/0286133 A1 | 12/2005 | Lipton |
| 2006/0012878 A1 | 1/2006 | Lipton et al. |
| 2006/0043938 A1 | 3/2006 | O'Gorman et al. |
| 2006/0119837 A1 | 6/2006 | Raguin et al. |
| 2006/0132914 A1 | 6/2006 | Weiss et al. |
| 2006/0146422 A1 | 7/2006 | Koike |
| 2006/0171647 A1 | 8/2006 | Ye et al. |
| 2006/0191293 A1 | 8/2006 | Kuczma |
| 2006/0215244 A1 | 9/2006 | Yosha et al. |
| 2006/0221063 A1 | 10/2006 | Ishihara |
| 2006/0228073 A1 | 10/2006 | Mukawa et al. |

(56) References Cited

U.S. PATENT DOCUMENTS

| | | |
|---|---|---|
| 2006/0268104 A1 | 11/2006 | Cowan et al. |
| 2006/0268412 A1 | 11/2006 | Downing et al. |
| 2006/0284974 A1 | 12/2006 | Lipton et al. |
| 2006/0285205 A1 | 12/2006 | Lipton et al. |
| 2006/0291052 A1 | 12/2006 | Lipton et al. |
| 2007/0012777 A1 | 1/2007 | Tsikos et al. |
| 2007/0019152 A1 | 1/2007 | Caputo et al. |
| 2007/0041684 A1 | 2/2007 | Popovich et al. |
| 2007/0070476 A1 | 3/2007 | Yamada et al. |
| 2007/0070504 A1 | 3/2007 | Akutsu et al. |
| 2007/0097502 A1 | 5/2007 | Lipton et al. |
| 2007/0109401 A1 | 5/2007 | Lipton et al. |
| 2007/0133089 A1 | 6/2007 | Lipton et al. |
| 2007/0154153 A1 | 7/2007 | Fomitchov et al. |
| 2007/0160325 A1 | 7/2007 | Son et al. |
| 2007/0177007 A1 | 8/2007 | Lipton et al. |
| 2007/0183650 A1 | 8/2007 | Lipton et al. |
| 2007/0188602 A1 | 8/2007 | Cowan et al. |
| 2007/0206155 A1 | 9/2007 | Lipton |
| 2007/0236560 A1 | 10/2007 | Lipton et al. |
| 2007/0237456 A1 | 10/2007 | Blauvelt et al. |
| 2007/0247687 A1 | 10/2007 | Handschy et al. |
| 2007/0258138 A1 | 11/2007 | Cowan et al. |
| 2007/0263169 A1 | 11/2007 | Lipton |
| 2008/0018851 A1 | 1/2008 | Lipton et al. |
| 2008/0024598 A1 | 1/2008 | Perlin et al. |
| 2008/0043334 A1 | 2/2008 | Itzkovitch et al. |
| 2008/0049100 A1 | 2/2008 | Lipton et al. |
| 2008/0062259 A1 | 3/2008 | Lipton et al. |
| 2008/0106775 A1 | 5/2008 | Amitai et al. |
| 2008/0106779 A1 | 5/2008 | Peterson et al. |
| 2008/0117289 A1 | 5/2008 | Schowengerdt et al. |
| 2008/0138013 A1 | 6/2008 | Parriaux |
| 2008/0143964 A1 | 6/2008 | Cowan et al. |
| 2008/0143965 A1 | 6/2008 | Cowan et al. |
| 2008/0149517 A1 | 6/2008 | Lipton et al. |
| 2008/0151370 A1 | 6/2008 | Cook et al. |
| 2008/0186573 A1 | 8/2008 | Lipton |
| 2008/0186574 A1 | 8/2008 | Robinson et al. |
| 2008/0198471 A1 | 8/2008 | Amitai |
| 2008/0226281 A1 | 9/2008 | Lipton |
| 2008/0239067 A1 | 10/2008 | Lipton |
| 2008/0239068 A1 | 10/2008 | Lipton |
| 2008/0251772 A1 | 10/2008 | Rohlfing et al. |
| 2008/0273081 A1 | 11/2008 | Lipton |
| 2008/0285137 A1 | 11/2008 | Simmonds et al. |
| 2008/0297731 A1 | 12/2008 | Powell et al. |
| 2008/0298649 A1 | 12/2008 | Ennis et al. |
| 2008/0303895 A1 | 12/2008 | Akka et al. |
| 2008/0303896 A1 | 12/2008 | Lipton et al. |
| 2008/0304111 A1 | 12/2008 | Queenan et al. |
| 2008/0316303 A1 | 12/2008 | Chiu et al. |
| 2008/0316375 A1 | 12/2008 | Lipton et al. |
| 2009/0052047 A1 | 2/2009 | Amitai |
| 2009/0074356 A1 | 3/2009 | Sanchez et al. |
| 2009/0128495 A1 | 5/2009 | Kong et al. |
| 2009/0128911 A1 | 5/2009 | Itzkovitch et al. |
| 2009/0141324 A1 | 6/2009 | Mukawa |
| 2009/0190222 A1 | 7/2009 | Simmonds et al. |
| 2009/0242021 A1 | 10/2009 | Petkie et al. |
| 2009/0296218 A1 | 12/2009 | Ryytty |
| 2009/0303599 A1 | 12/2009 | Levola |
| 2010/0014312 A1 | 1/2010 | Travis et al. |
| 2010/0039796 A1 | 2/2010 | Mukawa |
| 2010/0053565 A1 | 3/2010 | Mizushima et al. |
| 2010/0079865 A1 | 4/2010 | Saarikko et al. |
| 2010/0086256 A1 | 4/2010 | Ben Bakir et al. |
| 2010/0097674 A1 | 4/2010 | Kasazumi et al. |
| 2010/0097820 A1 | 4/2010 | Owen et al. |
| 2010/0103078 A1 | 4/2010 | Mukawa et al. |
| 2010/0134534 A1 | 6/2010 | Seesselberg et al. |
| 2010/0141905 A1 | 6/2010 | Burke |
| 2010/0149073 A1 | 6/2010 | Chaum et al. |
| 2010/0202725 A1 | 8/2010 | Popovich et al. |
| 2010/0220293 A1 | 9/2010 | Mizushima et al. |
| 2010/0231532 A1 | 9/2010 | Nho et al. |
| 2010/0246003 A1 | 9/2010 | Simmonds et al. |
| 2010/0246004 A1 | 9/2010 | Simmonds |
| 2010/0284085 A1 | 11/2010 | Laakkonen |
| 2010/0284090 A1 | 11/2010 | Simmonds |
| 2010/0284180 A1 | 11/2010 | Popovich et al. |
| 2010/0321781 A1 | 12/2010 | Levola et al. |
| 2011/0019874 A1 | 1/2011 | Jarvenpaa et al. |
| 2011/0026128 A1 | 2/2011 | Baker et al. |
| 2011/0032602 A1 | 2/2011 | Rothenberg et al. |
| 2011/0032618 A1 | 2/2011 | Handerek et al. |
| 2011/0032706 A1 | 2/2011 | Mukawa |
| 2011/0063604 A1 | 3/2011 | Hamre et al. |
| 2011/0102711 A1 | 5/2011 | Sutherland et al. |
| 2011/0109880 A1 | 5/2011 | Nummela |
| 2011/0187293 A1 | 8/2011 | Travis et al. |
| 2011/0235179 A1 | 9/2011 | Simmonds |
| 2011/0236803 A1 | 9/2011 | Weiser et al. |
| 2011/0242661 A1 | 10/2011 | Simmonds |
| 2011/0242670 A1 | 10/2011 | Simmonds |
| 2011/0249309 A1 | 10/2011 | McPheters et al. |
| 2011/0274435 A1 | 11/2011 | Fini et al. |
| 2012/0027347 A1 | 2/2012 | Mathal et al. |
| 2012/0033306 A1 | 2/2012 | Valera et al. |
| 2012/0044572 A1 | 2/2012 | Simmonds et al. |
| 2012/0044573 A1 | 2/2012 | Simmonds et al. |
| 2012/0062850 A1 | 3/2012 | Travis |
| 2012/0062998 A1 | 3/2012 | Schultz et al. |
| 2012/0075168 A1 | 3/2012 | Osterhout et al. |
| 2012/0081789 A1 | 4/2012 | Mukawa et al. |
| 2012/0092632 A1 | 4/2012 | McLeod et al. |
| 2012/0120493 A1 | 5/2012 | Simmonds et al. |
| 2012/0162549 A1 | 6/2012 | Gao et al. |
| 2012/0183888 A1 | 7/2012 | Oliveira et al. |
| 2012/0194420 A1 | 8/2012 | Osterhout et al. |
| 2012/0200532 A1 | 8/2012 | Powell et al. |
| 2012/0206811 A1 | 8/2012 | Mukawa et al. |
| 2012/0206937 A1 | 8/2012 | Travis et al. |
| 2012/0207432 A1 | 8/2012 | Travis et al. |
| 2012/0207434 A1 | 8/2012 | Large |
| 2012/0214089 A1 | 8/2012 | Hönel et al. |
| 2012/0214090 A1 | 8/2012 | Weiser et al. |
| 2012/0218301 A1* | 8/2012 | Miller ............ G06Q 30/02 345/633 |
| 2012/0235886 A1 | 9/2012 | Border et al. |
| 2012/0290973 A1 | 11/2012 | Robertson et al. |
| 2012/0300311 A1 | 11/2012 | Simmonds et al. |
| 2013/0016324 A1 | 1/2013 | Travis |
| 2013/0021392 A1 | 1/2013 | Travis |
| 2013/0021586 A1 | 1/2013 | Lippey |
| 2013/0033485 A1 | 2/2013 | Kollin et al. |
| 2013/0039619 A1 | 2/2013 | Laughlin |
| 2013/0044376 A1 | 2/2013 | Valera et al. |
| 2013/0059233 A1 | 3/2013 | Askham |
| 2013/0069850 A1 | 3/2013 | Mukawa et al. |
| 2013/0077049 A1 | 3/2013 | Bohn |
| 2013/0101253 A1 | 4/2013 | Popovich et al. |
| 2013/0114043 A1* | 5/2013 | Balan ............ A61B 3/113 351/210 |
| 2013/0117377 A1 | 5/2013 | Miller |
| 2013/0125027 A1 | 5/2013 | Abovitz et al. |
| 2013/0128230 A1 | 5/2013 | Macnamara |
| 2013/0143336 A1 | 6/2013 | Jain |
| 2013/0163089 A1 | 6/2013 | Bohn |
| 2013/0176704 A1 | 7/2013 | Lanman et al. |
| 2013/0207887 A1 | 8/2013 | Raffle et al. |
| 2013/0224634 A1 | 8/2013 | Berneth et al. |
| 2013/0229717 A1 | 9/2013 | Amitai |
| 2013/0250207 A1 | 9/2013 | Bohn |
| 2013/0250380 A1 | 9/2013 | Fujikawa et al. |
| 2013/0250430 A1 | 9/2013 | Robbins et al. |
| 2013/0250431 A1 | 9/2013 | Robbins et al. |
| 2013/0267309 A1 | 10/2013 | Robbins et al. |
| 2013/0271731 A1 | 10/2013 | Popovich et al. |
| 2013/0277890 A1 | 10/2013 | Bowman et al. |
| 2013/0286053 A1 | 10/2013 | Fleck et al. |
| 2013/0312811 A1 | 11/2013 | Aspnes et al. |
| 2013/0322810 A1 | 12/2013 | Robbins |
| 2013/0342525 A1 | 12/2013 | Benko et al. |

(56) References Cited

U.S. PATENT DOCUMENTS

| | | |
|---|---|---|
| 2014/0003762 A1 | 1/2014 | Macnamara |
| 2014/0022616 A1 | 1/2014 | Popovich et al. |
| 2014/0024159 A1 | 1/2014 | Jain |
| 2014/0055845 A1 | 2/2014 | Jain |
| 2014/0063055 A1 | 3/2014 | Osterhout et al. |
| 2014/0064655 A1 | 3/2014 | Nguyen et al. |
| 2014/0071538 A1 | 3/2014 | Muller |
| 2014/0098010 A1 | 4/2014 | Travis |
| 2014/0104665 A1 | 4/2014 | Popovich et al. |
| 2014/0118647 A1 | 5/2014 | Momonoi et al. |
| 2014/0130132 A1 | 5/2014 | Cahill et al. |
| 2014/0140653 A1 | 5/2014 | Brown et al. |
| 2014/0140654 A1 | 5/2014 | Brown et al. |
| 2014/0146394 A1 | 5/2014 | Tout et al. |
| 2014/0160576 A1 | 6/2014 | Robbins et al. |
| 2014/0168260 A1 | 6/2014 | O'Brien et al. |
| 2014/0168735 A1 | 6/2014 | Yuan et al. |
| 2014/0168783 A1 | 6/2014 | Luebke et al. |
| 2014/0176528 A1 | 6/2014 | Robbins |
| 2014/0177023 A1 | 6/2014 | Gao et al. |
| 2014/0185286 A1 | 7/2014 | Popovich et al. |
| 2014/0198128 A1 | 7/2014 | Hong et al. |
| 2014/0198896 A1 | 7/2014 | Hemmendorff et al. |
| 2014/0204455 A1 | 7/2014 | Popovich et al. |
| 2014/0211322 A1 | 7/2014 | Bohn et al. |
| 2014/0218468 A1 | 8/2014 | Gao et al. |
| 2014/0218801 A1 | 8/2014 | Simmonds et al. |
| 2014/0232759 A1 | 8/2014 | Simmonds et al. |
| 2014/0240834 A1 | 8/2014 | Mason |
| 2014/0240842 A1 | 8/2014 | Nguyen et al. |
| 2014/0267420 A1 | 9/2014 | Schowengerdt et al. |
| 2014/0268353 A1 | 9/2014 | Fujimura et al. |
| 2014/0300947 A1 | 10/2014 | Fattal et al. |
| 2014/0300960 A1 | 10/2014 | Santori et al. |
| 2014/0300966 A1 | 10/2014 | Travers et al. |
| 2014/0327970 A1 | 11/2014 | Bohn et al. |
| 2014/0330159 A1 | 11/2014 | Costa et al. |
| 2014/0367719 A1 | 12/2014 | Jain |
| 2014/0375542 A1 | 12/2014 | Robbins et al. |
| 2014/0375789 A1 | 12/2014 | Lou et al. |
| 2014/0375790 A1 | 12/2014 | Robbins et al. |
| 2015/0001677 A1 | 1/2015 | Palumbo et al. |
| 2015/0003796 A1 | 1/2015 | Bennett |
| 2015/0009550 A1 | 1/2015 | Misago et al. |
| 2015/0010265 A1 | 1/2015 | Popovich et al. |
| 2015/0015946 A1 | 1/2015 | Muller |
| 2015/0016777 A1 | 1/2015 | Abovitz et al. |
| 2015/0035744 A1 | 2/2015 | Robbins et al. |
| 2015/0036068 A1 | 2/2015 | Fattal et al. |
| 2015/0058791 A1 | 2/2015 | Robertson et al. |
| 2015/0062675 A1 | 3/2015 | Ayres et al. |
| 2015/0062707 A1 | 3/2015 | Simmonds et al. |
| 2015/0086163 A1 | 3/2015 | Valera et al. |
| 2015/0125109 A1 | 5/2015 | Robbins et al. |
| 2015/0148728 A1 | 5/2015 | Sallum et al. |
| 2015/0185475 A1 | 7/2015 | Saarikko et al. |
| 2015/0235447 A1 | 8/2015 | Abovitz et al. |
| 2015/0235448 A1 | 8/2015 | Schowengerdt et al. |
| 2015/0247975 A1 | 9/2015 | Abovitz et al. |
| 2015/0260994 A1 | 9/2015 | Akutsu et al. |
| 2015/0262424 A1 | 9/2015 | Tabaka et al. |
| 2015/0268415 A1 | 9/2015 | Schowengerdt et al. |
| 2015/0277375 A1 | 10/2015 | Large et al. |
| 2015/0288129 A1 | 10/2015 | Jain |
| 2015/0289762 A1 | 10/2015 | Popovich et al. |
| 2015/0346490 A1 | 12/2015 | Tekolste et al. |
| 2015/0346495 A1 | 12/2015 | Welch et al. |
| 2015/0355394 A1 | 12/2015 | Leighton et al. |
| 2016/0003847 A1 | 1/2016 | Ryan et al. |
| 2016/0004090 A1 | 1/2016 | Popovich et al. |
| 2016/0026253 A1 | 1/2016 | Bradski et al. |
| 2016/0033705 A1 | 2/2016 | Fattal |
| 2016/0033706 A1 | 2/2016 | Fattal et al. |
| 2016/0038992 A1 | 2/2016 | Arthur et al. |
| 2016/0041387 A1 | 2/2016 | Valera et al. |
| 2016/0077338 A1 | 3/2016 | Robbins et al. |
| 2016/0085300 A1 | 3/2016 | Robbins et al. |
| 2016/0116739 A1 | 4/2016 | TeKolste et al. |
| 2016/0124223 A1 | 5/2016 | Shinbo et al. |
| 2016/0132025 A1 | 5/2016 | Taff et al. |
| 2016/0195664 A1 | 7/2016 | Fattal et al. |
| 2016/0195720 A1 | 7/2016 | Travis et al. |
| 2016/0209648 A1 | 7/2016 | Haddick et al. |
| 2016/0209657 A1 | 7/2016 | Popovich et al. |
| 2016/0231568 A1 | 8/2016 | Saarikko et al. |
| 2016/0266398 A1 | 9/2016 | Poon et al. |
| 2016/0274362 A1 | 9/2016 | Tinch et al. |
| 2016/0299344 A1 | 10/2016 | Dobschal et al. |
| 2016/0320536 A1 | 11/2016 | Simmonds et al. |
| 2016/0327705 A1 | 11/2016 | Simmonds et al. |
| 2016/0341964 A1 | 11/2016 | Amitai |
| 2017/0003505 A1 | 1/2017 | Vallius et al. |
| 2017/0010488 A1 | 1/2017 | Klug et al. |
| 2017/0030550 A1 | 2/2017 | Popovich et al. |
| 2017/0031160 A1 | 2/2017 | Popovich et al. |
| 2017/0031171 A1 | 2/2017 | Vallius et al. |
| 2017/0034435 A1 | 2/2017 | Vallius |
| 2017/0038579 A1 | 2/2017 | Yeoh et al. |
| 2017/0052376 A1 | 2/2017 | Amitai et al. |
| 2017/0059759 A1 | 3/2017 | Ayres et al. |
| 2017/0102543 A1 | 4/2017 | Vallius |
| 2017/0115487 A1 | 4/2017 | Travis et al. |
| 2017/0123208 A1 | 5/2017 | Vallius |
| 2017/0131460 A1 | 5/2017 | Lin et al. |
| 2017/0131546 A1 | 5/2017 | Woltman et al. |
| 2017/0131551 A1 | 5/2017 | Robbins et al. |
| 2017/0180404 A1 | 6/2017 | Bersch et al. |
| 2017/0180408 A1 | 6/2017 | Yu et al. |
| 2017/0219841 A1 | 8/2017 | Popovich et al. |
| 2017/0299860 A1 | 10/2017 | Wall et al. |
| 2018/0003805 A1 | 1/2018 | Popovich et al. |
| 2018/0113303 A1 | 4/2018 | Popovich et al. |
| 2018/0120669 A1 | 5/2018 | Popovich et al. |
| 2018/0143449 A1 | 5/2018 | Popovich et al. |
| 2018/0232048 A1 | 8/2018 | Popovich et al. |
| 2018/0275402 A1 | 9/2018 | Popovich et al. |
| 2019/0041634 A1 | 2/2019 | Popovich et al. |
| 2019/0064735 A1 | 2/2019 | Waldern et al. |
| 2019/0072723 A1 | 3/2019 | Waldern et al. |
| 2019/0179153 A1 | 6/2019 | Popovich et al. |
| 2019/0361096 A1 | 11/2019 | Popovich et al. |
| 2020/0033604 A1 | 1/2020 | Schmulen et al. |
| 2020/0041787 A1 | 2/2020 | Popovich et al. |
| 2020/0064637 A1 | 2/2020 | Popovich et al. |
| 2020/0089319 A1 | 3/2020 | Popovich et al. |
| 2020/0096768 A1 | 3/2020 | Border et al. |
| 2020/0247016 A1 | 8/2020 | Calafiore |
| 2020/0249568 A1 | 8/2020 | Rao et al. |
| 2020/0333606 A1 | 10/2020 | Popovich et al. |
| 2020/0341272 A1 | 10/2020 | Popovich et al. |
| 2020/0386869 A1 | 12/2020 | Popovich et al. |
| 2021/0109285 A1 | 4/2021 | Jiang et al. |
| 2021/0191122 A1 | 6/2021 | Yaroshchuk et al. |
| 2021/0199873 A1 | 7/2021 | Shi et al. |
| 2021/0199971 A1 | 7/2021 | Lee et al. |
| 2021/0238374 A1 | 8/2021 | Ye et al. |
| 2021/0255463 A1 | 8/2021 | Popovich et al. |
| 2022/0019015 A1 | 1/2022 | Calafiore et al. |
| 2022/0043511 A1 | 2/2022 | Popovich et al. |
| 2022/0066206 A1 | 3/2022 | Popovich et al. |
| 2022/0082739 A1 | 3/2022 | Franke et al. |
| 2022/0091323 A1 | 3/2022 | Yaroshchuk et al. |
| 2022/0204790 A1 | 6/2022 | Zhang et al. |
| 2022/0206232 A1 | 6/2022 | Zhang et al. |

FOREIGN PATENT DOCUMENTS

| | | |
|---|---|---|
| CN | 1066936 A | 12/1992 |
| CN | 1320217 A | 10/2001 |
| CN | 1886680 A | 12/2006 |
| CN | 101103297 A | 1/2008 |
| CN | 100492099 C | 5/2009 |
| CN | 103000188 A | 3/2013 |
| CN | 103823267 A | 5/2014 |

(56) References Cited

FOREIGN PATENT DOCUMENTS

| | | |
|---|---|---|
| CN | 103959133 A | 7/2014 |
| CN | 104035157 A | 9/2014 |
| CN | 104040410 A | 9/2014 |
| CN | 104136952 A | 11/2014 |
| CN | 104204901 A | 12/2014 |
| CN | 104956252 A | 9/2015 |
| CN | 105074537 A | 11/2015 |
| CN | 105074539 A | 11/2015 |
| CN | 105190407 A | 12/2015 |
| CN | 105229514 A | 1/2016 |
| CN | 105393159 A | 3/2016 |
| CN | 105408801 A | 3/2016 |
| CN | 105408802 A | 3/2016 |
| CN | 105408803 A | 3/2016 |
| CN | 105531716 A | 4/2016 |
| CN | 105705981 A | 6/2016 |
| CN | 107533137 A | 1/2018 |
| CN | 107873086 A | 4/2018 |
| CN | 109073889 A | 12/2018 |
| CN | 107873086 B | 3/2020 |
| CN | 111323867 A | 6/2020 |
| CN | 109073889 B | 4/2021 |
| DE | 19751190 A1 | 5/1999 |
| DE | 10221837 A1 | 12/2003 |
| DE | 102012108424 A1 | 3/2014 |
| EP | 0795775 A2 | 9/1997 |
| EP | 1347641 A1 | 9/2003 |
| EP | 1413972 A1 | 4/2004 |
| EP | 1526709 A2 | 4/2005 |
| EP | 1748305 A1 | 1/2007 |
| EP | 1413972 B1 | 10/2008 |
| EP | 2110701 A1 | 10/2009 |
| EP | 2244114 A1 | 10/2010 |
| EP | 2326983 A1 | 6/2011 |
| EP | 1828832 B1 | 5/2013 |
| EP | 2733517 A1 | 5/2014 |
| EP | 1573369 B1 | 7/2014 |
| EP | 2929378 A1 | 10/2015 |
| EP | 2748670 B1 | 11/2015 |
| EP | 2995986 A1 | 3/2016 |
| EP | 3198192 A1 | 8/2017 |
| EP | 3245444 A1 | 11/2017 |
| EP | 3245551 A2 | 11/2017 |
| EP | 3248026 A1 | 11/2017 |
| EP | 3398007 A1 | 11/2018 |
| EP | 3245551 B1 | 9/2019 |
| EP | 3248026 B1 | 9/2019 |
| EP | 3245444 B1 | 9/2021 |
| GB | 2140935 A | 12/1984 |
| GB | 2508661 A | 6/2014 |
| GB | 2509536 A | 7/2014 |
| GB | 2512077 A | 9/2014 |
| GB | 2514658 A | 12/2014 |
| HK | 1204684 A1 | 11/2015 |
| HK | 1205563 A1 | 12/2015 |
| HK | 1205793 A1 | 12/2015 |
| HK | 1206101 A1 | 12/2015 |
| JP | 02186319 A | 7/1990 |
| JP | 03239384 A | 10/1991 |
| JP | H05066427 A | 3/1993 |
| JP | 5-224018 A | 9/1993 |
| JP | 06294952 A | 10/1994 |
| JP | 7-66383 A | 3/1995 |
| JP | 07098439 A | 4/1995 |
| JP | 0990312 A | 4/1997 |
| JP | H10503279 A | 3/1998 |
| JP | 11109320 A | 4/1999 |
| JP | 11142806 A | 5/1999 |
| JP | 2953444 B2 | 9/1999 |
| JP | 2000056259 A | 2/2000 |
| JP | 2000267042 A | 9/2000 |
| JP | 2001027739 A | 1/2001 |
| JP | 2001296503 A | 10/2001 |
| JP | 2002090858 A | 3/2002 |
| JP | 2002122906 A | 4/2002 |
| JP | 2002162598 A | 6/2002 |
| JP | 2002523802 A | 7/2002 |
| JP | 2003066428 A | 3/2003 |
| JP | 2003270419 A | 9/2003 |
| JP | 2008112187 A | 5/2008 |
| JP | 2009036955 A | 2/2009 |
| JP | 2009211091 A | 9/2009 |
| JP | 4367775 B2 | 11/2009 |
| JP | 2011158907 A | 8/2011 |
| JP | 2012137616 A | 7/2012 |
| JP | 2012163642 A | 8/2012 |
| JP | 5303928 B2 | 10/2013 |
| JP | 2018512562 A | 5/2018 |
| JP | 6867947 B2 | 4/2021 |
| KR | 20100092059 A | 8/2010 |
| KR | 20140140063 A | 12/2014 |
| KR | 20140142337 A | 12/2014 |
| TW | 200535633 A | 11/2005 |
| TW | 200801583 A | 1/2008 |
| TW | 201314263 A | 4/2013 |
| TW | 201600943 A | 1/2016 |
| TW | 201604601 A | 2/2016 |
| WO | 1997001133 A1 | 1/1997 |
| WO | 1997027519 A1 | 7/1997 |
| WO | 1998004650 A1 | 2/1998 |
| WO | 1999009440 A1 | 2/1999 |
| WO | 9931658 A1 | 6/1999 |
| WO | 2000016136 A1 | 3/2000 |
| WO | 0023832 A1 | 4/2000 |
| WO | 2000023830 | 4/2000 |
| WO | 2000023847 | 4/2000 |
| WO | 2001050200 A2 | 7/2001 |
| WO | 2001090822 A1 | 11/2001 |
| WO | 2002082168 A1 | 10/2002 |
| WO | 2003081320 A1 | 10/2003 |
| WO | 2004053531 A3 | 11/2004 |
| WO | 2005001753 A1 | 1/2005 |
| WO | 2005006065 A8 | 1/2005 |
| WO | 2005006065 A3 | 2/2005 |
| WO | 2005073798 A1 | 8/2005 |
| WO | 2006002870 A1 | 1/2006 |
| WO | 2006064301 A1 | 6/2006 |
| WO | 2006064325 A1 | 6/2006 |
| WO | 2006064334 A1 | 6/2006 |
| WO | 2006102073 A2 | 9/2006 |
| WO | 2006132614 A1 | 12/2006 |
| WO | 2006102073 A3 | 1/2007 |
| WO | 2007015141 A2 | 2/2007 |
| WO | 2007029032 A1 | 3/2007 |
| WO | 2007085682 A1 | 8/2007 |
| WO | 2007130130 A2 | 11/2007 |
| WO | 2007141587 A1 | 12/2007 |
| WO | 2007141589 A1 | 12/2007 |
| WO | 2008011066 A2 | 1/2008 |
| WO | 2008011066 A9 | 5/2008 |
| WO | 2008100545 A2 | 8/2008 |
| WO | 2008011066 A3 | 12/2008 |
| WO | 2009013597 A2 | 1/2009 |
| WO | 2009077802 A1 | 6/2009 |
| WO | 2009077803 A1 | 6/2009 |
| WO | 2009101238 A1 | 8/2009 |
| WO | 2007130130 A3 | 9/2009 |
| WO | 2009155437 A1 | 12/2009 |
| WO | 2009155437 A8 | 3/2010 |
| WO | 2010023444 A1 | 3/2010 |
| WO | 2010057219 A1 | 5/2010 |
| WO | 2010067114 A1 | 6/2010 |
| WO | 2010078856 A1 | 7/2010 |
| WO | 2010104692 A2 | 9/2010 |
| WO | 2010122330 A1 | 10/2010 |
| WO | 2010125337 A2 | 11/2010 |
| WO | 2011032005 A1 | 3/2011 |
| WO | 2011042711 A2 | 4/2011 |
| WO | 2011051660 A1 | 5/2011 |
| WO | 2011055109 A2 | 5/2011 |
| WO | 2011042711 A3 | 6/2011 |
| WO | 2011073673 A1 | 6/2011 |
| WO | 2011107831 A1 | 9/2011 |
| WO | 2011110821 A1 | 9/2011 |

(56) References Cited

FOREIGN PATENT DOCUMENTS

| | | | |
|---|---|---|---|
| WO | 2011131978 A1 | 10/2011 |
| WO | 2012052352 A1 | 4/2012 |
| WO | 2012062658 A1 | 5/2012 |
| WO | 2012158950 A1 | 11/2012 |
| WO | 2012172295 A1 | 12/2012 |
| WO | 2013027004 A1 | 2/2013 |
| WO | 2013027006 A1 | 2/2013 |
| WO | 2013034879 A1 | 3/2013 |
| WO | 2013049012 A1 | 4/2013 |
| WO | 2013102759 A2 | 7/2013 |
| WO | 2013163347 A1 | 10/2013 |
| WO | 2013167864 A1 | 11/2013 |
| WO | 2014064427 A1 | 5/2014 |
| WO | 2014080155 A1 | 5/2014 |
| WO | 2014085734 A1 | 6/2014 |
| WO | 2014090379 A1 | 6/2014 |
| WO | 2014091200 A1 | 6/2014 |
| WO | 2014093601 A1 | 6/2014 |
| WO | 2014100182 A1 | 6/2014 |
| WO | 2014113506 A1 | 7/2014 |
| WO | 2014116615 A1 | 7/2014 |
| WO | 2014130383 A1 | 8/2014 |
| WO | 2014144526 A2 | 9/2014 |
| WO | 2014159621 A1 | 10/2014 |
| WO | 2014164901 A1 | 10/2014 |
| WO | 2014176695 A1 | 11/2014 |
| WO | 2014179632 A1 | 11/2014 |
| WO | 2014188149 A1 | 11/2014 |
| WO | 2014209733 A1 | 12/2014 |
| WO | 2014209819 A1 | 12/2014 |
| WO | 2014209820 A1 | 12/2014 |
| WO | 2014209821 A1 | 12/2014 |
| WO | 2014210349 A1 | 12/2014 |
| WO | 2015006784 A2 | 1/2015 |
| WO | 2015017291 A1 | 2/2015 |
| WO | 2015069553 A1 | 5/2015 |
| WO | 2015081313 A2 | 6/2015 |
| WO | 2015117039 A1 | 8/2015 |
| WO | 2015145119 A1 | 10/2015 |
| WO | 2016010289 A1 | 1/2016 |
| WO | 2016020643 A1 | 2/2016 |
| WO | 2016025350 A1 | 2/2016 |
| WO | 2016046514 A1 | 3/2016 |
| WO | 2016103263 A1 | 6/2016 |
| WO | 2016111706 A1 | 7/2016 |
| WO | 2016111707 A1 | 7/2016 |
| WO | 2016111708 A1 | 7/2016 |
| WO | 2016111709 A1 | 7/2016 |
| WO | 2016113533 A2 | 7/2016 |
| WO | 2016113534 A1 | 7/2016 |
| WO | 2016116733 A1 | 7/2016 |
| WO | 2016118107 A1 | 7/2016 |
| WO | 2016122679 A1 | 8/2016 |
| WO | 2016113533 A3 | 10/2016 |
| WO | 2016181108 A1 | 11/2016 |
| WO | 2017060665 A1 | 4/2017 |
| WO | 2017134412 A1 | 8/2017 |
| WO | 2017162999 A1 | 9/2017 |
| WO | 2017180403 A1 | 10/2017 |
| WO | 2017182771 A1 | 10/2017 |
| WO | 2017203200 A1 | 11/2017 |
| WO | 2017203201 A1 | 11/2017 |
| WO | 2017207987 A1 | 12/2017 |
| WO | 2018096359 A3 | 7/2018 |
| WO | 2018150163 A1 | 8/2018 |
| WO | 2019077307 A1 | 4/2019 |
| WO | 2019122806 A1 | 6/2019 |
| WO | 2019171038 A1 | 9/2019 |
| WO | 2020212682 A1 | 10/2020 |
| WO | 2021032982 A1 | 2/2021 |
| WO | 2021032983 A1 | 2/2021 |
| WO | 2021044121 A1 | 3/2021 |
| WO | 2021242898 A1 | 12/2021 |

OTHER PUBLICATIONS

Gerritsen et al., "Application of Kogelnik's two-wave theory to deep, slanted, highly efficient, relief transmission gratings", Applied Optics, Mar. 1, 1991, vol. 30; No. 7, pp. 807-814.

Golub et al., "Bragg properties of efficient surface relief gratings in the resonance domain", Optics Communications, Feb. 24, 2004, vol. 235, pp. 261-267, doi: 10.1016/j.optcom.2004.02.069.

Natarajan et al., "Electro-Optical Switching Characteristics of Volume Holograms in Polymer Dispersed Liquid Crystals", Journal of Nonlinear Optical Physics and Materials, Jan. 1996, vol. 5, No. 1, pp. 89-98.

Qi Xiaodong et al., "Surface emitting distributed feedback semiconductor laser and grating coupled semiconductor laser", Chinese Optics and Applied Optics Oct. 31, 2010 vol. 3 No. 5, pp. 415-431.

Sutherland et al., "Liquid crystal bragg gratings: dynamic optical elements for spatial light modulators", Hardened Materials Branch, Hardened Materials Branch, AFRL-ML-WP-TP-2007-514, Jan. 2007, Wright-Patterson Air Force Base, OH, 18 pgs.

Yokomori, "Dielectric surface-relief gratings with high diffraction efficiency", Applied Optics, Jul. 15, 1984, vol. 23; No. 14, pp. 2303-2310.

International Preliminary Report on Patentability for International Application No. PCT/GB2016/000005, Report dated Jul. 18, 2017, dated Jul. 27, 2017, 7 pgs.

International Preliminary Report on Patentability for International Application No. PCT/GB2016/000051, Report dated Sep. 19, 2017, dated Sep. 28, 2017, 7 Pgs.

International Preliminary Report on Patentability for International Application PCT/GB2009/051676, dated Jun. 14, 2011, dated Jun. 23, 2011, 6 pgs.

International Preliminary Report on Patentability for International Application PCT/GB2011/000349, dated Sep. 18, 2012, dated Sep. 27, 2012, 10 pgs.

International Preliminary Report on Patentability for International Application PCT/GB2012/000331, dated Oct. 8, 2013, dated Oct. 17, 2013, 8 pgs.

International Preliminary Report on Patentability for International Application PCT/GB2012/000677, dated Feb. 25, 2014, dated Mar. 6, 2014, 5 pgs.

International Preliminary Report on Patentability for International Application PCT/GB2013/000005, dated Jul. 8, 2014, dated Jul. 17, 2014, 12 pgs.

International Preliminary Report on Patentability for International Application PCT/GB2013/000210, dated Nov. 11, 2014, dated Nov. 20, 2014, 6 pgs.

International Preliminary Report on Patentability for International Application PCT/GB2014/000197, dated Nov. 24, 2015, dated Dec. 3, 2015, 7 pgs.

International Preliminary Report on Patentability for International Application PCT/GB2014/000295, dated Feb. 2, 2016, dated Feb. 11, 2016, 4 pgs.

International Preliminary Report on Patentability for International Application PCT/GB2015/000225, dated Feb. 14, 2017, dated Feb. 23, 2017, 8 pgs.

International Preliminary Report on Patentability for International Application PCT/GB2015/000274, dated Mar. 28, 2017, dated Apr. 6, 2017, 8 pgs.

International Preliminary Report on Patentability for International Application PCT/GB2016/000003, dated Jul. 18, 2017, dated Jul. 27, 2017, 11 Pgs.

International Preliminary Report on Patentability for International Application PCT/GB2016/000014, dated Jul. 25, 2017, dated Aug. 3, 2017, 7 pgs.

International Preliminary Report on Patentability for International Application PCT/GB2017/000015, Report Completed Aug. 7, 2018, dated Aug. 16, 2018, 7 pgs.

International Preliminary Report on Patentability for International Application PCT/US2014/011736, dated Jul. 21, 2015, dated Jul. 30, 2015, 9 pgs.

(56) References Cited

OTHER PUBLICATIONS

International Preliminary Report on Patentability for International Application PCT/US2016/017091, dated Aug. 15, 2017, dated Aug. 24, 2017, 5 pgs.
International Search Report and Written Opinion for International Application No. PCT/GB2017/000015, Search completed Apr. 25, 2017, dated May 8, 2017, 10 pgs.
International Search Report and Written Opinion for International Application No. PCT/US2014/011736, completed Apr. 18, 2014, dated May 8, 2014, 10 pgs.
International Search Report and Written Opinion for International Application PCT/GB2009/051676, completed May 10, 2010, dated May 18, 2010, 7 pgs.
International Search Report and Written Opinion for International Application PCT/US2016/017091, completed by the European Patent Office dated Apr. 20, 2016, 7 pgs.
International Search Report for International Application No. PCT/GB2014/000295, completed Nov. 18, 2014, dated Jan. 5, 2015, 4 pgs.
International Search Report for International Application PCT/GB2017/000040, dated Jul. 18, 2017, completed Jul. 10, 2017, 3 pgs.
International Search Report for PCT/GB2011/000349, completed by the European Patent Office dated Aug. 17, 2011, 4 pgs.
International Search Report for PCT/GB2012/000331, completed by the European Patent Office on Aug. 29, 2012, 4 pgs.
International Search Report for PCT/GB2012/000677, completed by the European Patent Office dated Dec. 10, 2012, 4 pgs.
International Search Report for PCT/GB2013/000005, completed by the European Patent Office on Jul. 16, 2013, 3 pgs.
International Search Report for PCT/GB2013/000210, completed by the European Patent Office dated Aug. 12, 2013, 3 pgs.
International Search Report for PCT/GB2014/000197, Completed by the European Patent Office dated Jul. 31, 2014, 3 pgs.
International Search Report for PCT/GB2015/000203, completed by the European Patent Office dated Oct. 9, 2015, 4 pgs.
International Search Report for PCT/GB2015/000225, completed by the European Patent Office dated Nov. 10, 2015, dated Dec. 2, 2016, 5 pgs.
International Search Report for PCT/GB2015/000274, completed by the European Patent Office dated Jan. 7, 2016, 4 pgs.
International Search Report for PCT/GB2016/000003, Completed by the European Patent Office dated May 31, 2016, 6 pgs.
International Search Report for PCT/GB2016/000005, completed by the European Patent Office dated May 27, 2016, 4 pgs.
International Search Report for PCT/GB2016/000014, completed by the European Patent Office dated Jun. 27, 2016, 4 pgs.
International Search Report for PCT/GB2016/000051, Completed Aug. 11, 2016, 3 Pgs.
Written Opinion for International Application No. PCT/GB2011/000349, completed Aug. 17, 2011, dated Aug. 25, 2011, 9 pgs.
Written Opinion for International Application No. PCT/GB2012/000331, completed Aug. 29, 2012, dated Sep. 6, 2012, 7 pgs.
Written Opinion for International Application No. PCT/GB2012/000677, completed Dec. 10, 2012, dated Dec. 17, 2012, 4 pgs.
Written Opinion for International Application No. PCT/GB2013/000005, search completed Jul. 16, 2013, dated Jul. 24, 2013, 11 pgs.
Written Opinion for International Application No. PCT/GB2014/000197, Search completed Jul. 31, 2014, dated Aug. 7, 2014, 6 Pgs.
Written Opinion for International Application No. PCT/GB2014/000295, search completed Nov. 18, 2014, dated Jan. 5, 2015, 3 pgs.
Written Opinion for International Application No. PCT/GB2015/000225, search completed Nov. 10, 2015, dated Feb. 4, 2016, 7 pgs.
Written Opinion for International Application No. PCT/GB2015/000274, search completed Jan. 7, 2016, dated Jan. 19, 2016, 7 pgs.
Written Opinion for International Application No. PCT/GB2016/000014, search completed Jun. 27, 2016, dated Jul. 7, 2016, 6 pgs.
Written Opinion for International Application No. PCT/GB2016/000051, Search completed Aug. 11, 2016, dated Aug. 22, 2016, 6 Pgs.
Written Opinion for International Application No. PCT/GB2017/000040, search completed Jul. 10, 2017, dated Jul. 18, 2017, 6 pgs.
Written Opinion for International Application PCT/GB2013/000210, completed Aug. 12, 2013, dated Aug. 20, 2013, 5 pgs.
Written Opinion for International Application PCT/GB2016/000003, completed May 31, 2016, dated Aug. 12, 2016, 10 pgs.
Written Opinion for International Application PCT/GB2016/000005, search completed May 27, 2016, dated Jun. 6, 2016, 6 pgs.
"Agilent ADNS-2051 Optical Mouse Sensor: Data Sheet", Agilent Technologies, Jan. 9, 2002, 40 pgs.
"Application Note—MOXTEK ProFlux Polarizer use with LCOS displays", CRL Opto Limited, http://www.crlopto.com, 2003, 6 pgs.
"Application Note AN16: Optical Considerations for Bridgelux LED Arrays", BridgeLux, Jul. 31, 2010, 23 pgs.
"Application Note: Variable Attenuator for Lasers", Technology and Applications Center, Newport Corporation, www.newport.com, 2006, DS-08067, 6 pgs.
"Bae Systems to Unveil Q-Sight Family of Helmet-Mounted Display at AUSA Symposium", Released on Tuesday, Oct. 9, 2007, 1 pg.
"Beam Steering Using Liquid Crystals", Boulder Nonlinear Systems, Inc., info@bnonlinear.com, May 8, 2001, 4 pgs.
"BragGrate—Deflector: Transmitting Volume Bragg Grating for angular selection and magnification", 2015, www.OptiGrate.com.
"Cree XLamp XP-E LEDs", Cree, Inc., Retrieved from www.cree.com/Xlamp, CLD-DS18 Rev 17, 2013, 17 pgs.
"Desmodur N 3900", Bayer MaterialScience AG, Mar. 18, 2013, www.bayercoatings.com, 4 pgs.
"Digilens—Innovative Augmented Reality Display and Sensor Solutions for OEMs", Jun. 6, 2017, 31 pgs.
"Exotic Optical Components", Building Electro-Optical Systems, Making It All Work, Chapter 7, John Wiley & Sons, Inc., pp. 233-261.
"FHS Lenses Series", Fraen Corporation, www.fraen.com, Jun. 16, 2003, 10 pgs.
"FLP Lens Series for LUXEONTM Rebel and Rebel ES LEDs", Fraen Corporation, www.fraensrl.com, Aug. 7, 2015, 8 pgs.
"Head-up Displays, See-through display for military aviation", BAE Systems, 2016, 3 pgs.
"Holder for LUXEON Rebel—Part No. 180", Polymer Optics Ltd., 2008, 12 pgs.
"LED 7-Segment Displays", Lumex, uk.digikey.com, 2003, UK031, 36 pgs.
"LED325W UVTOP UV LED with Window", Thorlabs, Specifications and Documentation, 21978-S01 Rev. A, Apr. 8, 2011, 5 pgs.
"Liquid Crystal Phases", Phases of Liquid Crystals, http://plc.cwru.edu/tutorial/enhanced/files/lc/phase, Retrieved on Sep. 21, 2004, 6 pgs.
"LiteHUD Head-up display", BAE Systems, 2016, 2 pgs.
"LiteHUD Head-up display infographic", BAE Systems, 2017, 2 pgs.
"Luxeon C: Power Light Source", Philips Lumileds, www.philipslumileds.com, 2012, 18 pgs.
"Luxeon Rebel ES: Leading efficacy and light output, maximum design flexibility", LUXEON Rebel ES Datasheet DS61 20130221, www.philipslumileds.com, 2013, 33 pgs.
"Mobile Display Report", Insight Media, LLC, Apr. 2012, vol. 7, No. 4, 72 pgs.
"Molecular Imprints Imprio 55", Engineering at Illinois, Micro + Nanotechnology Lab, Retrieved from https://mntl.illinois.edu/facilities/cleanrooms/equipment/Nano-Imprint.asp, Dec. 28, 2015, 2 pgs.
"Optical measurements of retinal flow", Industrial Research Limited, Feb. 2012, 18 pgs.
"Osterhout Design Group Develops Next-Generation, Fully-integrated Smart Glasses Using Qualcomm Technologies", ODG, www.osterhoutgroup.com, Sep. 18, 2014, 2 pgs.
"Range Finding Using Pulse Lasers", OSRAM, Opto Semiconductors, Sep. 10, 2004, 7 pgs.
"Response time in Liquid-Crystal Variable Retarders", Meadowlark Optics, Inc., 2005, 4 pgs.
"Secondary Optics Design Considerations for SuperFlux LEDs", Lumileds, application brief AB20-5, Sep. 2002, 23 pgs.

(56) References Cited

OTHER PUBLICATIONS

"Solid-State Optical Mouse Sensor with Quadrature Outputs", IC Datasheet, UniqueICs, Jul. 15, 2004, 11 pgs.
"SVGA TransparentVLSITM Microdisplay Evaluation Kit", Radiant Images, Inc., Product Data Sheet, 2003, 3 pgs.
"Technical Data Sheet LPR1", Luminus Devices, Inc., Luminus Projection Chipset, Release 1, Preliminary, Revision B, Sep. 21, 2004, 9 pgs.
"The Next Generation of TV", SID Information Display, Nov./Dec. 2014, vol. 30, No. 6, 56 pgs.
"Thermal Management Considerations for SuperFlux LEDs", Lumileds, application brief AB20-4, Sep. 2002, 14 pgs.
"UVTOP240", Roithner LaserTechnik GmbH, v 2.0, Jun. 24, 2013, 6 pgs.
"UVTOP310", Roithner LaserTechnik GmbH, v 2.0, Jun. 24, 2013, 6 pgs.
"Velodyne's HDL-64E: A High Definition Lidar Sensor for 3-D Applications", High Definition Lidar, white paper, Oct. 2007, 7 pgs.
"VerLASE Gets Patent for Breakthrough Color Conversion Technology That Enables Full Color MicroLED Arrays for Near Eye Displays", Cision PRweb, Apr. 28, 2015, Retrieved from the Internet http://www.prweb.com/releases/2015/04/prweb12681038.htm, 3 pgs.
"X-Cubes—Revisited for LCOS", BASID, RAF Electronics Corp. Rawson Optics, Inc., Oct. 24, 2002, 16 pgs.
Aachen, "Design of plastic optics for LED applications", Optics Colloquium 2009, Mar. 19, 2009, 30 pgs.
Abbate et al., "Characterization of LC-polymer composites for opto-electronic application", Proceedings of OPTOEL'03, Leganes-Madrid, Spain, Jul. 14-16, 2003, 4 pgs.
Al-Kalbani et al., "Ocular Microtremor laser speckle metrology", Proc. of SPIE, 2009, vol. 7176 717606-1, 12 pgs., doi:10.1117/12.808855.
Almanza-Workman et al., "Planarization coating for polyimide substrates used in roll-to-roll fabrication of active matrix backplanes for flexible displays", HP Laboratories, HPL-2012-23, Feb. 6, 2012, 12 pgs.
Amundson et al., "Morphology and electro-optic properties of polymer-dispersed liquid-crystal films", Physical Review E, Feb. 1997, vol. 55. No. 2, pp. 1646-1654.
An et al., "Speckle suppression in laser display using several partially coherent beams", Optics Express, Jan. 5, 2009, vol. 17, No. 1, pp. 92-103, first published Dec. 22, 2008.
Apter et al., "Electrooptical Wide-Angle Beam Deflector Based on Fringing-Field-Induced Refractive Inhomogeneity in a Liquid Crystal Layer", 23rd IEEE Convention of Electrical and Electronics Engineers in Israel, Sep. 6-7, 2004, pp. 240-243.
Arnold et al., "52.3: An Improved Polarizing Beamsplitter LCOS Projection Display Based on Wire-Grid Polarizers", Society for Information Display, Jun. 2001, pp. 1282-1285.
Ayras et al., "Exit pupil expander with a large field of view based on diffractive optics", Journal of the Society for Information Display, May 18, 2009, vol. 17, No. 8, pp. 659-664, DOI: 10.1889/JSID17.8.659.
Baets et al., "Resonant-Cavity Light-Emitting Diodes: a review", Proceedings of SPIE, 2003, vol. 4996, pp. 74-86.
Bayer et al., "Introduction to Helmet-Mounted Displays", 2016, pp. 47-108.
Beckel et al., "Electro-optic properties of thiol-ene polymer stabilized ferroelectric liquid crystals", Liquid Crystals, vol. 30, No. 11, Nov. 2003, pp. 1343-1350, DOI: 10.1080/02678290310001605910.
Bergkvist, "Biospeckle-based Study of the Line Profile of Light Scattered in Strawberries", Master Thesis, Lund Reports on Atomic Physics, LRAP-220, Lund 1997, pp. 1-62.
Bernards et al., "Nanoscale porosity in polymer films: fabrication and therapeutic applications", Soft Matter, Jan. 1, 2010, vol. 6, No. 8, pp. 1621-1631, doi:10.1039/B922303G.
Bleha et al., "Binocular Holographic Waveguide Visor Display", SID Symposium Digest of Technical Papers, Holoeye Systems Inc., Jun. 2014, San Diego, CA, 4 pgs.
Bleha et al., "D-ILA Technology for High Resolution Projection Displays", Sep. 10, 2003, Proceedings, vol. 5080, 11 pgs., doi:10.1117/12.497532.
Bone, "Design Obstacles for LCOS Displays in Projection Applications "Optics architectures for LCOS are still evolving"", Aurora Systems Inc., Bay Area SID Seminar, Mar. 27, 2001, 22 pgs.
Born et al., "Optics of Crystals", Principles of Optics 5th Edition 1975, pp. 705-707.
Bourzac, "Magic Leap Needs to Engineer a Miracle", Intelligent Machines, Jun. 11, 2015, 7 pgs.
Bowen et al., "Optimisation of interdigitated electrodes for piezoelectric actuators and active fibre composites", J Electroceram, Jul. 2006, vol. 16, pp. 263-269, DOI 10.1007/s10832-006-9862-8.
Bowley et al., "Variable-wavelength switchable Bragg gratings formed in polymer-dispersed liquid crystals", Applied Physics Letters, Jul. 2, 2001, vol. 79, No. 1, pp. 9-11, DOI: 10.1063/1.1383566.
Bronnikov et al., "Polymer-Dispersed Liquid Crystals: Progress in Preparation, Investigation and Application", Journal of Macromolecular Science Part B, published online Sep. 30, 2013, vol. 52, pp. 1718-1738, DOI: 10.1080/00222348.2013.808926.
Brown, "Waveguide Displays", Rockwell Collins, 2015, 11 pgs.
Bruzzone et al., "Compact, high-brightness LED illumination for projection systems", Journal of the Society for Information Display, vol. 17, No. 12, Dec. 2009, pp. 1043-1049, DOI: 10.1189/JSID17.12.1043.
Buckley, "Colour holographic laser projection technology for heads-up and instrument cluster displays", Conference: Proc. SID Conference 14th Annual Symposium on Vehicle Displays, Jan. 2007, 5 pgs.
Buckley, "Pixtronix DMS technology for head-up displays", Pixtronix, Inc., Jan. 2011, 4 pgs.
Buckley et al., "Full colour holographic laser projector HUD", Light Blue Optics Ltd., Aug. 10, 2015, 5 pgs.
Buckley et al., "Rear-view virtual image displays", in Proc. SID Conference 16th Annual Symposium on Vehicle Displays, Jan. 2009, 5 pgs.
Bunning et al., "Effect of gel-point versus conversion on the real-time dynamics of holographic polymer-dispersed liquid crystal (HPDLC) formation", Proceedings of SPIE—vol. 5213, Liquid Crystals VII, Iam-Choon Khoo, Editor, Dec. 2003, pp. 123-129.
Bunning et al., "Electro-optical photonic crystals formed in H-PDLCs by thiol-ene photopolymerization", American Physical Society, Annual APS, Mar. 3-7, 2003, abstract #R1.135.
Bunning et al., "Holographic Polymer-Dispersed Liquid Crystals (H-PDLCs)1", Annual Review of Material Science, 2000, vol. 30, pp. 83-115.
Bunning et al., "Morphology of Anisotropic Polymer Dispersed Liquid Crystals and the Effect of Monomer Functionality", Journal of Polymer Science Part B: Polymer Physics, Jul. 30, 1997, vol. 35, pp. 2825-2833.
Busbee et al., "SiO2 Nanoparticle Sequestration via Reactive Functionalization in Holographic Polymer-Dispersed Liquid Crystals", Advanced Materials, Sep. 2009, vol. 21, pp. 3659-3662, DOI: 10.1002/adma.200900298.
Butler et al., "Diffractive Properties of Highly Birefringent Volume Gratings: Investigation", Journal of Optical Society of America, Feb. 2002, vol. 19, No. 2, pp. 183-189.
Cai et al., "Recent advances in antireflective surfaces based on nanostructure arrays", Materials Horizons, 2015, vol. 2, pp. 37-53, DOI: 10.1038/c4mh00140k.
Cameron, "Optical Waveguide Technology & Its Application In Head Mounted Displays", Proc. of SPIE, May 22, 2012, vol. 8383, pp. 83830E-1-83830E-11, doi: 10.1117/12.923660.
Caputo et al., "POLICRYPS Composite Materials: Features and Applications", Advances in Composite Materials—Analysis of Natural and Man-Made Materials, www.intechopen.com, Sep. 2011, pp. 93-118.
Caputo et al., "POLICRYPS Switchable Holographic Grating: A Promising Grating Electro-Optical Pixel for High Resolution Display Application", Journal of Display Technology, Mar. 2006, vol. 2, No. 1, pp. 38-51, DOI: 10.1109/JDT.2005.864156.
Carclo Optics, "Guide to choosing secondary optics", Carclo Optics, Dec. 15, 2014, www.carclo-optics.com, 48 pgs.

(56) References Cited

OTHER PUBLICATIONS

Chen et al., "Polarization rotators fabricated by thermally-switched liquid crystal alignments based on rubbed poly(N-vinyl carbazole) films", Optics Express, Apr. 11, 2011, vol. 19, No. 8, pp. 7553-7558, first published Apr. 5, 2011.

Cheng et al., "Design of an ultra-thin near-eye display with geometrical waveguide and freeform optics", Optics Express, Aug. 2014, 16 pgs., DOI:10.1364/OE.22.020705.

Chi et al., "Ultralow-refractive-index optical thin films through nanoscale etching of ordered mesoporous silica films", Optic Letters, May 1, 2012, vol. 37, No. 9, pp. 1406-1408, first published Apr. 19, 2012.

Chigrinov et al., "Photo-aligning by azo-dyes: Physics and applications", Liquid Crystals Today, Sep. 6, 2006, http://www.tandfonline.com/action/journalInformation?journalCode=tlcy20, 15 pgs.

Cho et al., "Electro-optic Properties of CO2 Fixed Polymer/Nematic LC Composite Films", Journal of Applied Polymer Science, Nov. 5, 2000, vol. 81, Issue 11, pp. 2744-2753.

Cho et al., "Optimization of Holographic Polymer Dispersed Liquid Crystals for Ternary Monomers", Polymer International, Nov. 1999, vol. 48, pp. 1085-1090.

Colegrove et al., "P-59: Technology of Stacking HPDLC for Higher Reflectance", SID 00 Digest, May 2000, pp. 770-773.

Cruz-Arreola et al., "Diffraction of beams by infinite or finite amplitude-phase gratings", Investigacio' N Revista Mexicana De Fi'Sica, Feb. 2011, vol. 57, No. 1, pp. 6-16.

Dainty, "Some statistical properties of random speckle patterns in coherent and partially coherent illumination", Optica Acta, Mar. 12, 1970, vol. 17, No. 10, pp. 761-772.

Date, "Alignment Control in Holographic Polymer Dispersed Liquid Crystal", Journal of Photopolymer Science and Technology, Nov. 2, 2000, vol. 13, No. 2, pp. 289-294.

Date et al., "52.3: Direct-viewing Display Using Alignment-controlled PDLC and Holographic PDLC", Society for Information Display Digest, May 2000, pp. 1184-1187, DOI: 10.1889/1.1832877.

Date et al., "Full-color reflective display device using holographically fabricated polymer-dispersed liquid crystal (HPDLC)", Journal of the SID, 1999, vol. 7, No. 1, pp. 17-22.

De Bitetto, "White light viewing of surface holograms by simple dispersion compensation", Applied Physics Letters, Dec. 15, 1966, vol. 9, No. 12, pp. 417-418.

Developer World, "Create customized augmented reality solutions", printed Oct. 19, 2017, LMX-001 holographic waveguide display, Sony Developer World, 3 pgs.

Dhar et al., "Recording media that exhibit high dynamic range for digital holographic data storage", Optics Letters, Apr. 1, 1999, vol. 24, No. 7, pp. 487-489.

Domash et al., "Applications of switchable Polaroid holograms", SPIE Proceedings, vol. 2152, Diffractive and Holographic Optics Technology, Jan. 23-29, 1994, Los Angeles, CA, pp. 127-138, ISBN: 0-8194-1447-6.

Drake et al., "Waveguide Hologram Fingerprint Entry Device", Optical Engineering, Sep. 1996, vol. 35, No. 9, pp. 2499-2505.

Drevensek-Olenik et al., "In-Plane Switching of Holographic Polymer-Dispersed Liquid Crystal Transmission Gratings", Mol. Cryst. Liq. Cryst., 2008, vol. 495, pp. 177/[529]-185/[537], DOI: 10.1080/15421400802432584.

Drevensek-Olenik et al., "Optical diffraction gratings from polymer-dispersed liquid crystals switched by interdigitated electrodes", Journal of Applied Physics, Dec. 1, 2004, vol. 96, No. 11, pp. 6207-6212, DOI: 10.1063/1.1807027.

Ducharme, "Microlens diffusers for efficient laser speckle generation", Optics Express, Oct. 29, 2007, vol. 15, No. 22, pp. 14573-14579.

Duong et al., "Centrifugal Deposition of Iron Oxide Magnetic Nanorods for Hyperthermia Application", Journal of Thermal Engineering, Yildiz Technical University Press, Istanbul, Turkey, Apr. 2015, vol. 1, No. 2, pp. 99-103.

Fattal et al., "A multi directional backlight for a wide-angle glasses-free three-dimensional display", Nature, Mar. 21, 2012, vol. 495, pp. 348-351.

Fontecchio et al., "Spatially Pixelated Reflective Arrays from Holographic Polymer Dispersed Liquid Crystals", SID 00 Digest, May 2000, pp. 774-776.

Forman et al., "Materials development for PhotoINhibited Super-Resolution (PINSR) lithography", Proc. of SPIE, 2012, vol. 8249, pp. 824904-1-24904-9, doi: 10.1117/12.908512.

Forman et al., "Radical diffusion limits to photoinhibited super-resolution lithography", Phys.Chem. Chem. Phys., May 31, 2013, vol. 15, pp. 14862-14867, DOI: 10.1039/c3cp51512.

Friedrich-Schiller, "Spatial Noise and Speckle", Version 1.12.2011, Dec. 2011, Abbe School of Photonics, Jena, Germany, 27 pgs.

Fujii et al., "Nanoparticle-polymer-composite volume gratings incorporating chain-transfer agents for holography and slow-neutron optics", Optics Letters, Apr. 25, 2014, vol. 39, Issue 12, 5 pgs.

Funayama et al., "Proposal of a new type thin film light-waveguide display device using", The International Conference on Electrical Engineering, 2008, No. P-044, 5 pgs.

Gabor, "Laser Speckle and its Elimination", BM Research and Development, Eliminating Speckle Noise, Sep. 1970, vol. 14, No. 5, pp. 509-514.

Gardiner et al., "Bistable liquid-crystals reduce power consumption for high-efficiency smart glazing", SPIE, 2009, 10.1117/2.1200904.1596, 2 pgs.

Giancola, "Holographic Diffuser, Makes Light Work of Screen Tests", Photonics Spectra, 1996, vol. 30, No. 8, pp. 121-122.

Goodman, "Some fundamental properties of speckle", J. Opt. Soc. Am., Nov. 1976, vol. 66, No. 11, pp. 1145-1150.

Goodman, "Statistical Properties of Laser Speckle Patterns", Applied Physics, 1975, vol. 9, Chapter 2, Laser Speckle and Related Phenomena, pp. 9-75.

Goodman et al., "Speckle Reduction by a Moving Diffuser in Laser Projection Displays", The Optical Society of America, 2000, 15 pgs.

Guldin et al., "Self-Cleaning Antireflective Optical Coatings", Nano Letters, Oct. 14, 2013, vol. 13, pp. 5329-5335.

Guo et al., "Review Article: A Review of the Optimisation of Photopolymer Materials for Holographic Data Storage", Physics Research International, vol. 2012, Article ID 803439, Academic Editor: Sergi Gallego, 16 pages, http://dx.doi.org/10.1155/2012/803439, May 4, 2012.

Han et al., "Study of Holographic Waveguide Display System", Advanced Photonics for Communications, 2014, 4 pgs.

Harbers et al., "I-15.3: LED Backlighting for LCD-HDTV", Journal of the Society for Information Display, 2002, vol. 10, No. 4, pp. 347-350.

Harbers et al., "Performance of High Power LED Illuminators in Color Sequential Projection Displays", Lumileds Lighting, 2007, 4 pgs.

Harbers et al., "Performance of High Power LED Illuminators in Color Sequential Projection Displays", Lumileds, Aug. 7, 2001, 11 pgs.

Harbers et al., "Performance of High-Power LED illuminators in Projection Displays", Proc. Int. Disp. Workshops, Japan. vol. 10, pp. 1585-1588, 2003.

Harding et al., "Reactive Liquid Crystal Materials for Optically Anisotropic Patterned Retarders", Merck, licrivue, 2008, ME-GR-RH-08-010, 20 pgs.

Harding et al., "Reactive Liquid Crystal Materials for Optically Anisotropic Patterned Retarders", SPIE Lithography Asia—Taiwan, 2008, Proceedings vol. 7140, Lithography Asia 2008; 71402J, doi: 10.1117/12.805378.

Hariharan, "Optical Holography: Principles, techniques and applications", Cambridge University Press, 1996, pp. 231-233.

Harris, "Photonic Devices", EE 216 Principals and Models of Semiconductor Devices, Autumn 2002, 20 pgs.

Harrold et al., "3D Display Systems Hardware Research at Sharp Laboratories of Europe: an update", Sharp Laboratories of Europe, Ltd., 7 pgs.

Harthong et al., "Speckle phase averaging in high-resolution color holography", J. Opt. Soc. Am. A, Feb. 1997, vol. 14, No. 2, pp. 405-409.

(56) References Cited

OTHER PUBLICATIONS

Hasan et al., "Tunable-focus lens for adaptive eyeglasses", Optics Express, Jan. 23, 2017, vol. 25, No. 2, 1221, 13 pgs.
Hasman et al., "Diffractive Optics: Design, Realization, and Applications", Fiber and Integrated Optics, vol. 16, pp. 1-25, 1997.
Hata et al., "Holographic nanoparticle-polymer composites based on step-growth thiol-ene photopolymerization", Optical Materials Express, Jun. 1, 2011, vol. 1, No. 2, pp. 207-222.
He et al., "Dynamics of peristrophic multiplexing in holographic polymer-dispersed liquid crystal", Liquid Crystals, Mar. 26, 2014, vol. 41, No. 5, pp. 673-684.
He et al., "Holographic 3D display based on polymer-dispersed liquid-crystal thin films", Proceedings of China Display/Asia Display 2011, pp. 158-160.
He et al., "Properties of Volume Holograms Recording in Photopolymer Films with Various Pulse Exposures Repetition Frequencies", Proceedings of SPIE vol. 5636, Bellingham, WA, 2005, doi: 10.1117/12.580978, pp. 842-848.
Herman et al., "Production and Uses of Diffractionless Beams", J. Opt. Soc. Am. A., Jun. 1991, vol. 8, No. 6, pp. 932-942.
Hisano, "Alignment layer-free molecular ordering induced by masked photopolymerization with nonpolarized light", Appl. Phys. Express 9, Jun. 6, 2016, pp. 072601-1-072601-4.
Hoepfner et al., "LED Front Projection Goes Mainstream", Luminus Devices, Inc., Projection Summit, 2008, 18 pgs.
Holmes et al., "Controlling the Anisotropy of Holographic Polymer-Dispersed Liquid-Crystal Gratings", Physical Review E, Jun. 11, 2002, vol. 65, 066603-1-066603-4.
Hoyle et al., "Advances in the Polymerization of Thiol-Ene Formulations", Heraeus Noblelight Fusion UV Inc., 2003 Conference, 6 pgs.
Hua, "Sunglass-like displays become a reality with free-form optical technology", Illumination & Displays 3D Visualization and Imaging Systems Laboratory (3DVIS) College of Optical Sciences University of Arizona Tucson, AZ. 2014, 3 pgs.
Huang et al., "Diffraction properties of substrate guided-wave holograms", Optical Engineering, Oct. 1995, vol. 34, No. 10, pp. 2891-2899.
Huang et al., "Theory and characteristics of holographic polymer dispersed Tiquid crystal transmission grating with scaffolding morphology", Applied Optics, Jun. 20, 2012, vol. 51, No. 18, pp. 4013-4020.
Iannacchione et al., "Deuterium NMR and morphology study of copolymer-dispersed liquid-crystal Bragg gratings", Europhysics Letters, 1996, vol. 36, No. 6, pp. 425-430.
Jeng et al., "Aligning liquid crystal molecules", SPIE, 2012, 10.1117/2.1201203.004148, 2 pgs.
Jo et al., "Control of Liquid Crystal Pretilt Angle using Polymerization of Reactive Mesogen", IMID 2009 Digest, P1-25, 2009, pp. 604-606.
Juhl, "Interference Lithography for Optical Devices and Coatings", Dissertation, University of Illinois at Urbana-Champaign, 2010.
Juhl et al., "Holographically Directed Assembly of Polymer Nanocomposites", ACS Nano, Oct. 7, 2010, vol. 4, No. 10, pp. 5953-5961.
Jurbergs et al., "New recording materials for the holographic industry", Proc. of SPIE, 2009 vol. 7233, pp. 72330K-1-72330L-10, doi: 10.1117/12.809579.
Kahn et al., "Private Line Report on Large Area Display", Kahn International, Jan. 7, 2003, vol. 8, No. 10, 9 pgs.
Karasawa et al., "Effects of Material Systems on the Polarization Behavior of Holographic Polymer Dispersed Liquid Crystal Gratings", Japanese Journal of Applied Physics, Oct. 1997, vol. 36, No. 10, pp. 6388-6392.
Karp et al., "Planar micro-optic solar concentration using multiple imaging lenses into a common slab waveguide", Proc. of SPIE vol. 7407, 2009 SPIE, pp. 74070D-1-74070D-11, CCC code: 0277-786X/09, doi: 10.1117/12.826531.
Karp et al., "Planar micro-optic solar concentrator", Optics Express, Jan. 18, 2010, vol. 18, No. 2, pp. 1122-1133.

Kato et al., "Alignment-Controlled Holographic Polymer Dispersed Liquid Crystal (HPDLC) for Reflective Display Devices", SPIE,1998, vol. 3297, pp. 52-57.
Kessler, "Optics of Near to Eye Displays (NEDs)", Oasis 2013, Tel Aviv, Feb. 19, 2013, 37 pgs.
Keuper et al., "26.1: RGB LED Illuminator for Pocket-Sized Projectors", SID 04 DIGEST, 2004, ISSN/0004-0966X/04/3502, pp. 943-945.
Keuper et al., "P-126: Ultra-Compact LED based Image Projector for Portable Applications", SID 03 Digest, 2003, ISSN/0003-0966X/03/3401-0713, pp. 713-715.
Kim et al., "Effect of Polymer Structure on the Morphology and Electro optic Properties of UV Curable PNLCs", Polymer, Feb. 2000, vol. 41, pp. 1325-1335.
Kim et al., "Enhancement of electro-optical properties in holographic polymer-dispersed liquid crystal films by incorporation of multiwalled carbon nanotubes into a polyurethane acrylate matrix", Polym. Int., Jun. 16, 2010, vol. 59, pp. 1289-1295.
Kim et al., "Fabrication of Reflective Holographic PDLC for Blue", Molecular Crystals and Liquid Crystals Science, 2001, vol. 368, pp. 3845-3853.
Kim et al., "Optimization of Holographic PDLC for Green", Mol. Cryst. Liq. Cryst., vol. 368, pp. 3855-3864, 2001.
Klein, "Optical Efficiency for Different Liquid Crystal Colour Displays", Digital Media Department, HPL-2000-83, Jun. 29, 2000, 18 pgs.
Kogelnik, "Coupled Wave Theory for Thick Hologram Gratings", The Bell System Technical Journal, vol. 48, No. 9, pp. 2909-2945, Nov. 1969.
Kotakonda et al., "Electro-optical Switching of the Holographic Polymer-dispersed Liquid Crystal Diffraction Gratings", Journal of Optics A: Pure and Applied Optics, Jan. 1, 2009, vol. 11, No. 2, 11 pgs.
Kress et al., "Diffractive and Holographic Optics as Optical Combiners in Head Mounted Displays", UbiComp '13, Sep. 9-12, 2013, Session: Wearable Systems for Industrial Augmented Reality Applications, pp. 1479-1482.
Lauret et al., "Solving the Optics Equation for Effective LED Applications", Gaggione North America, LLFY System Design Workshop 2010, Oct. 28, 2010, 26 pgs.
Lee, "Patents Shows Widespread Augmented Reality Innovation", PatentVue, May 26, 2015, 5 pgs.
Levin et al., "A Closed Form Solution to Natural Image Matting", Illumination & Displays 3D Visualization and Imaging Systems Laboratory (3DVIS) College of Optical Sciences University of Arizona Tucson, 2014, 8 pgs.
Levola, "Diffractive optics for virtual reality displays", Journal of the SID, 2006, 14/5, pp. 467-475.
Levola et al., "Near-to-eye display with diffractive exit pupil expander having chevron design", Journal of the SID, 2008, 16/8, pp. 857-862.
Li et al., "Design and Optimization of Tapered Light Pipes", Proceedings vol. 5529, Nonimaging Optics and Efficient Illumination Systems, Sep. 29, 2004, 10 pgs., doi: 10.1117/12.559844.
Li et al., "Dual Paraboloid Reflector and Polarization Recycling Systems for Projection Display", Proceedings vol. 5002, Projection Displays IX, Mar. 28, 2003, doi: 10.1117/12.479585, 12 pgs.
Li et al., "Light Pipe Based Optical Train and its Applications", Proceedings vol. 5524, Novel Optical Systems Design and Optimization VII, Oct. 24, 2004, doi: 10.1117/12.559833, 10 pgs.
Li et al., "Novel Projection Engine with Dual Paraboloid Reflector and Polarization Recovery Systems", Wavien Inc., SPIE EI 5289-38, Jan. 21, 2004, 49 pgs.
Li et al., "Polymer crystallization/melting induced thermal switching in a series of holographically patterned Bragg reflectors", Soft Matter, Jul. 11, 2005, vol. 1, pp. 238-242.
Lin et al., "Ionic Liquids in Photopolymerizable Holographic Materials", in book: Holograms—Recording Materials and Applications, Nov. 9, 2011, 21 pgs.
Liu et al., "Holographic Polymer Dispersed Liquid Crystals Materials, Formation and Applications", Advances in OptoElectronics, Nov. 30, 2008, vol. 2008, Article ID 684349, 52 pgs.

(56) References Cited

OTHER PUBLICATIONS

Lorek, "Experts Say Mass Adoption of augmented and Virtual Reality is Many Years Away", Siliconhills, Sep. 9, 2017, 4 pgs.
Lowenthal et al., "Speckle Removal by a Slowly Moving Diffuser Associated with a Motionless Diffuser", Journal of the Optical Society of America, Jul. 1971, vol. 61, No. 7, pp. 847-851.
Lu et al., "Polarization switch using thick holographic polymer-dispersed liquid crystal grating", Journal of Applied Physics, Feb. 1, 2004, vol. 95, No. 3, pp. 810-815.
Lu et al., "The Mechanism of electric-field-induced segregation of additives in a liquid-crystal host", Phys Rev E Stat Nonlin Soft Matter Phys., Nov. 27, 2012, 14 pgs.
Ma et al., "Holographic Reversed-Mode Polymer-Stabilized Liquid Crystal Grating", Chinese Phys. Lett., 2005, vol. 22, No. 1, pp. 103-106.
Mach et al., "Switchable Bragg diffraction from liquid crystal in colloid-templated structures", Europhysics Letters, Jun. 1, 2002, vol. 58, No. 5, pp. 679-685.
Magarinos et al., "Wide Angle Color Holographic infinity optics display", Air Force Systems Command, Brooks Air Force Base, Texas, AFHRL-TR-80-53, Mar. 1981, 100 pgs.
Marino et al., "Dynamical Behaviour of Policryps Gratings", Electronic-Liquid Crystal Communications, Feb. 5, 2004, 10 pgs.
Massenot et al., "Multiplexed holographic transmission gratings recorded in holographic polymer-dispersed liquid crystals: static and dynamic studies", Applied Optics, 2005, vol. 44, Issue 25, pp. 5273-5280.
Matay et al., "Planarization of Microelectronic Structures by Using Polyimides", Journal of Electrical Engineering, 2002, vol. 53, No. 3-4, pp. 86-90.
Mathews, "The LED FAQ Pages", Jan. 31, 2002, 23 pgs.
Matic, "Blazed phase liquid crystal beam steering", Proc. of the SPIE, 1994, vol. 2120, pp. 194-205.
McLeod, "Axicons and Their Uses", Journal of the Optical Society of America, Feb. 1960, vol. 50, No. 2, pp. 166-169.
McManamon et al., "A Review of Phased Array Steering for Narrow-Band Electrooptical Systems", Proceedings of the IEEE, Jun. 2009, vol. 97, No. 6, pp. 1078-1096.
McManamon et al., "Optical Phased Array Technology", Proceedings of the IEEE, Feb. 1996, vol. 84, Issue 2, pp. 268-298.
Miller, "Coupled Wave Theory and Waveguide Applications", The Bell System Technical Journal, Short Hills, NJ, Feb. 2, 1954, 166 pgs.
Nair et al., "Enhanced Two-Stage Reactive Polymer Network Forming Systems", Polymer (Guildf). May 25, 2012, vol. 53, No. 12, pp. 2429-2434, doi:10.1016/j.polymer.2012.04.007.
Nair et al., "Two-Stage Reactive Polymer Network Forming Systems", Advanced Functional Materials, 2012, pp. 1-9, DOI: 10.1002/adfm.201102742.
Naqvi et al., "Concentration-dependent toxicity of iron oxide nanoparticles mediated by increased oxidative stress", International Journal of Nanomedicine, Dovepress, Nov. 13, 2010, vol. 5, pp. 983-989.
Natarajan et al., "Electro Optical Switching Characteristics of Volume Holograms in Polymer Dispersed Liquid Crystals", Journal of Nonlinear Optical Physics and Materials, 1997, vol. 5, No. 1, pp. 666-668.
Natarajan et al., "Holographic polymer dispersed liquid crystal reflection gratings formed by visible light initiated thiol-ene photopolymerization", Polymer, vol. 47, May 8, 2006, pp. 4411-4420.
Naydenova et al., "Low-scattering Volume Holographic Material", DIT PhD Project, http://www.dit.ie/ieo/, Oct. 2017, 2 pgs.
Neipp et al., "Non-local polymerization driven diffusion based model: general dependence of the polymerization rate to the exposure intensity", Optics Express, Aug. 11, 2003, vol. 11, No. 16, pp. 1876-1886.
Nishikawa et al., "Mechanically and Light Induced Anchoring of Liquid Crystal on Polyimide Film", Mol. Cryst. Liq. Cryst., Aug. 1999, vol. 329, 8 pgs.
Nishikawa et al., "Mechanism of Unidirectional Liquid-Crystal Alignment on Polyimides with Linearly Polarized Ultraviolet Light Exposure", Applied Physics Letters, May 11, 1998, vol. 72, No. 19, 4 pgs.
Oh et al., "Achromatic diffraction from polarization gratings with high efficiency", Optic Letters, Oct. 15, 2008, vol. 33, No. 20, pp. 2287-2289.
Olson et al., "Templating Nanoporous Polymers with Ordered Block Copolymers", Chemistry of Materials, Web publication Nov. 27, 2007, vol. 20, pp. 869-890.
Ondax, Inc., "Volume Holographic Gratings (VHG)", 2005, 7 pgs.
Orcutt, "Coming Soon: Smart Glasses That Look Like Regular Spectacles", Intelligent Machines, Jan. 9, 2014, 4 pgs.
Osredkar, "A study of the limits of spin-on-glass planarization process", Informacije MIDEM, 2001, vol. 31, 2, ISSN0352-9045, pp. 102-105.
Osredkar et al., "Planarization methods in IC fabrication technologies", Informacije MIDEM, 2002, vol. 32, 3, ISSN0352-9045, 5 pgs.
Ou et al., "A Simple LCOS Optical System (Late News)", Industrial Technology Research Institute/OES Lab. Q100/Q200, SID 2002, Boston, USA, 2 pgs.
Paolini et al., "High-Power LED Illuminators in Projection Displays", Lumileds, Aug. 7, 2001, 19 pgs.
Park et al., "Aligned Single-Wall Carbon Nanotube Polymer Composites Using an Electric Field", Journal of Polymer Science: Part B: Polymer Physics, Mar. 24, 2006, DOI 10.1002/polb.20823, pp. 1751-1762.
Park et al., "Fabrication of Reflective Holographic Gratings with Polyurethane Acrylates (PUA)", Current Applied Physics, Jun. 2002, vol. 2, pp. 249-252.
Plawsky et al., "Engineered nanoporous and nanostructured films", MaterialsToday, Jun. 2009, vol. 12, No. 6, pp. 36-45.
Potenza, "These smart glasses automatically focus on what you're looking at", The Verge, Voc Media, Inc., Jan. 29, 2017, https://www.theverge.com/2017/1/29/14403924/smart-glasses-automatic-focus-presbyopia-ces-2017, 6 pgs.
Presnyakov et al., "Electrically tunable polymer stabilized liquid-crystal lens", Journal of Applied Physics, Apr. 29, 2005, vol. 97, pp. 103101-1-103101-6.
Qi et al., "P-111: Reflective Display Based on Total Internal Reflection and Grating-Grating Coupling", Society for Information Display Digest, May 2003, pp. 648-651, DOI: 10.1889/1.1832359.
Ramón, "Formation of 3D micro- and nanostructures using liquid crystals as a template", Technische Universiteit Eindhoven, Apr. 17, 2008, Thesis, DOI:http://dx.doi.org/10.6100/IR634422, 117 pgs.
Ramsey, "Holographic Patterning of Polymer Dispersed Liquid Crystal Materials for Diffractive Optical Elements", Thesis, The University of Texas at Arlington, Dec. 2006, 166 pgs.
Ramsey et al., "Holographically recorded reverse-mode transmission gratings in polymer-dispersed liquid crystal cells", Applied Physics B: Laser and Optics, Sep. 10, 2008, vol. 93, Nos. 2-3, pp. 481-489.
Reid, "Thin film silica nanocomposites for anti-reflection coatings", Oxford Advance Surfaces, www.oxfordsurfaces.com, Oct. 18, 2012, 23 pgs.
Riechert, "Speckle Reduction in Projection Systems", Dissertation, University Karlsruhe, 2009, 178 pgs.
Rossi et al., "Diffractive Optical Elements for Passive Infrared Detectors", Submitted to OSA Topical Meeting "Diffractive Optics and Micro-Optics", Quebec, Jun. 18-22, 2000, 3 pgs.
Sagan et al., "Electrically Switchable Bragg Grating Technology for Projection Displays", Proc. SPIE. vol. 4294, Jan. 24, 2001, pp. 75-83.
Saleh et al., "Fourier Optics: 4.1 Propagation of light in free space, 4.2 Optical Fourier Transform, 4.3 Diffraction of Light, 4.4 Image Formation, 4.5 Holography", Fundamentals of Photonics 1991, Chapter 4, pp. 108-143.
Saraswat, "Deposition & Planarization", EE 311 Notes, Aug. 29, 2017, 28 pgs.
Schreiber et al., "Laser display with single-mirror MEMS scanner", Journal of the SID 17/7, 2009, pp. 591-595.

(56) References Cited

OTHER PUBLICATIONS

Seiberle et al., "Photo-aligned anisotropic optical thin films", Journal of the SID 12/1, 2004, 6 pgs.
Serebriakov et al., "Correction of the phase retardation caused by intrinsic birefringence in deep UV lithography", Proc. of SPIE, May 21, 2010, vol. 5754, pp. 1780-1791.
Shi et al., "Design considerations for high efficiency liquid crystal decentered microlens arrays for steering light", Applied Optics, vol. 49, No. 3, Jan. 20, 2010, pp. 409-421.
Shriyan et al., "Analysis of effects of oxidized multiwalled carbon nanotubes on electro-optic polymer/liquid crystal thin film gratings", Optics Express, Nov. 12, 2010, vol. 18, No. 24, pp. 24842-24852.
Simonite, "How Magic Leap's Augmented Reality Works", Intelligent Machines, Oct. 23, 2014, 7 pgs.
Smith et al., "RM-PLUS—Overview", Licrivue, Nov. 5, 2013, 16 pgs.
Sony Global, "Sony Releases the Transparent Lens Eyewear 'SmartEyeglass Developer Edition'", printed Oct. 19, 2017, Sony Global—News Releases, 5 pgs.
Steranka et al., "High-Power LEDs—Technology Status and Market Applications", Lumileds, Jul. 2002, 23 pgs.
Stumpe et al., "Active and Passive LC Based Polarization Elements", Mol. Cryst. Liq. Cryst., 2014, vol. 594: pp. 140-149.
Stumpe et al., "New type of polymer-LC electrically switchable diffractive devices—POLIPHEM", May 19, 2015, p. 97.
Subbarayappa et al., "Bistable Nematic Liquid Crystal Device", Jul. 30, 2009, 14 pgs.
Sun et al., "Effects of multiwalled carbon nanotube on holographic polymer dispersed liquid crystal", Polymers Advanced Technologies, Feb. 19, 2010, DOI: 10.1002/pat.1708, 8 pgs.
Sun et al., "Low-birefringence lens design for polarization sensitive optical systems", Proceedings of SPIE, 2006, vol. 6289, pp. 6289DH-1-6289DH-10, doi: 10.1117/12.679416.
Sun et al., "Transflective multiplexing of holographic polymer dispersed liquid crystal using Si additives", eXPRESS Polymer Letters, 2011, vol. 5, No. 1, pp. 73-81.
Sutherland et al., "Bragg Gratings in an Acrylate Polymer Consisting of Periodic Polymer—Dispersed Liquid-Crystal Planes", Chem. Mater., 1993, vol. 5, pp. 1533-1538.
Sutherland et al., "Electrically switchable volume gratings in polymer-dispersed liquid crystals", Applied Physics Letters, Feb. 28, 1994, vol. 64, No. 9, pp. 1074-1076.
Sutherland et al., "Enhancing the electro-optical properties of liquid crystal nanodroplets for switchable Bragg gratings", Proc. of SPIE, 2008, vol. 7050, pp. 705003-1-705003-9, doi: 10.1117/12.792629.
Sutherland et al., "The physics of photopolymer liquid crystal composite holographic gratings", presented at SPIE: Diffractive and Holographic Optics Technology San Jose, CA, 1996, SPIE, vol. 2689, pp. 158-169.
Sweatt, "Achromatic triplet using holographic optical elements", Applied Optics, May 1977, vol. 16, No. 5, pp. 1390-1391.
Talukdar, "Technology Forecast: Augmented reality", Changing the economics of Smartglasses, Issue 2, 2016, 5 pgs.
Tao et al., "TiO2 nanocomposites with high refractive index and transparency", J. Mater. Chem., Oct. 4, 2011, vol. 21, pp. 18623-18629.
Titus et al., "Efficient, Accurate Liquid Crystal Digital Light Deflector", Proc. SPIE 3633, Diffractive and Holographic Technologies, Systems, and Spatial Light Modulators VI, 1 Jun. 1, 1999, doi: 10.1117/12.349334, 10 pgs.
Tiziani, "Physical Properties of Speckles", Speckle Metrology, Chapter 2, Academic Press, Inc., 1978, pp. 5-9.
Tominaga et al., "Fabrication of holographic polymer dispersed liquid crystals doped with gold nanoparticles", 2010 Japanese Liquid Crystal Society Annual Meeting, 2 pgs.
Tomita, "Holographic assembly of nanoparticles in photopolymers for photonic applications", The International Society for Optical Engineering, SPIE Newsroom, 2006, 3 pgs., doi: 10.1117/2.1200612.0475.
Trisnadi, "Hadamard Speckle Contrast Reduction", Optics Letters, Jan. 1, 2004, vol. 29, No. 1, pp. 11-13.
Trisnadi, "Speckle contrast reduction in laser projection displays", Proc. SPIE 4657, 2002, 7 pgs.
Tzeng et al., "Axially symmetric polarization converters based on photo-aligned liquid crystal films", Optics Express, Mar. 17, 2008, vol. 16, No. 6, pp. 3768-3775.
Upatnieks et al., "Color Holograms for white light reconstruction", Applied Physics Letters, Jun. 1, 1996, vol. 8, No. 11, pp. 286-287.
Ushenko, "The Vector Structure of Laser Biospeckle Fields and Polarization Diagnostics of Collagen Skin Structures", Laser Physics, 2000, vol. 10, No. 5, pp. 1143-1149.
Valoriani, "Mixed Reality: Dalle demo a un prodotto", Disruptive Technologies Conference, Sep. 23, 2016, 67 pgs.
Van Gerwen et al., "Nanoscaled interdigitated electrode arrays for biochemical sensors", Sensors and Actuators, Mar. 3, 1998, vol. B 49, pp. 73-80.
Vecchi, "Studi ESR Di Sistemi Complessi Basati Su Cristalli Liquidi", Thesis, University of Bologna, Department of Physical and Inorganic Chemistry, 2004-2006, 110 pgs.
Veltri et al., "Model for the photoinduced formation of diffraction gratings in liquid-crystalline composite materials", Applied Physics Letters, May 3, 2004, vol. 84, No. 18, pp. 3492-3494.
Vita, "Switchable Bragg Gratings", Thesis, Universita degli Studi di Napoli Federico II, Nov. 2005, 103 pgs.
Vuzix, "M3000 Smart Glasses, Advanced Waveguide Optics", brochure, Jan. 1, 2017, 2 pgs.
Wang et al., "Liquid-crystal blazed-grating beam deflector", Applied Optics, Dec. 10, 2000, vol. 39, No. 35, pp. 6545-6555.
Wang et al., "Optical Design of Waveguide Holographic Binocular Display for Machine Vision", Applied Mechanics and Materials, Sep. 27, 2013, vols. 427-429, pp. 763-769.
Wang et al., "Speckle reduction in laser projection systems by diffractive optical elements", Applied Optics, Apr. 1, 1998, vol. 37, No. 10, pp. 1770-1775.
Weber et al., "Giant Birefringent Optics in Multilayer Polymer Mirrors", Science, Mar. 31, 2000, vol. 287, pp. 2451-2456.
Wei An, "Industrial Applications of Speckle Techniques", Doctoral Thesis, Royal Institute of Technology, Department of Production Engineering, Chair of Industrial Metrology & Optics, Stockholm, Sweden 2002, 76 pgs.
Welde et al., "Investigation of methods for speckle contrast reduction", Master of Science in Electronics, Jul. 2010, Norwegian University of Science and Technology, Department of Electronics and Telecommunications, 127 pgs.
White, "Influence of thiol-ene polymer evolution on the formation and performance of holographic polymer dispersed liquid crystals", The 232nd ACS National Meeting, San Francisco, CA, Sep. 10-14, 2006, 1 pg.
Wight et al., "Nanoporous Films with Low Refractive Index for Large-Surface Broad-Band Anti-Reflection Coatings", Macromol. Mater. Eng., 2010, 295, DOI: 10.1002/mame.201000045, 9 pgs.
Wilderbeek et al., "Photoinitiated Bulk Polymerization of Liquid Crystalline Thiolene Monomers", Macromolecules, 2002, vol. 35, pp. 8962-8969.
Wilderbeek et al., "Photo-Initiated Polymerization of Liquid Crystalline Thiol-Ene Monomers in Isotropic and Anisotropic Solvents", J. Phys. Chem. B, 2002, vol. 106, No. 50, pp. 12874-12883.
Wofford et al., "Liquid crystal bragg gratings: dynamic optical elements for spatial light modulators", Hardened Materials Branch, Survivability and Sensor Materials Division, AFRL-ML-WP-TP-2007-551, Air Force Research Laboratory, Jan. 2007, Wright-Patterson Air Force Base, OH, 17 pgs.
Yaqoob et al., "High-speed two-dimensional laser scanner based on Bragg grating stored in photothermorefractive glass", Applied Optics, Sep. 10, 2003, vol. 42, No. 26, pp. 5251-5262.
Yaroshchuk et al., "Stabilization of liquid crystal photoaligning layers by reactive mesogens", Applied Physics Letters, Jul. 14, 2009, vol. 95, pp. 021902-1-021902-3.
Ye, "Three-dimensional Gradient Index Optics Fabricated in Diffusive Photopolymers", Thesis, Department of Electrical, Computer and Energy Engineering, University of Colorado, 2012, 224 pgs.

(56) References Cited

OTHER PUBLICATIONS

Yemtsova et al., "Determination of liquid crystal orientation in holographic polymer dispersed liquid crystals by linear and non-linear optics", Journal of Applied Physics, Oct. 13, 2008, vol. 104, pp. 073115-1-073115-4.
Yeralan et al., "Switchable Bragg grating devices for telecommunications applications", Opt. Eng., Aug. 2012, vol. 41, No. 8, pp. 1774-1779.
Yoshida et al., "Nanoparticle-Dispersed Liquid Crystals Fabricated by Sputter Doping", Adv. Mater., 2010, vol. 22, pp. 622-626.
Zhang et al., "Dynamic Holographic Gratings Recorded by Photopolymerization of Liquid Crystalline Monomers", J. Am. Chem. Soc., 1994, vol. 116, pp. 7055-7063.
Zhang et al., "Switchable Liquid Crystalline Photopolymer Media for Holography", J. Am. Chem. Soc., 1992, vol. 114, pp. 1506-1507.
Zhao et al., "Designing Nanostructures by Glancing Angle Deposition", Proc. of SPIE, Oct. 27, 2003, vol. 5219, pp. 59-73.
Zlębacz, "Dynamics of nano and micro objects in complex liquids", Ph.D. dissertation, Institute of Physical Chemistry of the Polish Academy of Sciences, Warsaw 2011, 133 pgs.
Zou et al., "Functionalized nano interdigitated electrodes arrays on polymer with integrated microfluidics for direct bio-affinity sensing using impedimetric measurement", Sensors and Actuators A, Jan. 16, 2007, vol. 136, pp. 518-526, , doi:10.1016/j.sna.2006.12.006.
Zyga, "Liquid crystals controlled by magnetic fields may lead to new optical applications", Nanotechnology, Nanophysics, Retrieved from http://phys.org/news/2014-07-liquid-crystals-magnetic-fields-optical.html, Jul. 9, 2014, 3 pgs.
International Preliminary Report on Patentability for International Application PCT/US2021/034315, Report dated Nov. 17, 2022, dated Dec. 8, 2022, 11 Pgs.

\* cited by examiner

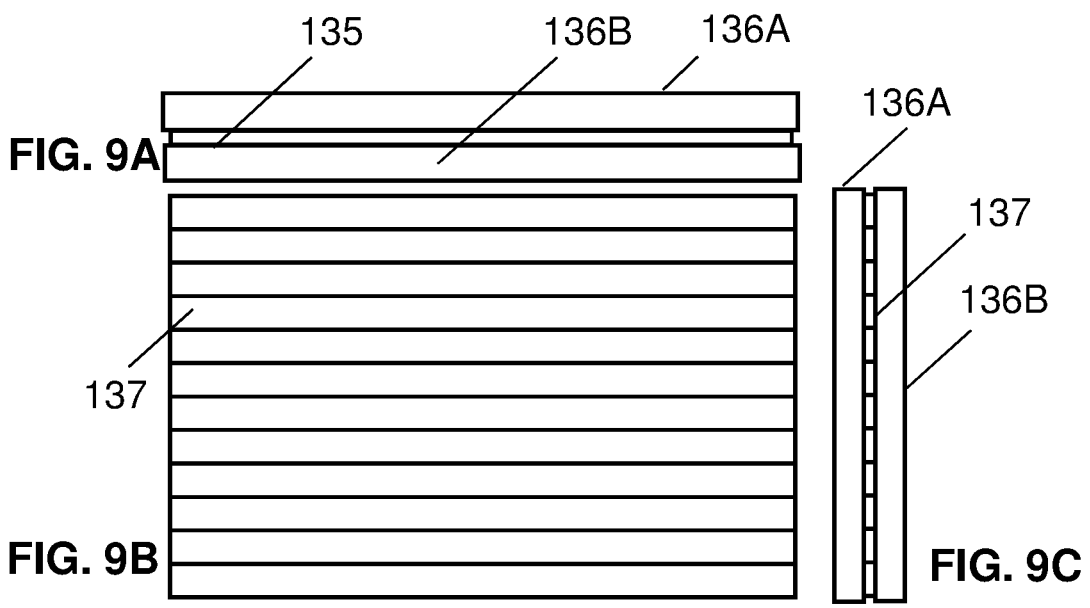
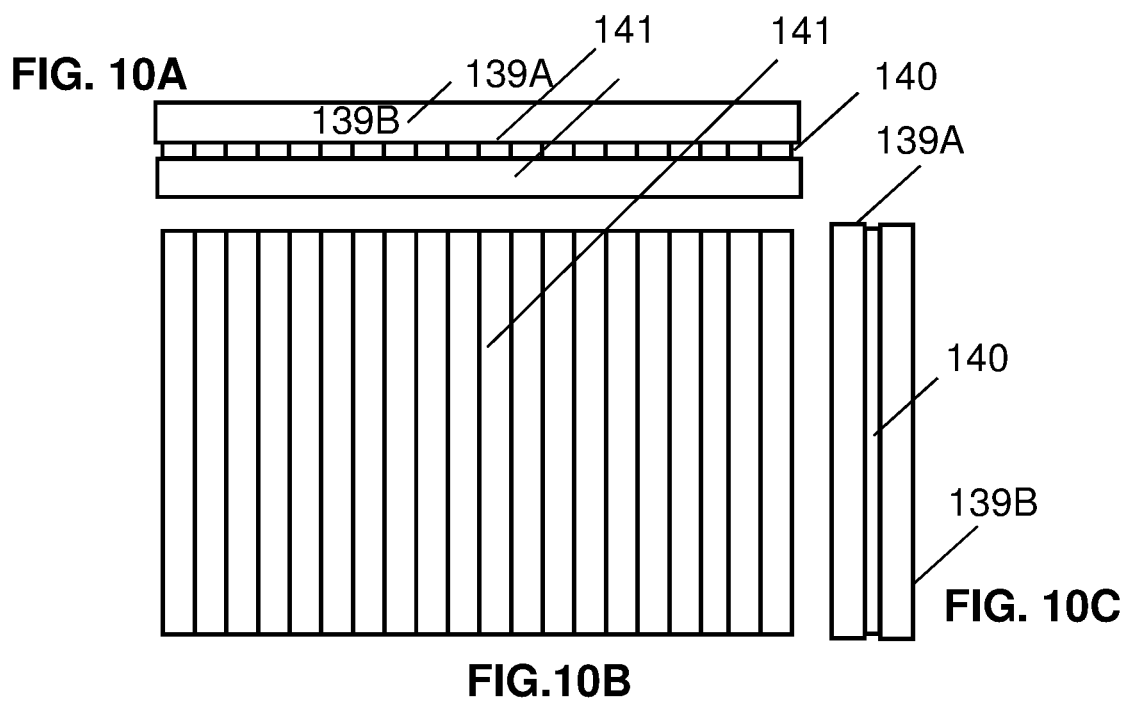

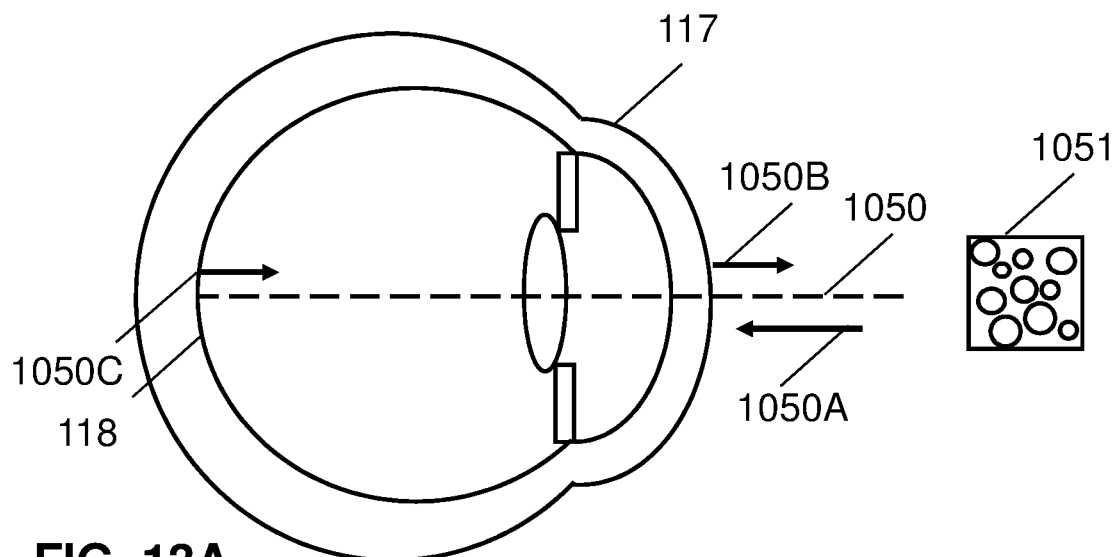
FIG. 13A
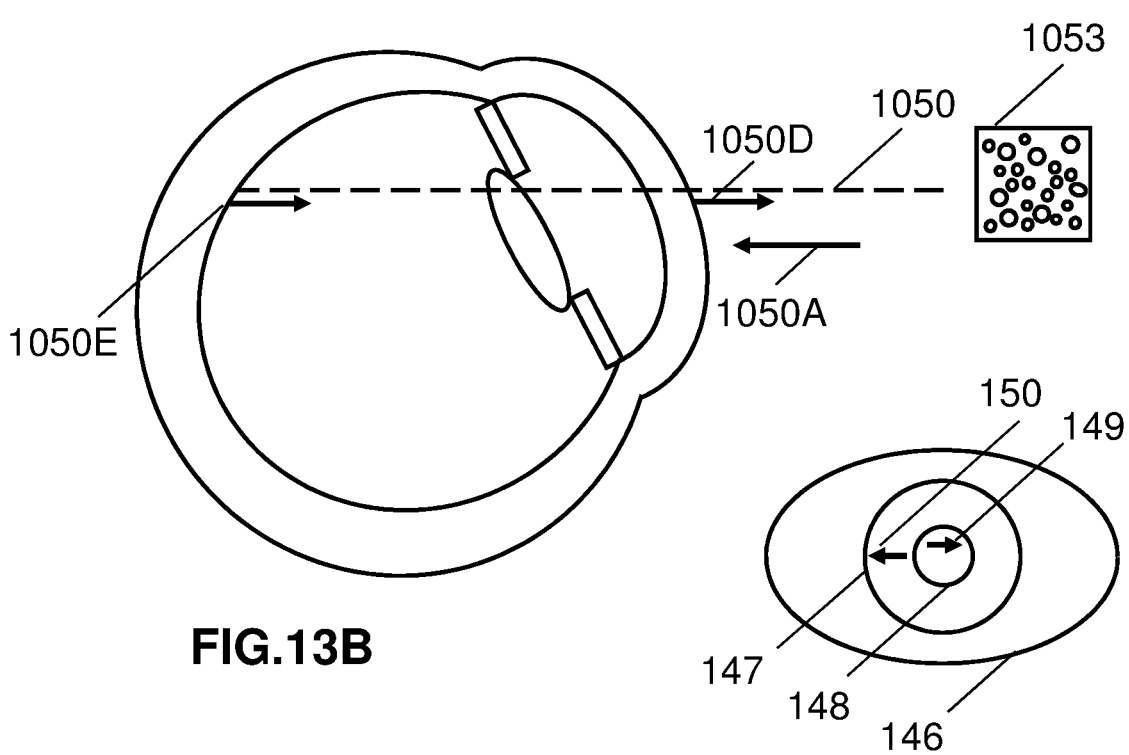
FIG.13B
FIG.14

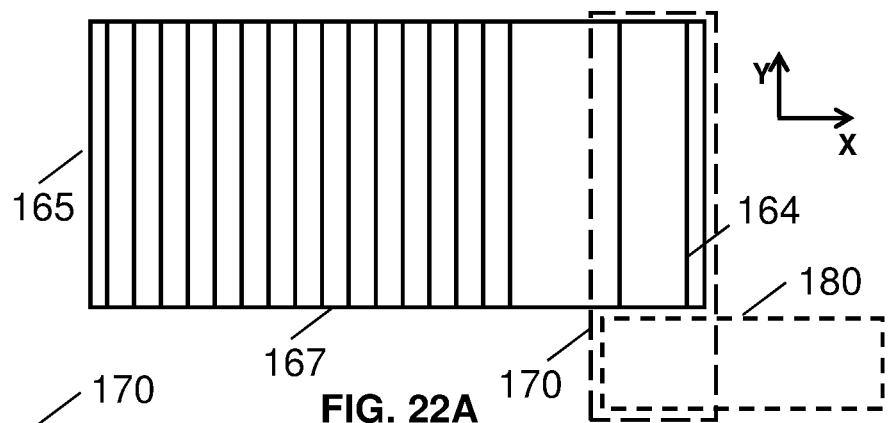
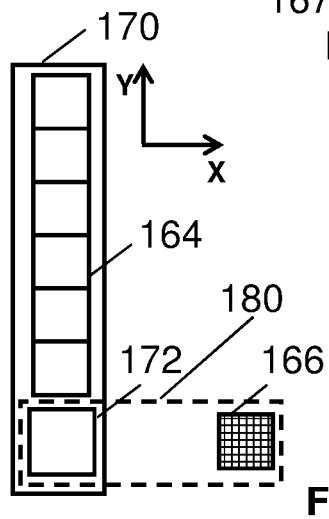
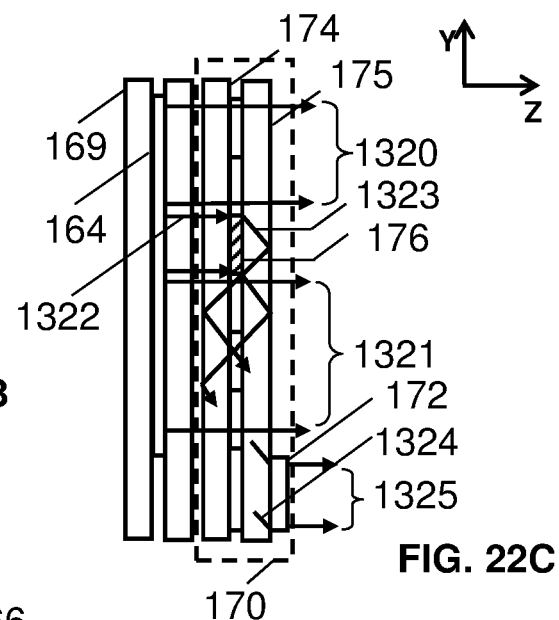
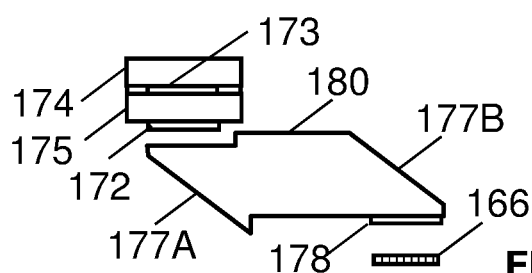
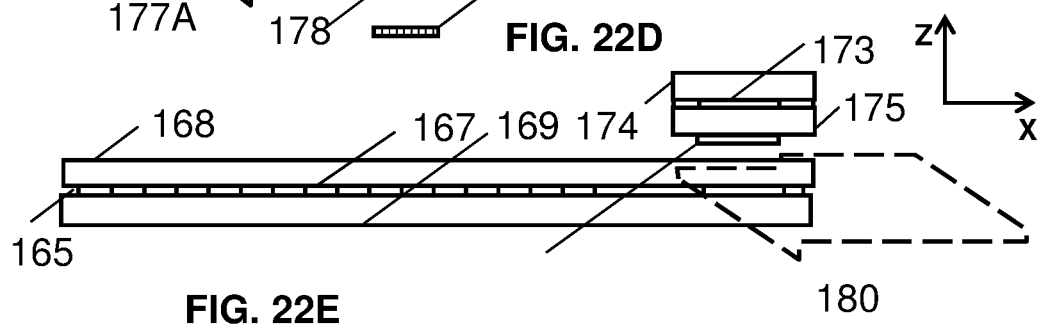
FIG. 22A
FIG. 22B
FIG. 22C
FIG. 22D
FIG. 22E

HOLOGRAPHIC WAVEGUIDE EYE TRACKER

CROSS-REFERENCE TO RELATED APPLICATIONS

This present application is a continuation of U.S. patent application Ser. No. 16/922,858, entitled "Holographic Waveguide Eye Tracker" to Popovich et al., filed Jul. 7, 2020, which is a continuation of U.S. patent application Ser. No. 16/277,390, entitled "Holographic Waveguide Eye Tracker" to Popovich et al., filed Feb. 15, 2019 and issued on Jul. 14, 2020 as U.S. Pat. No. 10,712,571, which is a continuation of U.S. patent application Ser. No. 14/903,249, entitled "Holographic Waveguide Eye Tracker" to Popovich et al., filed Jan. 6, 2016 and issued on Feb. 19, 2019 as U.S. Pat. No. 10,209,517, which is a U.S. National Phase of PCT Application No. PCT/GB2014/000197, entitled "Holographic Waveguide Eye Tracker" to Popovich et al, filed May 19, 2014, which claims the benefit of U.S. Provisional Patent Application No. 61/855,625, entitled "Apparatus for Eye Tracking" to Popovich et al., filed May 20, 2013, the disclosures of which are incorporated herein by reference in their entireties.

BACKGROUND

This invention relates to an eye tracking sensor, and more particularly to an eye tracker using electrically switchable gratings.

Eye tracking is important in Head Mounted Displays (HMDs) because it can extend the ability of the user to designate targets well beyond the head mobility limits. Eye tracking technology based on projecting IR light into the users eye and utilizing the primary Purkinje reflections and the pupil-masked retina reflection have been around since the 1980's. The method tracks the relative motion of these images in order to establish a vector characterizing the point of regard. Most eye trackers have employed flat beam splitters in front of the users' eyes and relatively large optics to image the reflections onto a sensor (generally a CCD or CMOS camera).

There is much prior art in the patent and scientific literature including the following United States filings:
1. United Stated Patent Application Publication No. US2011019874 (A1) by Levola et al entitled DEVICE AND METHOD FOR DETERMINING GAZE DIRECTION;
2. U.S. Pat. No. 5,410,376 by Cornsweet entitled Eye tracking method and apparatus;
3. U.S. Pat. No. 3,804,496 by Crane et al entitled TWO DIMENSIONAL EYE TRACKER AND METHOD FOR TRACKING AN EYE TWO DIMENSIONAL EYE TRACKER AND METHOD FOR TRACKING AN EYE;
4. U.S. Pat. No. 4,852,988 by Velez et al entitled Visor and camera providing a parallax-free field-of-view image for a head-mounted eye movement measurement system;
5. U.S. Pat. No. 7,542,210 by Chirieleison entitled EYE TRACKING HEAD MOUNTED DISPLAY;
6. United Stated Patent Application Publication No. US 2002/0167462 A1 by Lewis entitled PERSONAL DISPLAY WITH VISION TRACKING; and
7. U.S. Pat. No. 4,028,725 by Lewis entitled HIGH RESOLUTION VISION SYSTEM.

The exit pupil of these trackers is generally limited by either the size of the beamsplitter or the first lens of the imaging optics. In order to maximize the exit pupil, the imaging optics are positioned close to the beamsplitter, and represent a vision obscuration and a safety hazard. Another known limitation with eye trackers is the field of view, which is generally limited by the illumination scheme in combination with the geometry of the reflected images off the cornea. The cornea is an aspheric shape of smaller radius that the eye-ball. The cornea reflection tracks fairly well with angular motion until the reflected image falls off the edge of the cornea and onto the sclera. The need for beam splitters and refractive lenses in conventional eye trackers results in a bulky component that is difficult to integrate into a (HMD). The present invention addresses the need for a slim, wide field of view, large exit pupil, high-transparency eye tracker for HMDs.

The inventors have found that diffractive optical elements offer a route to providing compact, transparent, wide field of view eye trackers. One important class of diffractive optical elements is based on Switchable Bragg Gratings (SBGs). SBGs are fabricated by first placing a thin film of a mixture of photopolymerizable monomers and liquid crystal material between parallel glass plates. One or both glass plates support electrodes, typically transparent indium tin oxide films, for applying an electric field across the film. A volume phase grating is then recorded by illuminating the liquid material (often referred to as the syrup) with two mutually coherent laser beams, which interfere to form a slanted fringe grating structure. During the recording process, the monomers polymerize and the mixture undergoes a phase separation, creating regions densely populated by liquid crystal micro-droplets, interspersed with regions of clear polymer. The alternating liquid crystal-rich and liquid crystal-depleted regions form the fringe planes of the grating. The resulting volume phase grating can exhibit very high diffraction efficiency, which may be controlled by the magnitude of the electric field applied across the film. When an electric field is applied to the grating via transparent electrodes, the natural orientation of the LC droplets is changed causing the refractive index modulation of the fringes to reduce and the hologram diffraction efficiency to drop to very low levels. Note that the diffraction efficiency of the device can be adjusted, by means of the applied voltage, over a continuous range. The device exhibits near 100% efficiency with no voltage applied and essentially zero efficiency with a sufficiently high voltage applied. In certain types of HPDLC devices magnetic fields may be used to control the LC orientation. In certain types of HPDLC phase separation of the LC material from the polymer may be accomplished to such a degree that no discernible droplet structure results.

SBGs may be used to provide transmission or reflection gratings for free space applications. SBGs may be implemented as waveguide devices in which the HPDLC forms either the waveguide core or an evanescently coupled layer in proximity to the waveguide. In one particular configuration to be referred to here as Substrate Guided Optics (SGO) the parallel glass plates used to form the HPDLC cell provide a total internal reflection (TIR) light guiding structure. Light is "coupled" out of the SBG when the switchable grating diffracts the light at an angle beyond the TIR condition. SGOs are currently of interest in a range of display and sensor applications. Although much of the earlier work on HPDLC has been directed at reflection holograms transmission devices are proving to be much more versatile as optical system building blocks. Typically, the HPDLC used in SBGs comprise liquid crystal (LC), monomers, photoinitiator dyes, and coinitiators. The mixture frequently includes a surfactant. The patent and scientific literature contains many examples of material systems and processes that may be used to fabricate SBGs. Two fundamental patents are: U.S. Pat. No. 5,942,157 by Sutherland, and U.S. Pat. No. 5,751,452 by Tanaka et al. Both filings describe monomer and liquid crystal material combinations suitable for fabricating SBG devices.

One of the known attributes of transmission SBGs is that the LC molecules tend to align normal to the grating fringe planes. The effect of the LC molecule alignment is that transmission SBGs efficiently diffract P polarized light (ie light with the polarization vector in the plane of incidence) but have nearly zero diffraction efficiency for S polarized light (ie light with the polarization vector normal to the plane of incidence. Transmission SBGs may not be used at near-grazing incidence as the diffraction efficiency of any grating for P polarization falls to zero when the included angle between the incident and reflected light is small.

There is a requirement for a compact, lightweight eye tracker with a large field of view, and a high degree of transparency to external light.

SUMMARY

It is a first object of the invention to provide a compact, lightweight eye tracker with a large field of view, and a high degree of transparency to external light.

It is a second object of the invention to provide a compact, lightweight eye tracker with a large field of view, and a high degree of transparency to external light implemented in a thin optical waveguide.

The objects of the invention are achieved in one embodiment of the invention in which there is provided an eye tracker comprising: a first waveguide for propagating illumination light along a first waveguide path and propagating image light reflected from at least one surface of an eye along a second waveguide path; a source of the illumination light optically coupled to the waveguide and a detector optically coupled to the waveguide. At least one grating lamina for deflecting the illumination light out of the first waveguide path towards the eye and deflecting the image light into the second waveguide path towards the detector is disposed adjacent an optical surface of the waveguide. The optical surface of the waveguide is at least one of an internal surface or an external surface of the waveguide.

In one embodiment the grating lamina comprises an output grating for deflecting the illumination light out of the first waveguide path towards eye and an input grating for deflecting the image light into the second waveguide path towards the detector.

In one embodiment at least one of the input and output gratings comprises at least one switchable grating element having a diffracting state and a non diffracting state.

In one embodiment the grating lamina comprises at least one switchable grating element having a diffracting state and a non diffracting state. An element in the diffractin g state deflects illumination light out of the first waveguide path towards the eye and deflects the image light into the second waveguide path towards the detector.

In one embodiment the switchable grating elements are elongate with longer dimension aligned perpendicular to at least one of the first and second waveguide paths.

In one embodiment the first and second waveguide paths are parallel.

In one embodiment the grating lamina further comprises at least one of: an input grating for deflecting illumination light from the source into the first waveguide path; and an output grating for deflecting image light out of the second waveguide path towards the detector.

In one embodiment the grating lamina further comprises a second waveguide containing a linear array of switchable grating elements optically coupled to the detector and overlaying the output grating. Each element when in its diffracting state samples a portion of the light in the first waveguide and deflects it along the second waveguide towards the detector.

In one embodiment the grating lamina further comprises a third waveguide containing a linear array of switchable grating elements optically coupled to the light source and overlaying the input grating. Each element when in its diffracting state deflects light from the third waveguide into the first waveguide.

In one embodiment the output grating abuts an upper or lower edge of the output grating along the first waveguide path.

In one embodiment the output grating comprises upper and lower gratings disposed adjacent upper and lower edges of the output grating along the first waveguide path.

In one embodiment the input grating comprises a first array of switchable elongate beam deflection grating elements and an overlapping second array of switchable elongate beam deflection grating elements. The elements of the first and second arrays are disposed with their longer dimensions orthogonal.

In one embodiment at least one of the input and output gratings is a linear array of elongate switchable beam deflection elements with longer dimension aligned perpendicular to the first and second waveguide paths.

In one embodiment the grating lamina is one of a switchable Bragg grating, a switchable grating recorded in a reverse mode holographic polymer dispersed liquid crystal, a surface relief grating, and a non switching Bragg grating.

In one embodiment the image light has the characteristics of a speckle pattern

In one embodiment the eye surface being tracked is at least one of the cornea, lens, iris, sclera and retina.

In one embodiment the detector is a two dimensional array.

In one embodiment the at least one grating lamina encodes at least one of optical power and diffusing properties.

In one embodiment the detector is connected to an image processing apparatus for determining at least one spatio-temporal characteristic of an eye movement.

In one embodiment an eye tracker comprises: a waveguide for propagating illumination light reflected from at least one surface of an eye along a waveguide path; a source of the illumination light; a detector optically coupled to the waveguide. The waveguide contains at least one grating lamina for deflecting illumination light reflected of an eye surface into the second waveguide path towards the detector.

In one embodiment the detector is connected to an image processing apparatus for determining at least one spatio-temporal characteristic of an eye movement.

In one embodiment the image light is a Purkinje reflection.

In one embodiment the source is a laser.

In one embodiment the source is a light emitting diode.

In one embodiment the illumination grating provides collimated light.

In one embodiment the illumination grating provides divergent light.

In one embodiment the input grating encodes optical power.

In one embodiment the output grating encodes optical power.

In one embodiment at least one of the grating lamina includes at least one turning grating.

In one embodiment the eye tracker image processing system includes a neural network.

A more complete understanding of the invention can be obtained by considering the following detailed description in conjunction with the accompanying drawings, wherein like index numerals indicate like parts. For purposes of clarity, details relating to technical material that is known in the technical fields related to the invention have not been described in detail

BRIEF DESCRIPTION OF THE DRAWINGS

FIG. 9A is a schematic top elevation view of a first layer of a two layer imaging grating in one embodiment of the invention.

FIG. 9B is a schematic plan view of a first layer of a two layer imaging grating in one embodiment of the invention.

FIG. 9C is a schematic side elevation view of a first layer of a two layer imaging grating in one embodiment of the invention.

FIG. 10A is a schematic top elevation view of a second layer of a two layer imaging grating in one embodiment of the invention.

FIG. 10B is a schematic plan view of a second layer of a two layer imaging grating in one embodiment of the invention.

FIG. 10C is a schematic side elevation view of a second layer of a two layer imaging grating in one embodiment of the invention.

FIG. 13A is a schematic cross of the human eye in a first rotational state showing a typical speckle pattern formed by the cornea and retina.

FIG. 13B is a schematic cross of the human eye in a first rotational state showing a typical speckle pattern formed by the cornea and retina.

FIG. 14 is a schematic front elevation view of a human eye show showing the directions of motions of speckle patterns produced by the retina and cornea.

FIG. 22A is a schematic plan view of the imaging grating, the image sampling grating and the detector module of an eye tracker using separate illumination and imaging gratings in one embodiment of the invention.

FIG. 22B is a schematic plan view of image sampling grating and the detector module of an eye tracker using separate illumination and imaging gratings in one embodiment of the invention.

FIG. 22C is a schematic cross section view of the imaging grating and the image sampling grating of an eye tracker using separate illumination and imaging gratings in one embodiment of the invention.

FIG. 22D is a schematic cross section view of image sampling grating and the detector module of an eye tracker using separate illumination and imaging gratings in one embodiment of the invention.

FIG. 22E is a schematic cross section view of the imaging grating, the image sampling grating and the detector module of an eye tracker using separate illumination and imaging gratings in one embodiment of the invention.

DETAILED DESCRIPTION

Figure 1A:
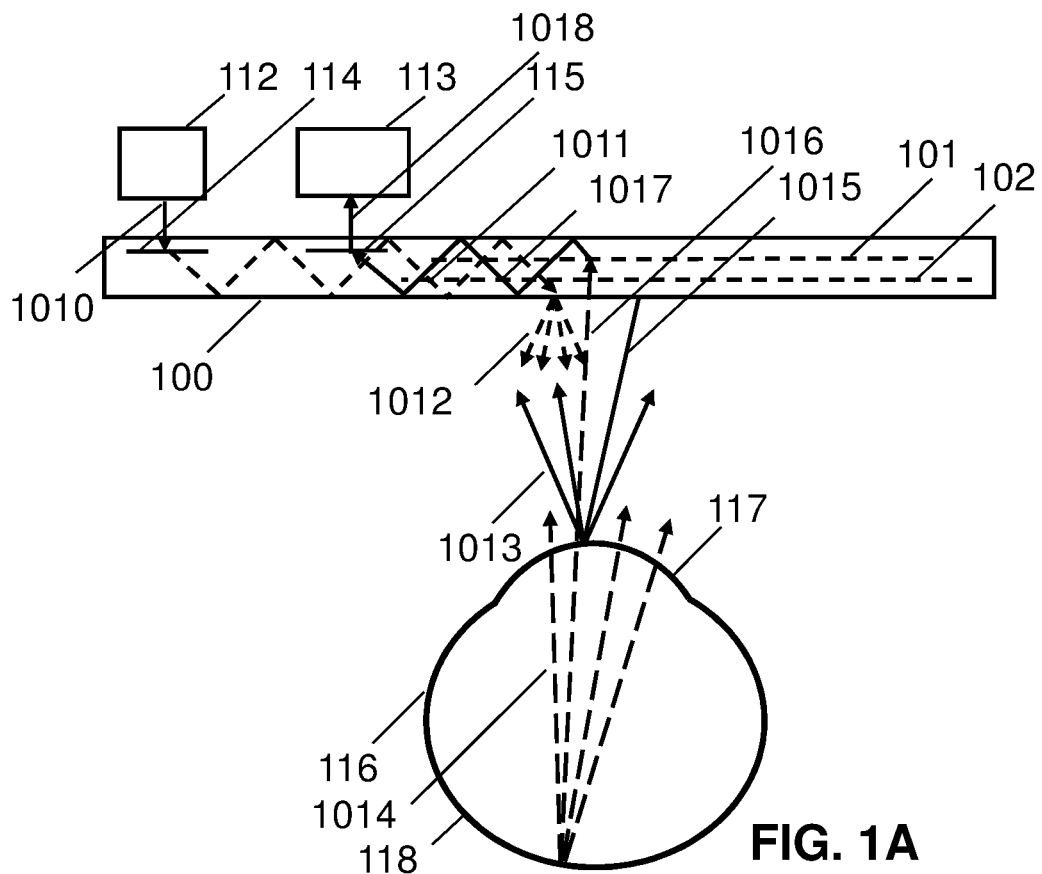
FIG. 1A is a schematic plan view of an eye tracker shown in relation to a human eye in one embodiment of the invention

The invention will now be further described by way of example only with reference to the accompanying drawings. It will apparent to those skilled in the art that the present invention may be practiced with some or all of the present invention as disclosed in the following description. For the purposes of explaining the invention well-known features of optical technology known to those skilled in the art of optical design and visual displays have been omitted or simplified in order not to obscure the basic principles of the invention. Unless otherwise stated the term "on-axis" in relation to a ray or a beam direction refers to propagation parallel to an axis normal to the surfaces of the optical components described in relation to the invention. In the following description the terms light, ray, beam and direction may be used interchangeably and in association with each other to indicate the direction of propagation of light energy along rectilinear trajectories. Parts of the following description will be presented using terminology commonly employed by those skilled in the art of optical design. It should also be noted that in the following description of the invention repeated usage of the phrase "in one embodiment" does not necessarily refer to the same embodiment.

The proposed eye tracker aims to satisfy a suite of challenging requirements. Since it will eventually be integrated into a head-worn display, it should make minimum impact on the overall optical performance. The inventors' design goals are: a field of view (FOV) of 60° horizontal ×48° vertical; 17 mm eye relief; and eye motion box/exit pupil (20 mm.×10-15 mm). Moreover, the eye tracker must satisfy eye safety requirements for near-eye visual displays with regard to weight (minimal), center of gravity (ergonomic), and profile. Furthermore it should not compromise: pixel resolution, see-through (≥90%) and power consumption (minimal).

Eye Trackers based on classical Purkinje imaging methods suffer from high latency resulting mainly from the large delay incurred by feature recognition and tracking algorithms. The inventors are strongly motivated by a desire to develop an eye tracker that firstly simplifies the image processing problems of classical eye tracking that often result in unacceptably high latency and secondly can make use of relatively unsophisticated detector technology. The proposed eye tracker avoids the cost and complexity of implementing classical Purkinje imaging methods by tracking eye signatures using low resolution high speed image sensors. Ideally the detector technology would be equivalent in specification to that used in the infrared mouse a device which is now ubiquitous and, more importantly, capable of being manufactured using sub dollar components. The signatures do not need to be images of eye features such as pupil edges but can be random structures such as speckle patterns (including reflections from multiple surfaces and scatter from the optical media inside the eye). However, it is important that whatever signature is tracked has a strong spatio-temporal variation with gaze direction.

The inventors believe that this approach offers significant advantages in terms of detector resolution, processing overhead and power consumption.

Figure 1B:
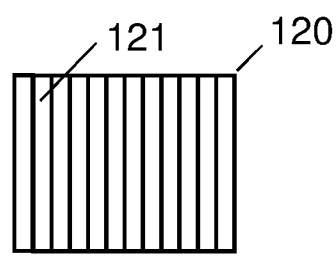
FIG. 1B is a schematic front elevation view showing elongate grating elements used in the imaging grating in one embodiment of the invention.
Figure 1C:
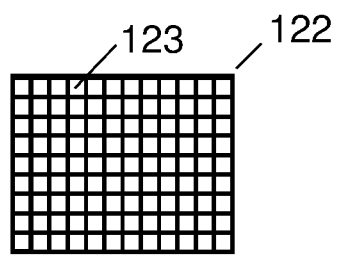
FIG. 1C is a schematic front elevation view showing a two dimensional array of grating elements used in the imaging grating in one embodiment of the invention.

An eye tracker according to the principles of the invention provides an infrared illumination channel for delivering infrared illumination to the eye and an imaging channel for forming an image of the eye at a sensor. In one embodiment of the invention illustrated in FIGS. 1-2, the eye tracker comprises a waveguide 100 for propagating illumination light towards an eye 116 and propagating image light reflected from at least one surface of an eye; a light source 112 optically coupled to the waveguide; and a detector 113 optically coupled to the waveguide. Disposed in the waveguide are: at least one input grating 114 for deflecting illumination light from the source into a first waveguide path; at least one illumination grating 102 for deflecting the illumination light towards the eye; at least one imaging grating 101 for deflecting the image light into a second waveguide path; and at least one output grating 115 for deflecting the image light towards the detector. The inventors also refer to the waveguide 100 as the DigiLens. The illumination and imaging gratings are arrays of switchable beam deflection grating elements with the preferred grating technology being a SBG as described above. In one embodiment of the invention shown in FIG. 1B the grating elements in the imaging grating 120 are elongate as indicated by 121 with longer dimension orthogonal to the beam propagation direction. In one embodiment of the invention shown in FIG. 1C the imaging grating may comprise a two dimensional array 122 of elements 123 each having optical power in two orthogonal planes. Typically the first and second waveguide paths, that is, the imaging and illumination paths in the waveguide are in opposing directions as illustrated in FIG. 1A. The illumination light will typically be fully collimated while the image light will have some divergence of angle determined by the scattering angle from eye services, the angular bandwidth of the gratings and the numerical aperture of the grating elements. As will be discussed later, in one embodiment the imaging and illumination gratings are provided by a single grating with the illumination and imaging ray paths. Where separate imaging and illumination gratings are used the two gratings may employ different TIR angles within the waveguide. This is advantageous in terms of avoiding the risk of cross coupling of illumination light into the detector and image light into the light source.

In FIG. 1A the illumination light path is illustrated by the light 1010 from the source which is directed into a TIR path 1011 by the input grating and diffracted out of the waveguide as the light generally indicated by 1012. Typically the eye tracker will have a pupil of size 20-30 mm. to allow capture of light reflected from the eye to continue should the waveguide change position relative to the eye. Since the eye tracker will usually be implemented as part of a HMD its pupil should desirably match that of the HMD. FIG. 1A shows return light 1013 reflected from the front surface of the cornea 117 and light 1014 reflected from the retina 118. The corneal and retinal image light enters the waveguide along tray paths such 1015, 1116 and is deflected into a TIR path such as 1017 by an active element of the imaging grating which is switched one element at a time. The light 1017 is deflected into a ray path 1018 toward the detector by the output grating. Advantageously, the detector reads out the image signal in synchronism with the switching of the SBG lens array elements. The detector is connected to an image processing apparatus for determining at least one spatio-temporal characteristic of an eye movement. The image processor, which is not illustrated, detects pre-defined features of the backscattered signals from the cornea and retina. For example, the image processor may be used to determine the centroid of an eye feature such as the pupil. Other trackable features of the eye will be well known to those skilled in arts of eye tracker design and visual optics.

The eye surfaces used for tracking are not necessarily limited to the front surface of the cornea and the retina. The invention can be applied using reflections from any of the surfaces of the lens, iris and sclera including any of the reflections normally referred to as Purkinje reflections. In one particularly important embodiment of the invention to be discussed later the light reflected from the eye is speckle. The speckle may arise from reflections at any of the above surfaces or from the bulk medium of the cornea lens and other parts of the eye.

Advantageously, the light source is a laser emitting in the infrared band. Typically, the laser emits at a wavelength in the range 785-950 nm. The choice of wavelength will depend on laser efficiency, signal to noise and eye safety considerations. Light Emitting Diodes (LEDs) may also be used. In one embodiment of the invention the detector is a two dimensional array. However other types of detector may be used including linear arrays and analogue devices such as position sensing detectors. In the embodiment shown in FIG. 1 the illumination grating provides divergent light. In alternative embodiments of the invention the illumination grating provides collimated light.

The gratings may be implemented as lamina within or adjacent an external surface of the waveguide. In other words the grating may be disposed adjacent an optical surface of the waveguide, comprising at least one of an internal surface or an external surface of the waveguide. For the purposes of discussing the invention we will consider Bragg gratings disposed within the waveguide. Advantageously the gratings are switchable Bragg gratings (SBGs). In certain embodiments of the invention passive gratings may be used. However, passive gratings lack the advantage of being able to direct illumination and collect image light from precisely defined areas of the pupil. In one embodiment the gratings are reverse mode SBGs. Although the invention is discussed in relation to transmission gratings it should be apparent to those skilled in the art that equivalent embodiments using reflection gratings should be feasible in most cases. The gratings may be surface relief gratings. However, such gratings will be inferior to Bragg gratings in terms of their optical efficiency and angular/wavelength selectivity.

Figure 2:
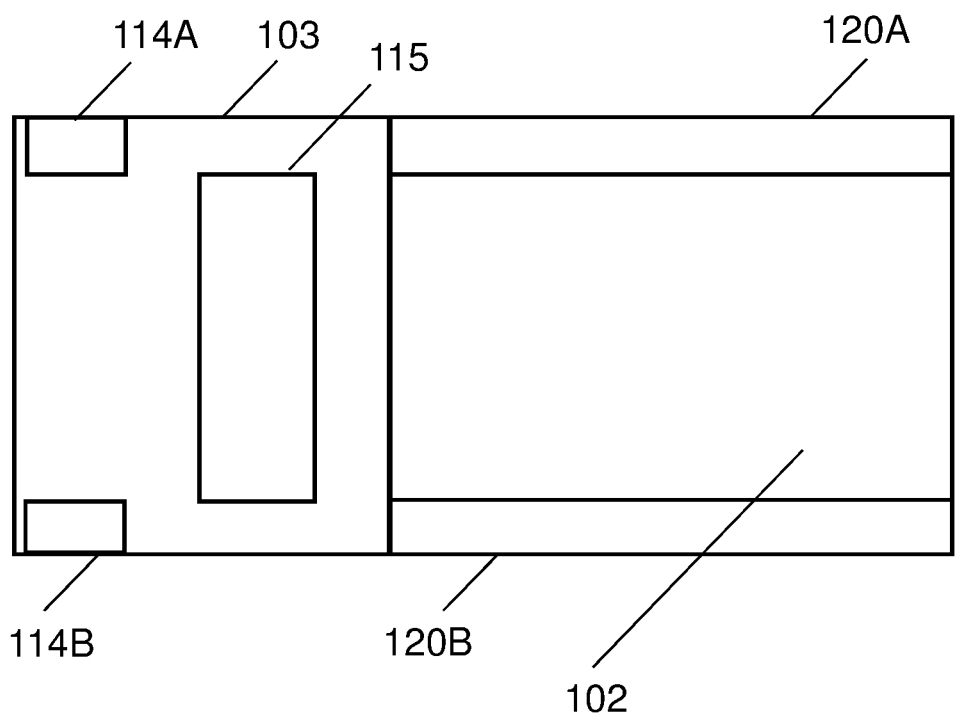
FIG. 2 is a schematic plan view of the eye tracker shown the imaging and illumination gratings and input and output gratings in one embodiment of the invention.

The input and illumination gratings may be configured in many different ways. FIG. 2 is a schematic plan view showing one possible implementation for use with the embodiment of FIG. 1. Here the input grating comprises two grating elements 114A,114B and the illumination grating is also divided into the upper and lower gratings 120A,120B, each providing narrow beam deflecting grating strips above and below the imaging grating 102. The detector grating 115 is also indicated. Since the guided beams in the input and illumination grating are collimated, and likewise the guided beams in the imaging and detector gratings, there is no cross talk between the two regions of the waveguide.

Figure 3:
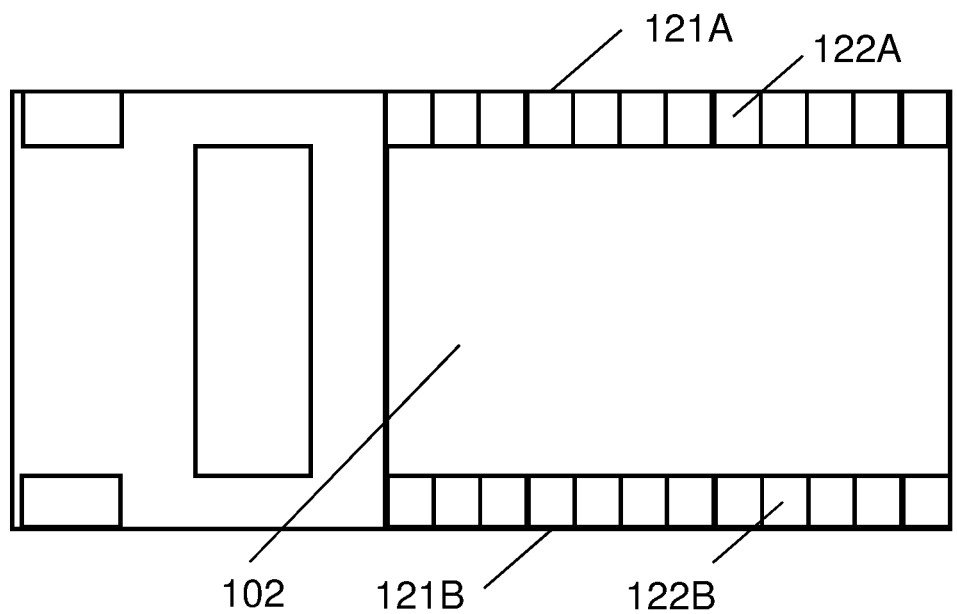
FIG. 3 is a schematic plan view of the eye tracker shown the imaging and illumination gratings and input and output gratings in one embodiment of the invention.
Figure 4:
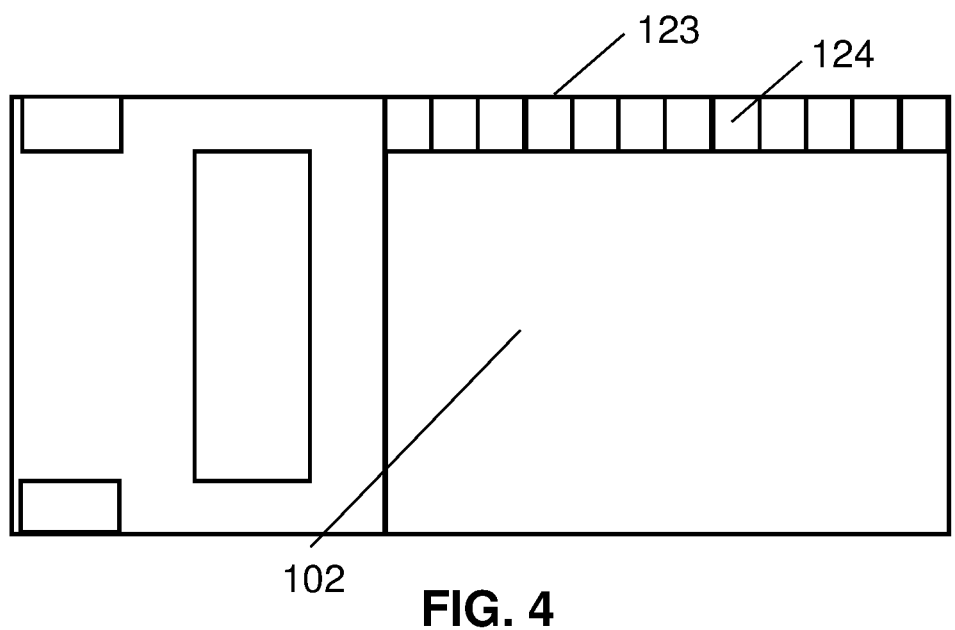
FIG. 4 is a plan view of the eye tracker shown the imaging and illumination gratings and input and output gratings in one embodiment of the invention.

In the embodiment of the invention shown in FIGS. 3-4, which is similar to the one of FIG. 2, the upper and lower illumination grating may be arrays of switchable grating elements 121A,121B comprising switchable grating elements such as 122A,122B. The SBG deflector arrays scroll illumination across the exit pupil in step with the activation of the imaging grating elements. Finally, in the embodiment of FIG. 4 the illumination grating comprises just one strip 123 containing elements 124 disposed along the top edge of the imaging grating.

The invention does not assume any particular configuration of the grating elements. It is important to note that the SBGs are formed as continuous lamina. Hence the illumination gratings elements may be considered to be part of the imaging grating. This is a significant advantage in terms of fabrication and overall form factor. In embodiments where the illumination grating is split into two elements as discussed above the input laser light may be provided by one laser with the upper and lower beam being provided by a beam splitting means. Alternatively, two separate laser modules may be used to provide light that is coupled into the waveguide via the input gratings 114A,114B are illustrated in FIGS. 3-4. The invention does not assume any particular method for providing the laser input illumination or coupling the laser light into the waveguide. Many alternative schemes should be apparent to those skilled in the art of optical design.

Figure 5:
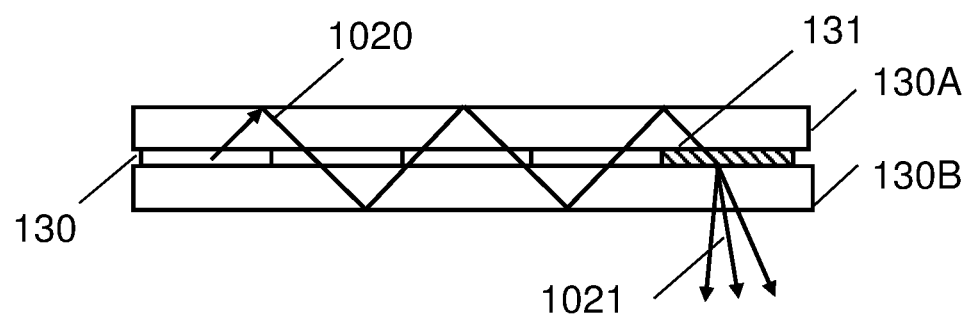
FIG. 5 is a schematic cross section view of an illumination grating used in one embodiment of the invention.

The illumination grating may provide illumination light of any beam geometry. For example, the light may be a parallel beam emitted normally to the surface of the eye tracker waveguide. The illuminator grating is illustrated in more detail in the schematic side elevation view of FIG. 5 in which the SBG linear array 130 is sandwiched between transparent substrates 130A,130B. Note that the substrate layers extended to cover the entire waveguide and therefore also act as the substrates for the imaging grating. Advantageously, the ITO layers are applied to the opposing surfaces of the substrates with at least one ITO layer being patterned such that SBG elements may be switched selectively. The substrates and SBG array together form a light guide. Each SBG array element has a unique optical prescription designed such that input light incident in a first direction is diffracted into output light propagating in a second direction. FIG. 5 shows TIR illumination beam 1020 being deflected by the active element 131 to provide divergent illumination light 1021.

Figure 6:
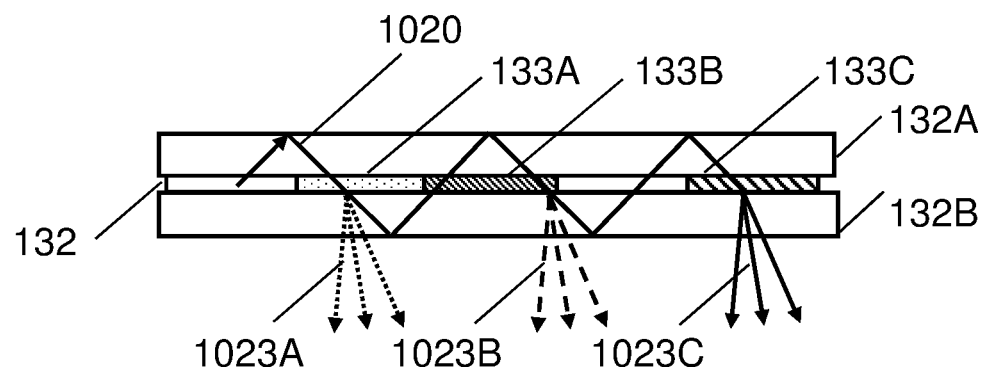
FIG. 6 is a schematic cross section view of an illumination grating used in one embodiment of the invention.
Figure 7:
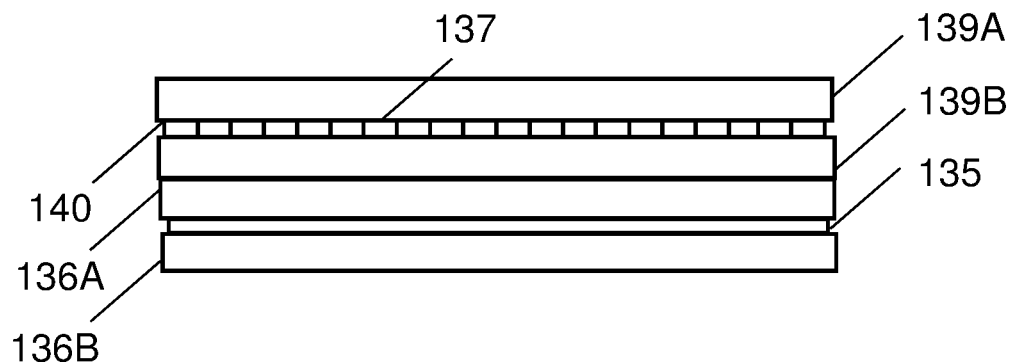
FIG. 7 is a schematic cross section view of a first aspect of an imaging grating used in one embodiment of the invention.

An alternative embodiment of the linear deflector array is shown in the schematic side elevation view of FIG. 6. In this cases the array 132 sandwiched by substrates 132A,132B is based on a lossy grating that diffracts incrementally increasing fractions of the guided beam out of the waveguide towards the eye. Beam portions 1023A-1023C diffracted by the grating elements 133A-133C are illustrated. Typically, the index modulation of the grating elements will be designed to provide uniform extraction along the array and hence uniform output illumination. Note that the geometrical optics of FIGS. 5-6 has been simplified for the sake of simplifying the description.

Advantageously, the illumination grating elements may encode optical power to provide sufficient beam spread to fill the exit pupil with light. A similar effect may be produce by encoding diffusion characteristics into the gratings. The apparatus may further comprise an array of passive holographic beam-shaping diffusers applied to the substrate, overlapping the linear SBG array, to enhance the diffusion. Methods for encoding beam deflection and diffusion into diffractive devices are well known to those skilled in the art of diffractive optics. Cross talk between the imaging and illumination channels is overcome by configuring the SBGs such that the illumination TIR path within the eye tracker lies outside the imaging TIR path.

Figure 8:
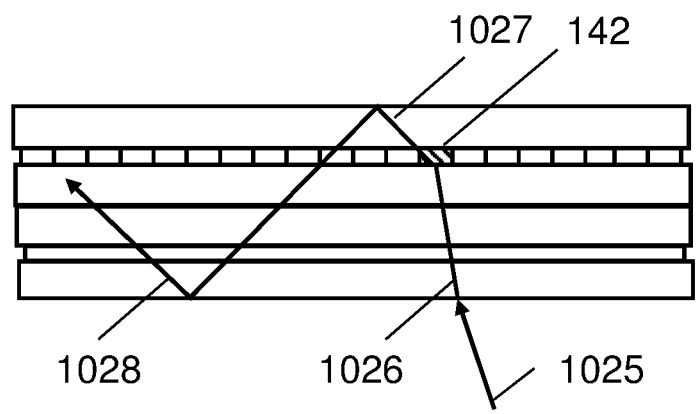
FIG. 8 is a schematic cross section view of a second aspect of an imaging grating used in one embodiment of the invention.

In one embodiment of the invention the imaging grating may also encode optical power. A two layer SBG imaging grating that encodes optical power is illustrated in FIGS. 7-10. The arrays are shown in their stacked configuration in FIG. 7. The substrates 136A,136B and 139A,139B together provide the imaging waveguide as illustrated in FIG. 8 where the ray path from the eye into the waveguide via an activated SBG element 42 is represented by rays 1025-1028. The arrays are shown in front, plan and side elevation views in FIGS. 9-10. The arrays comprise linear arrays of column elements each having the optical characteristics of a cylindrical lens. The column vectors in the two arrays are orthogonal. The first array comprises the SBG array 135 sandwiched by the substrates 136A,136B with one particular element 137 being indicated. The second array comprises the SBG array 40 sandwiched by the substrates 139A,139B with one particular element 141 being indicated.

Figure 11A:
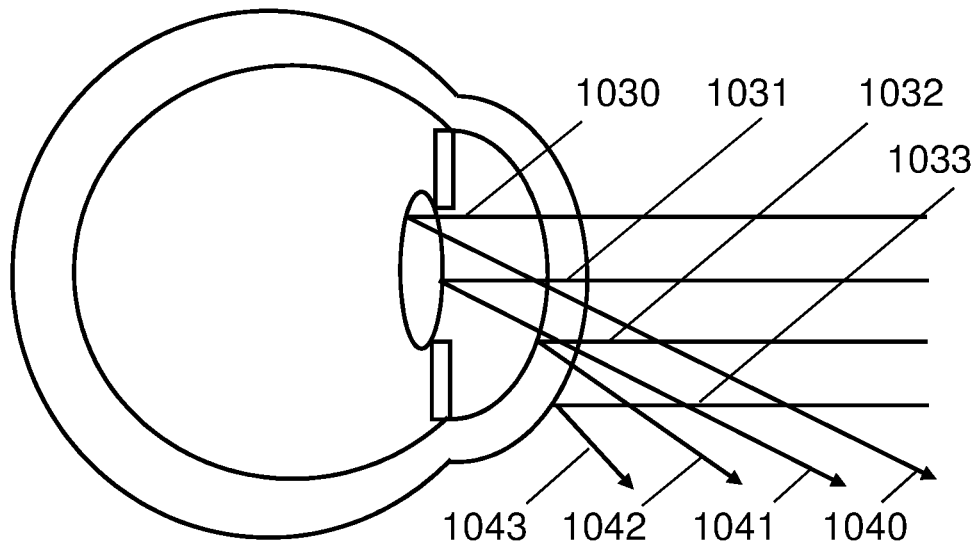
FIG. 11A is a schematic cross view of the human eye illustrating the formation of the Purkinje images.
Figure 11B:
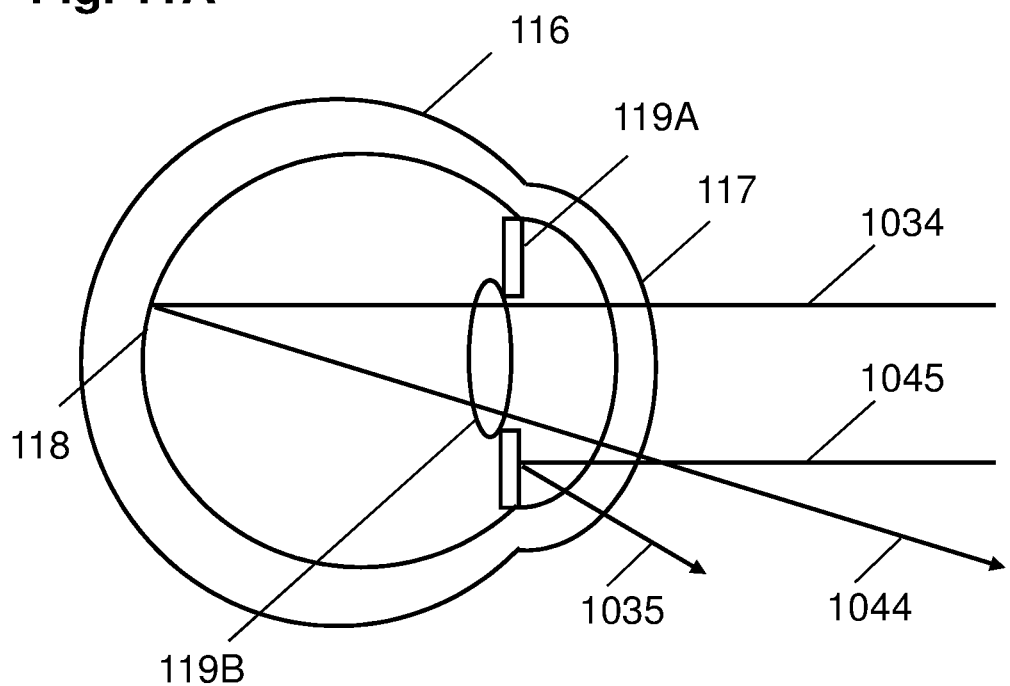
FIG. 11B is a schematic cross view of the human eye illustrating reflections from the retina and iris.

FIG. 11A illustrates the principles of the formation of the first four Purkinje images corresponding to reflections off the front of the cornea 1033,1043; the back of the cornea 1032, 1042; the front of the eye lens 1031,1041; and the back of the eye lens 1030,1040. FIG. 11B illustrates the formation of images of the retina by rays 1034,1044 and the iris by rays 1035,1045.

Figure 12A:
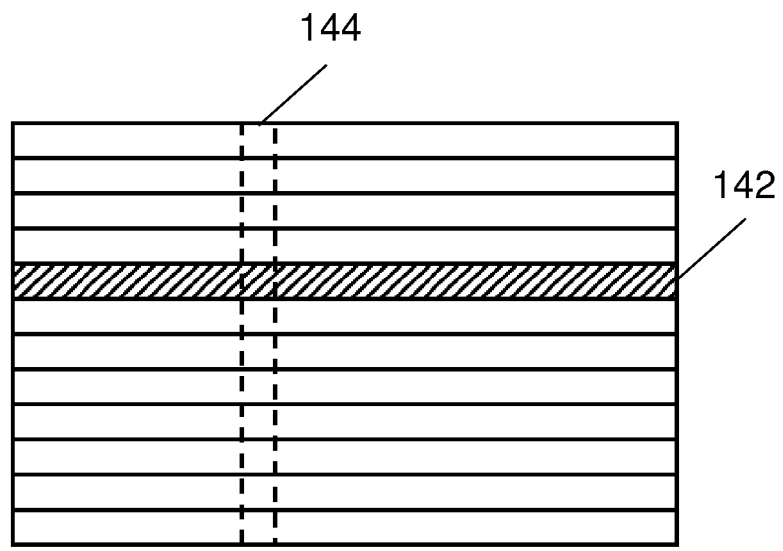
FIG. 12A is a schematic plan view illustrating a first aspect of the localization of an eye feature by a two layer imaging grating each layer comprising elongate elements with the elements of the two gratings at right angle.
Figure 12B:
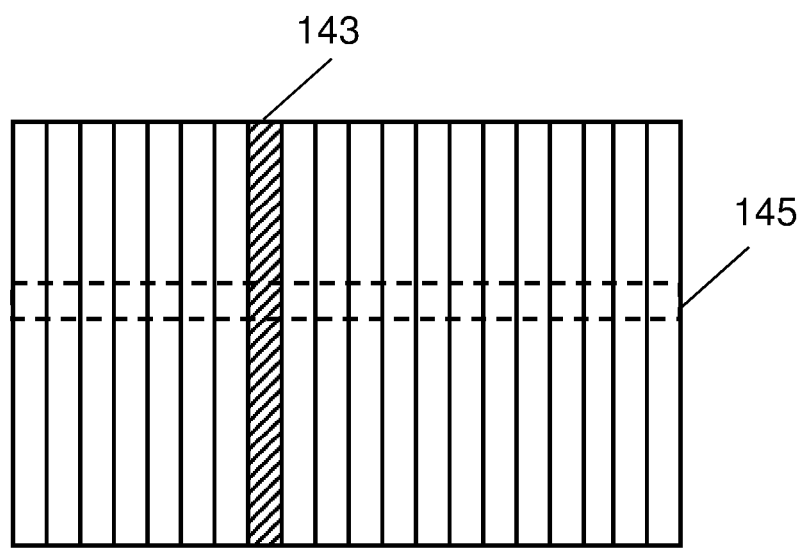
FIG. 12B is a schematic plan view illustrating a second aspect of the localization of an eye feature by a two layer imaging grating each layer comprising elongate elements with the elements of the two gratings at right angle.

FIG. 12 shows how the first and second SBG lens arrays of FIGS. 7-10 may be used to localize an eye feature such as by scanning row and column SBG elements such as 142 and 143.

With regard to the use of speckle as an eye signature FIG. 13 illustrates how the size of speckle feature as recorded in two captured speckle images may vary with the eye orientation and displacement with respect to the eye optical axis 1050. FIG. 13A illustrates speckle formed by illuminating the eye along the direction 1050A which is initially parallel to the eye optical axis. The components of the corneal and retinal speckle light parallel to the eye optical axis are indicated by 1050B,1050C. FIG. 14A shows the formation of speckle with the eye rotated in the plane of the drawing. The detected corneal and retinal speckle light 1050D,1050E parallel to the direction 1050 which is now no longer parallel to the eye optical axis is shown. As shown by the insets 1051,1053 the size and spatial distribution of the speckles changes as the eye rotates. Correlation of the two speckle patterns will provide a measure of the eye rotation. Note that, typically, the speckle patterns recorded at the detector will combine separate speckle patterns from the cornea and retina as well as other surfaces and biological media interacting with the illumination beam. In one embodiment of the invention the eye tracker processor compares the speckle images due to light being scattered from the retina and cornea. When the eye is panned horizontally or vertically the relative position of the speckle pattern from the cornea and retina change accordingly allowing the direction of gaze to be determined from the relative trajectories of the reflected light beams.

Figure 15A:
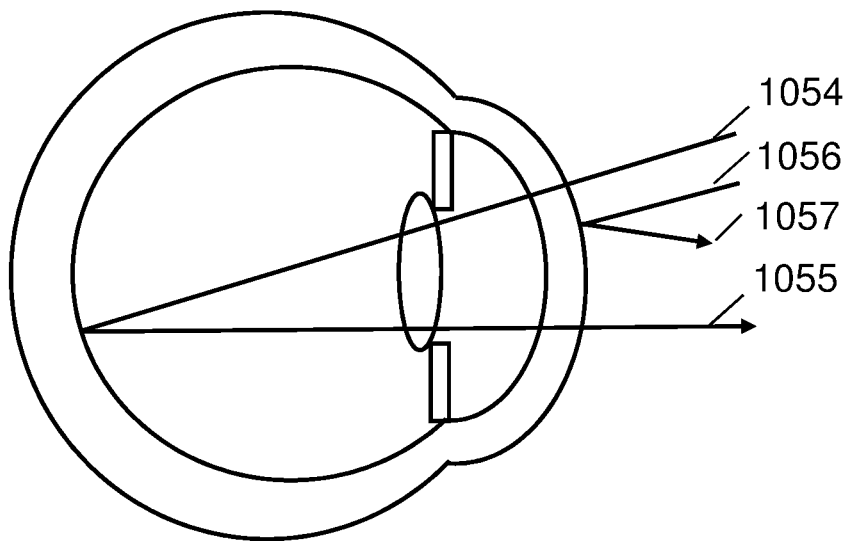
FIG. 15A is a schematic cross section view of a human eye in a first rotational state showing reflection from the retina and cornea.
Figure 15B:
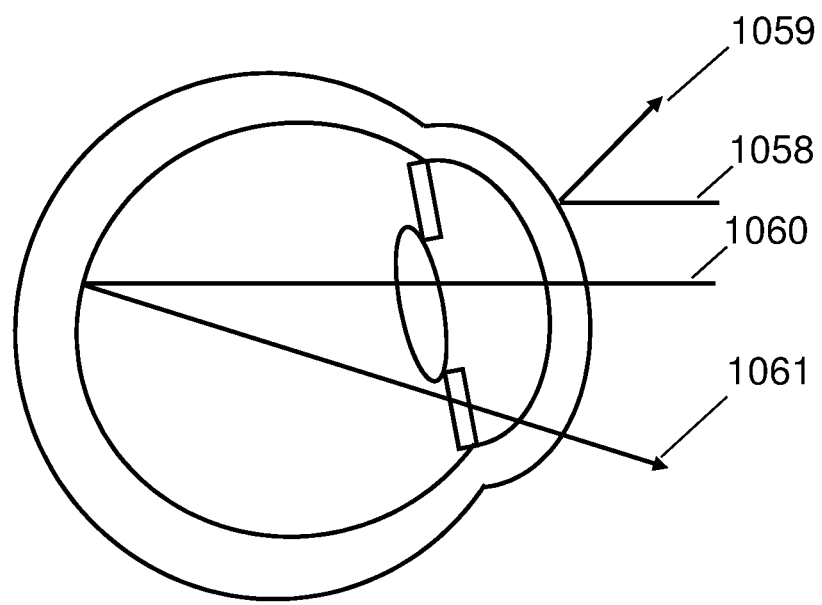
FIG. 15B is a schematic cross section view of a human eye in a second rotational state showing reflection from the retina and cornea.

FIG. 14 represents the front of the eye 146 cornea 147 and illuminated region 148 of the retina illustrates the direction of movement of corneal and retinal speckle features as indicated by the vectors 149,150 correspond to the ocular displaces illustrated in FIG. 15. In general the ray reflection vectors directions will be closely linked to eye rotation. FIG. 15A represents the reflection of rays from the cornea 1056, 1057 and retina 1054,1055 for one eye position. FIG. 15B shows the reflection paths from the cornea 1058,1059 and the retina 1060,1061 after a horizontal (or vertical) eye rotation. Reflection from the cornea has a strong secular component. Retinal reflection is more diffuse. The size of the corneal reflected angles would ordinarily require a large angular separation between the illumination and detection optical axes. This would make eye tracking using corneal reflections over large FOVs very difficult. The invention avoids the problem of imaging large reflection angles (and dealing with are lateral and vertical eye movements which can arise from slippage) by using matched scrolling illumination and detection. Hence the reflection angle becomes relatively small and can be approximated to: $\Psi \sim 2[(D/r-1)\Phi+d/r]$ where r is the cornea radius $\Phi$ is the eye rotation and D is the distance of the eye centre from the displaced centre of curvature of the cornea and d is the lateral displacement of the eye centre.

Figure 16:
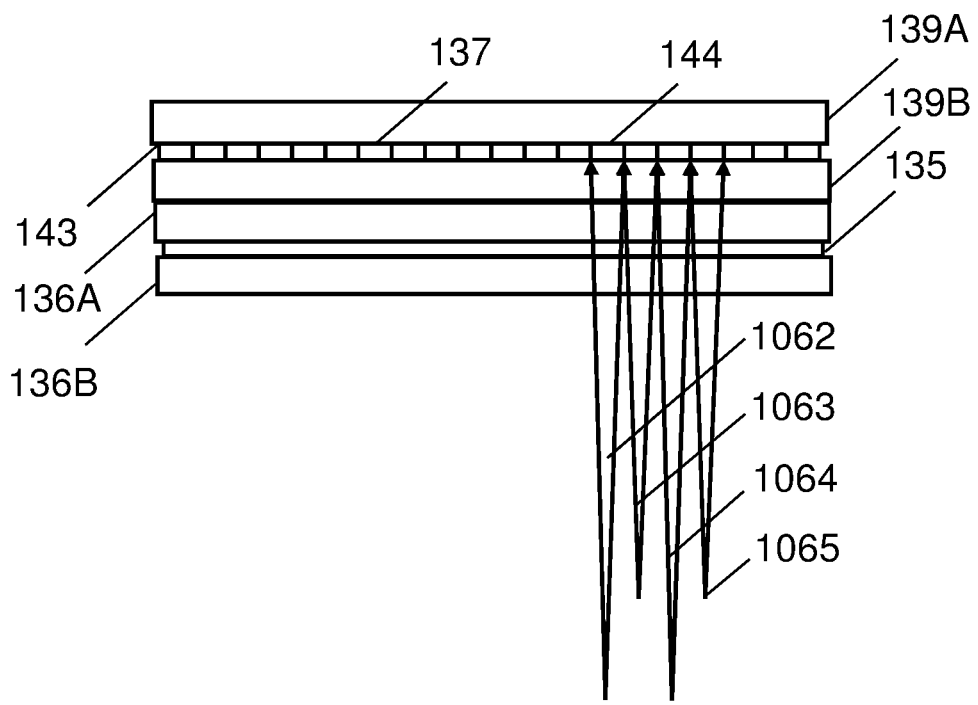
FIG. 16 is a schematic cross section view of an imaging grating comprising an array of SBG lens elements with focal length varying across the exit pupil in one embodiment of the invention.
Figure 17A:
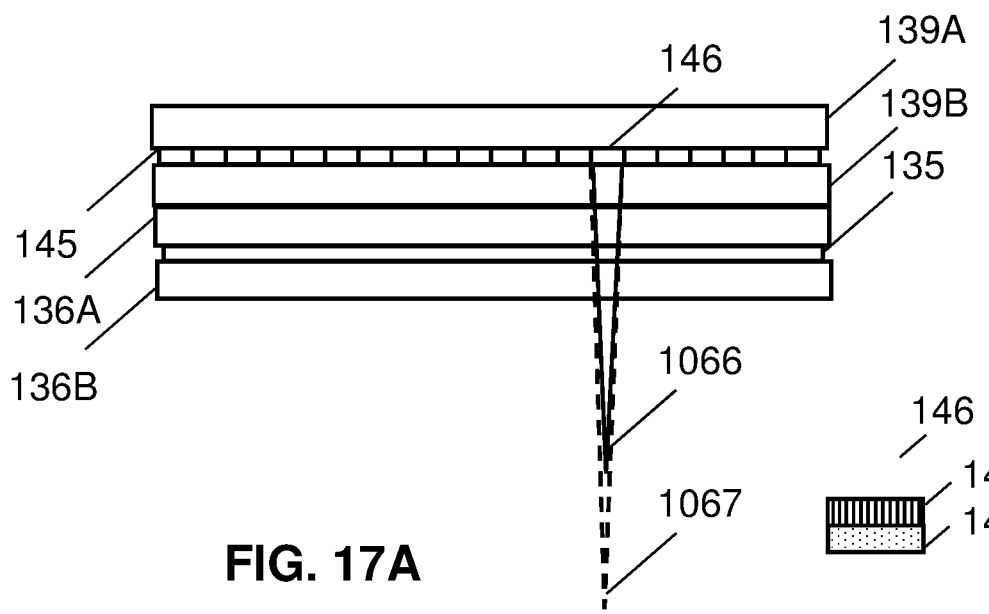
FIG. 17A is a schematic cross section view of an imaging grating comprising an array of variable power lenses in one embodiment of the invention.
Figure 17B:
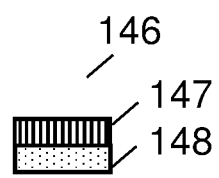
FIG. 17B is a detail of FIG. 17A showing a variable power lens comprising a variable index layer and a diffractive element of fixed focal length.

In one embodiment of the invention based on the one of FIGS. 7-10 the imaging grating comprises an SBG array 143 in which the lens elements 144 have varying focal length across the exit pupil. In the embodiment of FIG. 16 grating elements of first and second focal length indicated by the divergent beams 1062,1064 and 1063,1065 are uniformly interspersed. In one embodiment illustrated in FIG. 17A the imaging waveguide comprises arrays 145 of variable power lens elements 146. As shown in the detail of FIG. 17B a variable power lens would be provided by combining a diffractive element 147 of fixed focal length with a variable index layer 148.

Figure 18:
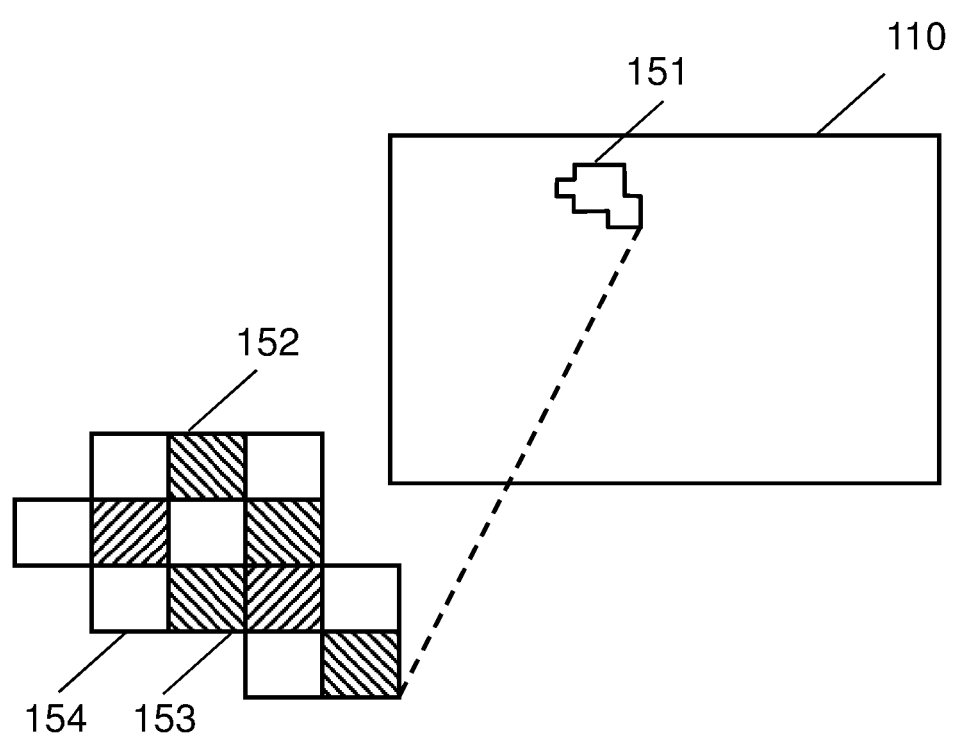
FIG. 18 is a schematic illustrate of an imaging grating in one embodiment of the invention in which the imaging grating comprises an array of interspersed grating elements having at least two different prescriptions.

In one embodiment of the invention shown in the schematic view of FIG. 18 the imaging grating comprises a single layer two dimensional SBG array. A group of elements labelled 152 which comprises interspersed elements such as 153,154. The group forms the image region 151 at the detector 110. Each SBG element is characterized by one from a set of at least two different prescriptions. FIG. 18 does not show the details of the waveguide and the illumination and input/output gratings. At least one of the SBG prescriptions corresponds to a lens for forming an image of the eye on the detector. At least one prescription is optimized for imaging a signature formed by a surface of the eye. Hence the embodiment of FIG. 18 allows eye tracking to be performed using speckle patterns and conventional features such as Purkinje reflections.

Figure 19:
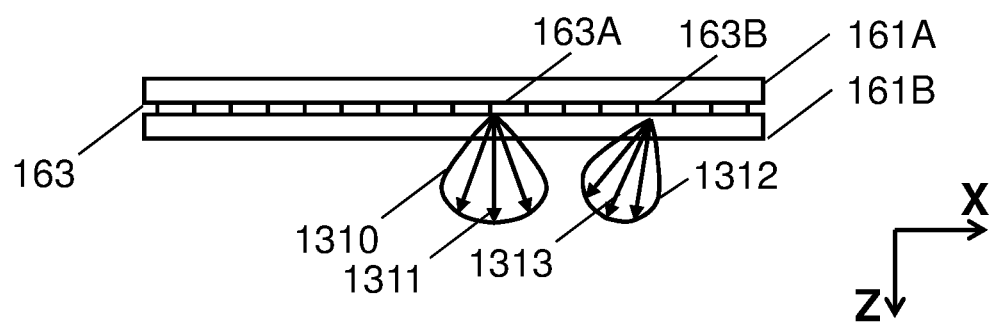
FIG. 19 is a schematic cross section view of the illumination grating of an eye tracker using separate illumination and imaging gratings in one embodiment of the invention.
Figure 20:
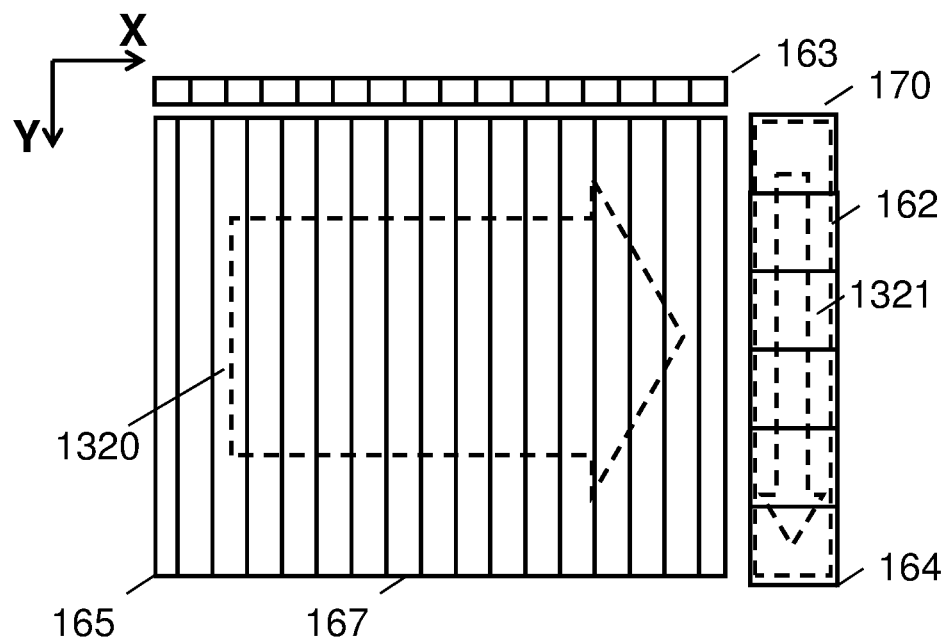
FIG. 20 is a schematic plan view the illumination grating of an eye tracker using separate illumination and imaging gratings in one embodiment of the invention.
Figure 21:
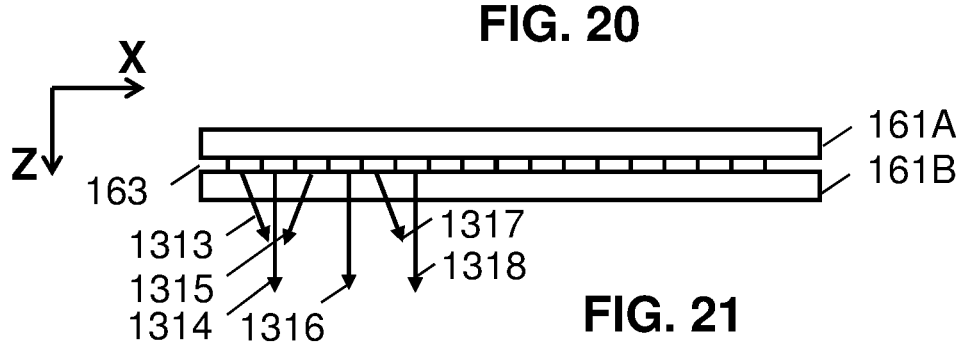
FIG. 21 is a schematic cross section view of an alternative illumination grating of an eye tracker using separate illumination and imaging gratings in one embodiment of the invention.

FIGS. 19-24 provide schematic illustrations of aspects of an eye tracker based on the principles of FIGS. 1-6. In this embodiment of the invention the earlier described imaging, illumination, input and output gratings are augmented by an additional grating to be referred to as an image sampling grating which overlays the output grating. FIG. 19 shows a side elevation view of the illumination grating 163. FIG. 20 is a plan view showing the imaging grating 165, the illumination grating 163 and the image sampling grating 170 overlaid on the output grating 164. FIG. 21 is a side elevation view of an alternative embodiment of the illumination grating 163. FIG. 22A is a plan view of the imaging grating, the image sampling grating 14 and the detector module 180. FIG. 22B is a plan view of the image sampling grating and the detector module. FIG. 22C is a cross sectional view showing the imaging grating and the image sampling grating. FIG. 22D is a cross sectional view of the image sampling grating and the detector module. Finally, FIG. 22E is a cross sectional view of the imaging grating, the image sampling grating and the detector module. To assist the reader the projection plane of each illustration is referred to a Cartesian XYZ reference frame.

The imaging grating 165 comprises an array of column-shaped SBG elements, such as the one labelled 167, sandwiched by substrates 168,169. Column elements of the imaging grating 165 are switched on and off in scrolling fashion backwards and forward along the direction indicated by the block arrow 1320 in FIG. 20 such that only one SBG column is in its diffractive state at any time.

The illuminator array 163 is shown in detail in FIG. 19 comprises substrates 161A,161B sandwiching an array of SBG rectangular elements such as 163A,163B. The SBG elements may have identical diffracting characteristics or, as shown in FIG. 19, may have characteristics that vary with position along the array. For example, the element 163A provides a diffusion distribution 1310 centered on a vector at ninety degrees to the array containing rays such as 1311.

However, the element 63B provides an angled distribution 1312 containing rays such as 1313. In an alternative embodiment shown in FIG. 21 the diffusion polar distributions may have central ray directions that varying in a cyclic fashion across the array as indicated by the rays 1313-1318.

The image sampling grating 170, comprising an array of rectangular SBG beam deflecting elements 173 such as 176 (shown in its diffracting state in FIG. 22C) sandwiched by substrates 174,175. The waveguide containing the imaging grating 165, illumination grating 163 and the output grating 164 is separated from the image sampling grating 170 by a medium (not illustrated) which may be air or a low refractive index transparent material such as a nanoporous material.

Infrared light from a surface of the eye is coupled into the waveguide by an active imaging grating element, that is, by a diffracting SBG column. The guided beam undergoes TIR in the waveguide up to the output grating. As shown in FIG. 22C the output grating 164 deflects the beam through ninety degrees into the direction 1322 towards the image sampling grating 170. As shown in FIG. 22C a portion of the beam 1322 is deflected into the image sampling grating by an active SBG element 176 where it undergoes TIR in the direction indicated by the ray 1323 (and also by block arrow 1321 in FIG. 20). The light that is not sampled by the image sampling grating indicated by 1320 1321 is trapped by a suitable absorbing material, which is not illustrated. The TIR beam is deflected in the detector module 180 by a first holographic lens 172 to provide out image light 1325. Turning now to FIG. 22D we see that the detector module contains mirror surfaces 177A,177B and a further holographic lens 178 which forms an image of the eye features or speckle pattern that is being tracked on the detector array 166. Note the holographic lens 172,178 may be replaced by equivalent diffractive elements based on Bragg or surfaces relief gratings. Conventional refractive lens elements may also be used where size constraints permit.

Figure 23:
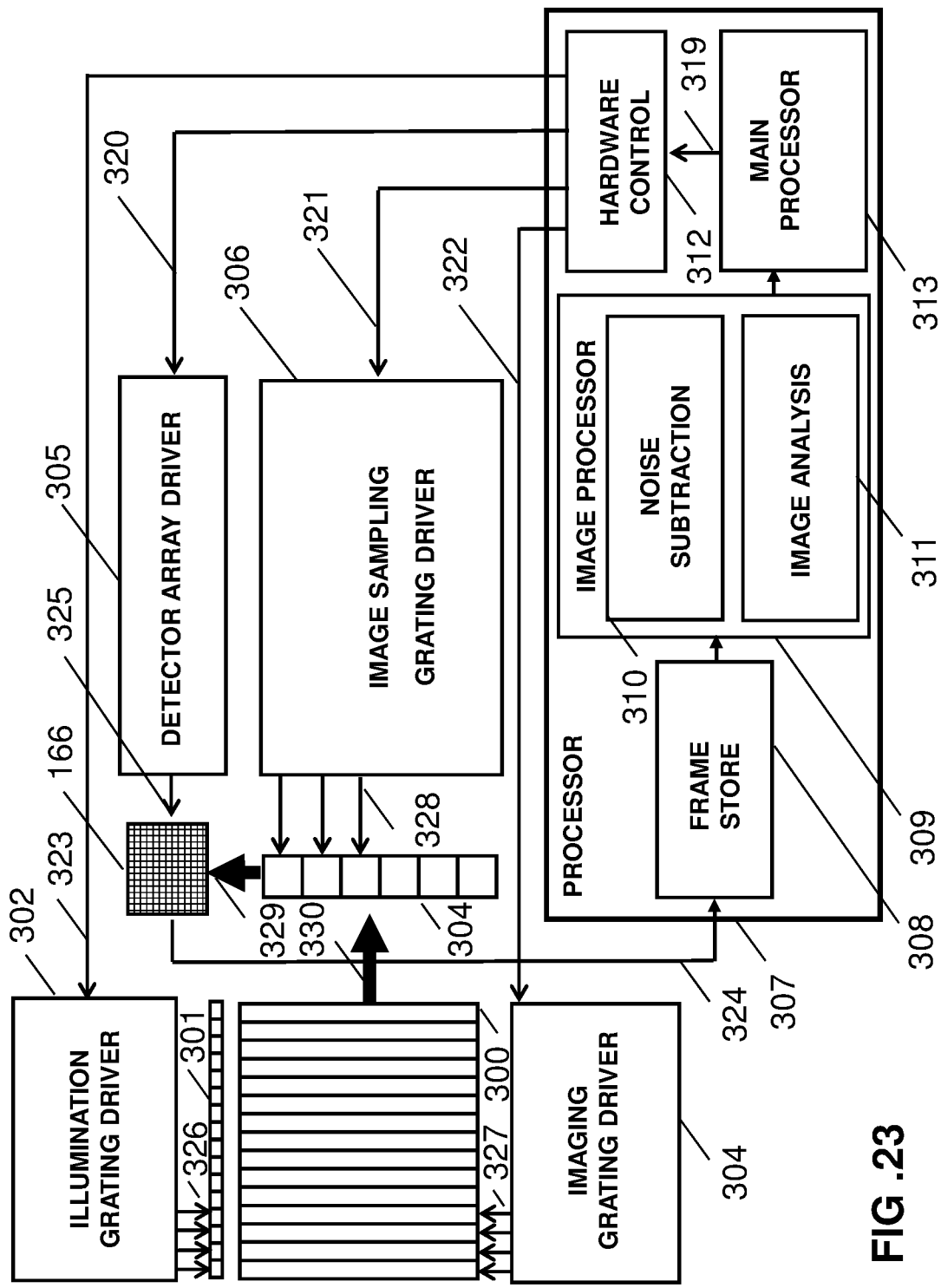
FIG. 23 is a block diagram showing the principal modules of an eye tracker system using separate illumination and imaging gratings in one embodiment of the invention.

FIG. 23 is a system block diagram of the eye tracker of FIGS. 19-22. The system modules comprise the imaging grating 300, illumination grating 301, illumination grating driver 302, illumination sampling grating 303, imaging grating driver 304, detector driver 30, image-sampling array driver 306, detector 166 and processor 307. The apparatus also comprises a laser driver which is not illustrated. The optical links from the image grating to the image sampling array and the image sampling array to the detector are indicated by the block arrows 329,330. The processor 307 comprises a frame store 308 or other image memory device for the storage of captured eye image or speckle pattern frames and an image processor 309 further comprising hardware or software modules for noise subtraction 310 and image analysis 311. The processor further comprises hardware control module 312 for controlling the illumination, imaging and image sampling grating drivers, all said modules operating under the control of a main processor 313. Data and control links between components of the system are indicated by 319-325. In particular, each driver module contains switching circuitry schematically indicated by 326-328 for switching the SBG elements in the imaging grating, illumination grating array, and image sampling grating.

Figure 24:
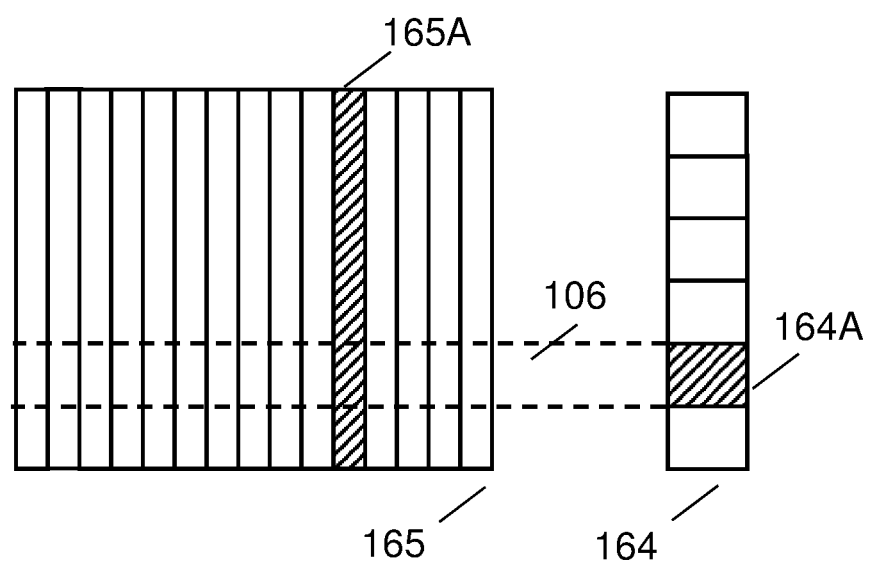
FIG. 24 is a schematic illustration of a grating element switching scheme provided by the imaging grating and image sampling grating in one embodiment of the invention.

FIG. 24 illustrates the switching scheme used in the imaging grating and image sampling grating. The illumination grating elements are switched in phase with the imaging grating columns. Column element 165A of the imaging grating array 165 and element 170A of the readout array 170 are in their diffracting states. The projection (indicated by 170B) of element 170A on the column 65A defines an active detection aperture. Using such as scheme it is possible to track features of the eye using a X,Y localization algorithm aided by predictions obtained from analysis of displacement vectors determined from successive frames. Methods for implementing such search schemes will be known to those skilled in the art. The invention does not rely on any particular algorithm or processing platform.

Figure 25:
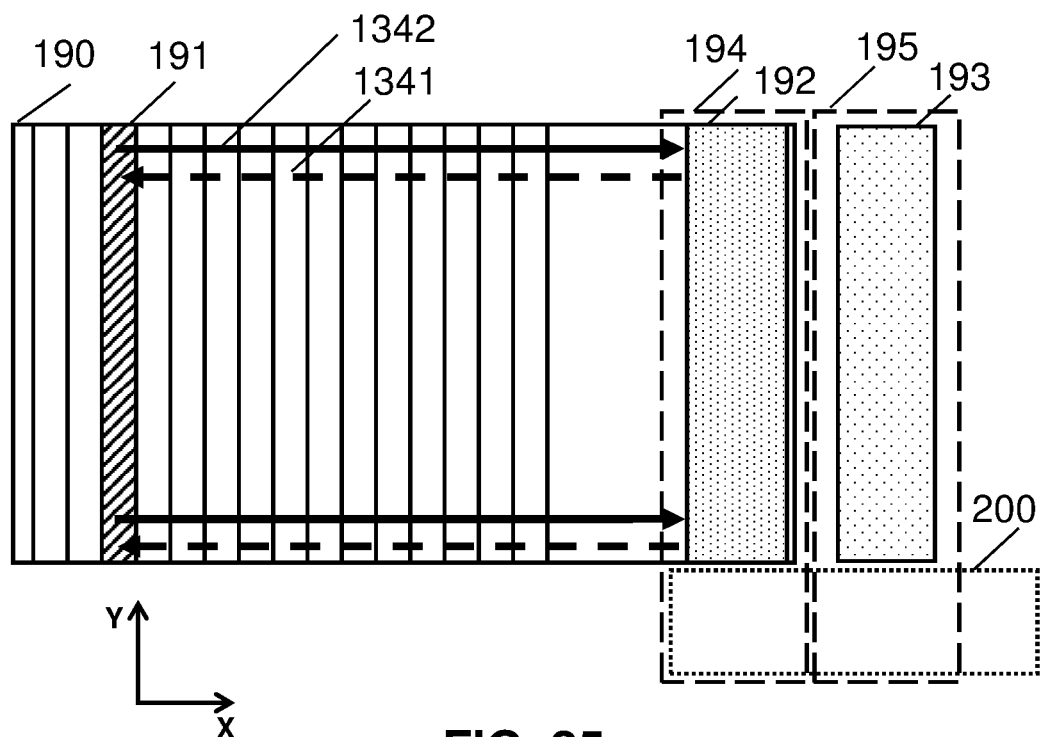
FIG. 25 is a schematic plan view of an eye tracker using common illumination and imaging gratings in one embodiment of the invention.
Figure 26:
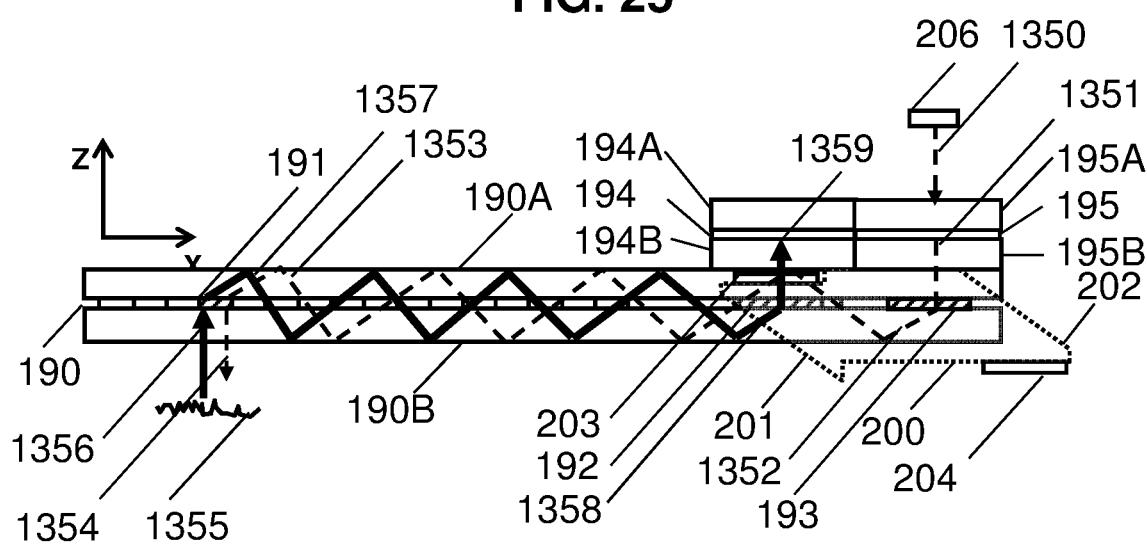
FIG. 26 is a schematic cross section view showing the imaging and illumination grating and the input, output, image sampling and detector sampling gratings of an eye tracker using common illumination and imaging gratings in one embodiment of the invention.

FIGS. 25-27 provide schematic illustrations of aspects of an eye tracker that extends the embodiment of FIGS. 19-24 by introducing a further grating component to be referred to as an illumination sampling grating which overlays the input grating. The other feature of this embodiment is that the illumination grating is no longer separate from the imaging gratings. Instead the two are combined in a bi-directional waveguide in which a common switchable column grating is used to illuminate and image the eye with the illumination and image wave-guided light propagating in opposing directions. The combined gratings will be referred to as the illumination and imaging grating. As will be explained below the function of the illumination sampling grating, which is similar in structure to the image sampling grating, is to concentrate the available illumination into region of the eye selected by the image sampling grating. This confers the dual benefits of light efficiency and avoidance of stray light from regions of the eye that are not being tracked.

Figure 27A:
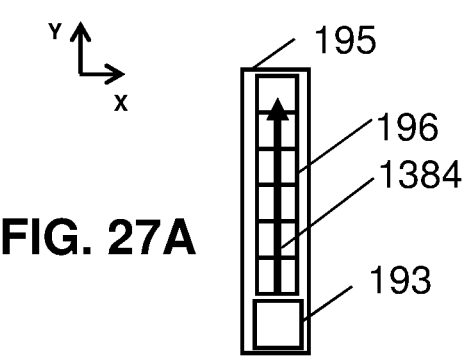
FIG. 27A is a schematic plan view of the image sampling grating of an eye tracker using common illumination and imaging gratings in one embodiment of the invention.
Figure 27B:
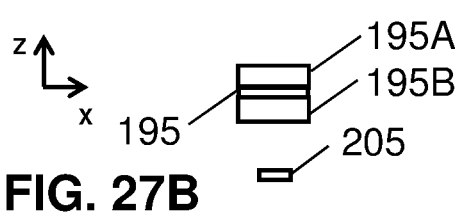
FIG. 27B is a schematic cross section view of the illumination sampling grating, the input grating and laser of an eye tracker using common illumination and imaging gratings in one embodiment of the invention.
Figure 27C:
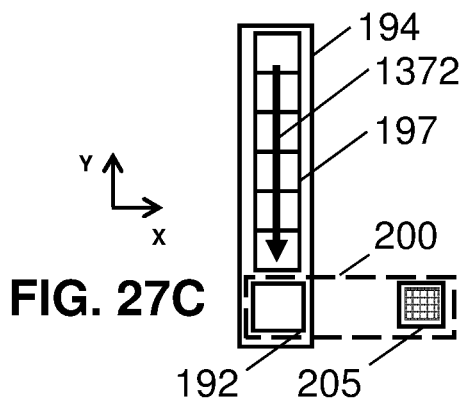
FIG. 27C is a schematic plan view image sampling grating and the detector module with detector overlaid of an eye tracker using common illumination and imaging gratings in one embodiment of the invention.

Turning now to the drawings, FIG. 25 is a plan view showing the imaging and illumination grating 190, the image sampling grating 194, illumination sampling grating 195 the input grating 193 and output grating 192 and the detector module 200. Column elements of the illumination and imaging grating are switched on and off in scrolling fashion backwards and forward such that only one SBG column is in its diffractive state at any time. The counter propagating beam paths are indicated by 1341,1342. FIG. 26 shows the components of FIG. 25 in a side elevation view. FIG. 27A is a plan view of the illumination sampling grating. FIG. 27B is a cross sectional view of the illumination sampling grating 195 including the input grating 193 and the laser 205. FIG. 27C is a plan view of the image sampling grating 194 showing the detector module 200 and detector 205 overlaid.

Figure 27E:
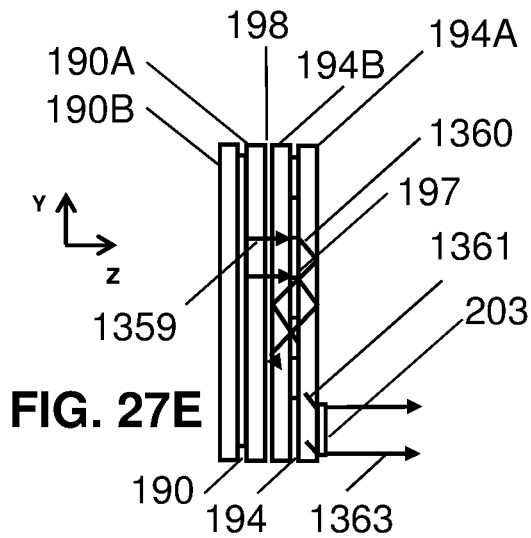
FIG. 27E is a schematic cross section view of the output grating and the image sampling grating an eye tracker using common illumination and imaging gratings in one embodiment of the invention.
Figure 27F:
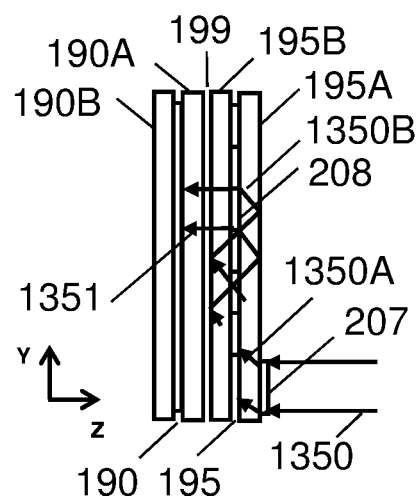
FIG. 27F is a schematic cross section view of the input grating and the illumination sampling of an eye tracker using common illumination and imaging gratings in one embodiment of the invention.
Figure 27D:
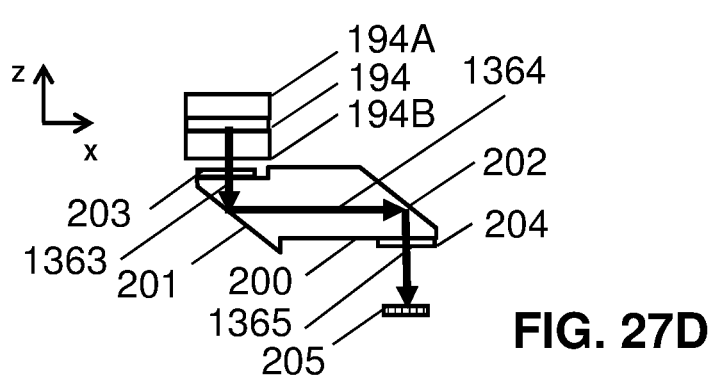
FIG. 27D is a schematic plan side elevation view showing the image sampling grating and detector of an eye tracker using common illumination and imaging gratings in one embodiment of the invention.

FIG. 27D is a side elevation view showing detector module 200 in more detail. The detector 205 and a cross section of the image sampling grating 194 are included. FIG. 27E is a cross sectional view of the output grating 192 and the image sampling grating 194. FIG. 27F is a cross section view of the input grating 193 and the illumination sampling grating 194. To assist the reader the projection plane of each illustration is referred to a Cartesian XYZ reference frame.

The illumination and imaging grating comprises the array 190 of column-shaped SBG elements, such as the one labelled 191 sandwiched by the transparent substrates 190A, 190B. The input and output grating which are disposed in the same layer are labelled by 193,192 respectively. The detector module 200 is delineated by a dotted line in FIGS. 25-26 and in more detail in FIG. 27D. The image sampling grating 194, comprises an array of rectangular SBG beam deflecting elements (such as 197) sandwiched by substrates 194A, 194B. Typically the imaging grating and image sampling grating are separated by a medium 198 which may be air or a low refractive index transparent material such as a nanoporous material. The illumination sampling grating 195 which is has a very similar architecture to the image sampling grating comprises an array of rectangular SBG beam deflecting elements (such as 196) sandwiched by substrates 195A,195B. Typically the imaging grating and image sampling grating are separated by a medium 199 which may be air or a low refractive index transparent material such as a nanoporous material.

Referring to FIG. 26 and FIG. 27F illumination light 1350 from the laser is directed into the illumination sampling grating by a coupling grating 207. The light then proceeds along a TIR path as indicated by 1350A, 1350B up to an active element 208 where it is diffracted into the direction 1351 towards the input grating. Not that the image sampling grating directs all of the illumination light through the active element of the illumination sampling grating the elements of which are switched in synchronism with the elements of the image sampling grating to ensure that at any time the only the region of the that is being imaged receives illumination. The illumination path in the waveguide is indicated by 1352-1354.

Infrared light 1356 (also illustrated as the signature 1355) from one or more surfaces of the eye is coupled into the waveguide by a diffracting SBG column such as 191. The guided beam indicated by 1357,1358 undergoes TIR in the waveguide up to the output grating 192. The output grating deflects the beam through ninety degree into the direction 1359 towards the image sampling grating. As shown in FIG. 27E the beam in direction 1359 is deflected into the image sampling grating by an active SBG element 197 where it undergoes TIR along the ray path indicated by 1360, 1361. The TIR beam is deflected into the detector module 200 as light 1363 by a first holographic lens 203. Any light that is not sampled by the image sampling grating is trapped by a suitable absorbing material, which is not illustrated. The absorbing material may be a prism, prism array, an infrared absorbing coating or some other means known to those skilled in the art.

The detector module contains mirror surfaces 201,202 and a further holographic lens 204 which forms an image of the eye signature that is being tracked on the detector array 205. The ray path from the image sampling grating to the detector is indicated by the rays 1363-1365. Advantageously, the mirror surfaces are coatings applied to opposing faces of a prismatic element. However, the invention does not rely on any particular scheme for steering the image light towards the detector array. Note that the holographic lens 203,204 may be replaced by equivalent diffractive elements based on Bragg or surfaces relief gratings. Conventional refractive lens elements may also be used where size constraints permit.

In one embodiment of the invention illumination light from laser module is converted into S-polarized light which is coupled into the eye tracker waveguide by the input grating. This light is then converted into circularly polarized light using a quarter wave plate. An active SBG column will then diffract the P-component of the circularly polarized wave guided light towards the eye, the remaining P-polarized light being collected in a light trap. The P-polarized light reflected back from the eye (which will be substantially P-polarized) is then diffracted into a return TIR path by the active SBG column and proceeds to the detector module as described above. This scheme ensures that image and illumination light is not inadvertently coupled into the input and output gratings respectively. In other embodiments of the invention the unwanted coupling of the image and illumination light may be overcome by optimizing the TIR angles, the angular bandwidths of the imaging and illumination gratings, the spacings along the waveguide of the input and output gratings, and the illumination and imaging beam cross sections. In one embodiment the illumination light which will typically in most embodiments of the invention be collimated may be angled such that the waveguide propagation angle of the illumination beam differs from the waveguide angles of the image light.

An important feature of the invention is that elements of the illumination sampling grating are switched to allow illumination to be localized to a small region within the active column of the DigiLens ensuring that the illumination is concentrated exactly where it is needed. This also avoids stray light reflections a problem which can consume significant image processing resources in conventional eye tracker designs. Since the illumination is scrolled the cornea and retina are not exposed to continuous IR exposure allowing higher exposures levels to be used leading to higher SNR. A safety interlock which is not illustrated may be included to switch off the laser when no tracking activity has been detected for a predefined time.

The proposed scheme for switching the columns and readout elements in the embodiments of FIGS. 25-27 is based on tracking the movement of the pupil using a X,Y localization algorithm similar to the one illustrated in FIG. 24 which shows how the ith activated column of DigiLens and jth activated element of the readout array are used to select the speckle pattern region (X,Y).

Figure 28:
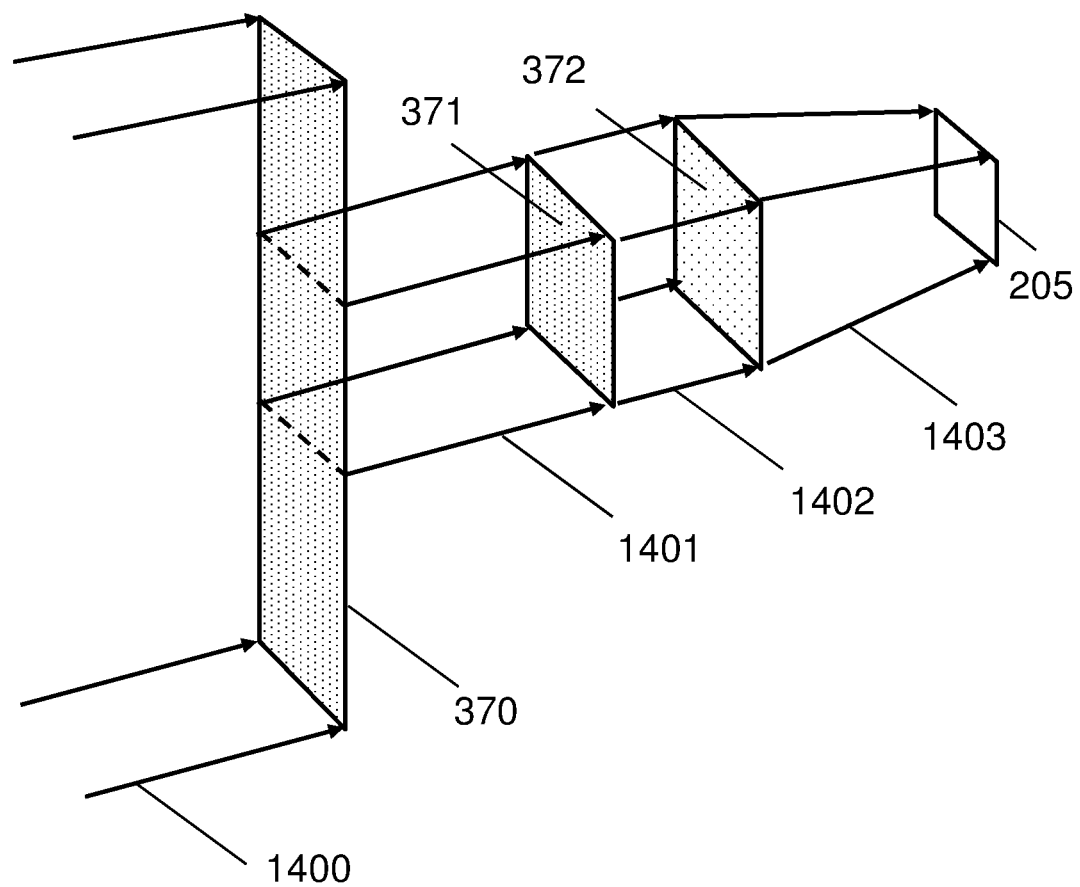
FIG. 28 is a simplified representation of the imaging process an eye tracker using common illumination and imaging gratings in one embodiment of the invention.

FIG. 28 is a simplified representation of the detection path starting with the collimated rays 1400 from an active column element 370 of the imaging array. The rays 1400 are sampled by an element 371 of the detector grating to provide the rays 1402 which are imaged by the holographic lens 372 to provide the rays 1403 incident on the detector 205.

Figure 29:
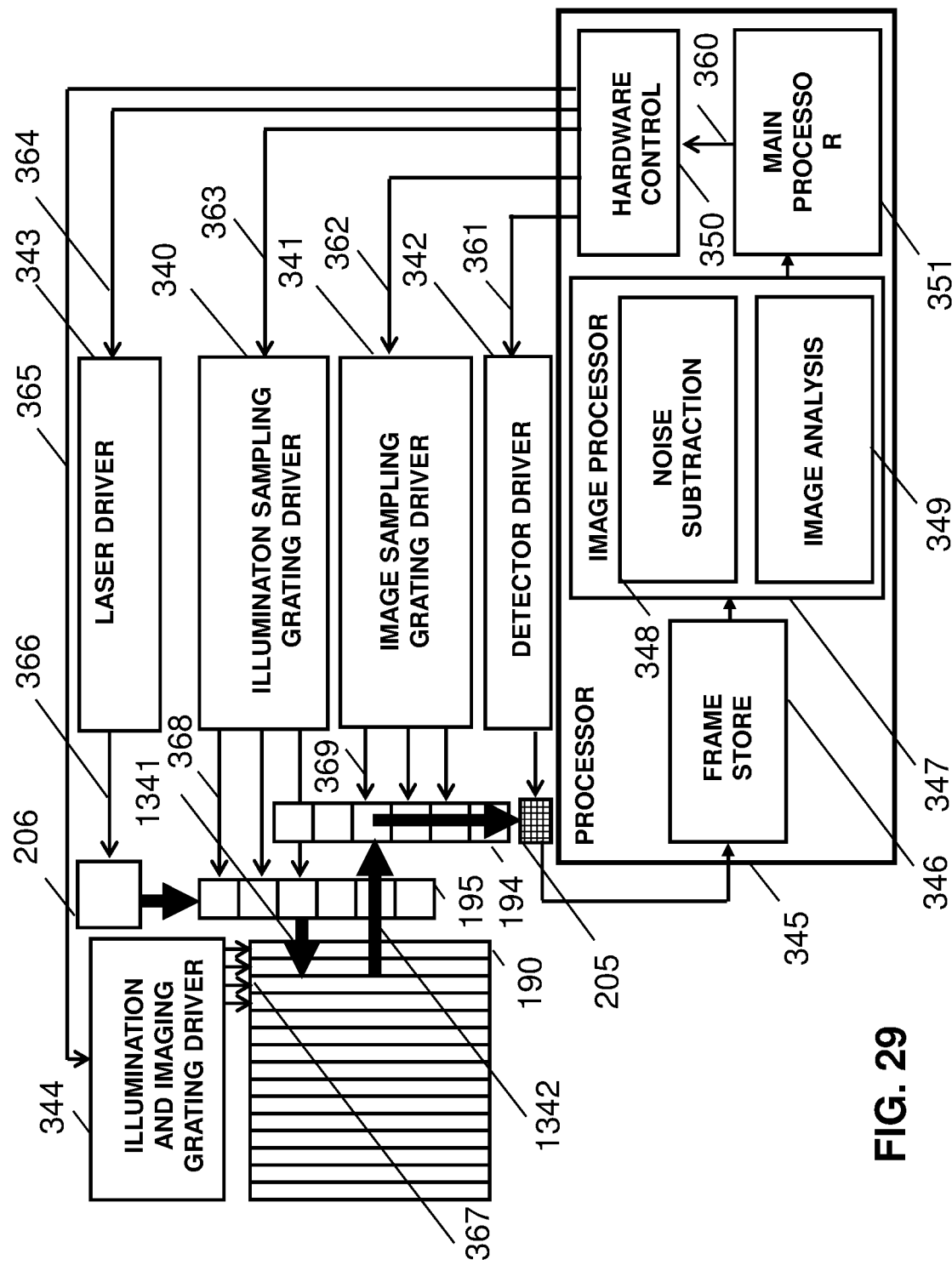
FIG. 29 provides a system block diagram showing the key modules of an eye tracker using common illumination and imaging gratings in one embodiment of the invention.

FIG. 29 provides a system block diagram of the eye tracker of FIGS. 26-27. The system modules comprise the illumination and imaging grating 190, image sampling grating 194, illumination sampling grating 195, detector 205, laser 206, illumination sampling array driver 340, image sampling array driver 341, detector driver 342, laser driver 343, illumination and imaging grating driver 344 and processor 345. The processor 345 comprises a frame store or other image storage media 346 for the storage of captured eye image or speckle pattern frames and an image processor 347 further comprising hardware or software modules for noise subtraction 348 and image analysis 349. The processor further comprises hardware control module 350 for controlling the illumination, imaging and image sampling grating drivers, all said modules operating under the control of a main processor 351. The above described modules are connected by communication and control links schematically indicated by 360-369 include control lines for switching the SBG elements in the imaging grating, illumination sampling grating array, and image sampling grating 367-369.

In one embodiment of the invention the detector array is a detector array of resolution 16×16 with a framing rate of 2300 fps of the type commonly used in infrared mouse equipment. In alternative embodies similar sensor technology of resolution 64×64 operating at 670 fps may be used. The selection of a particular sensor will depend on factors such as the required tracking resolution and accuracy and the update rate of the eye tracker. Exemplary sensors are manufactured by Pixart Inc. The detector optical prescription will be determined by a detailed ray-tracing analysis and will require trade-offs of speckle size, F-number and DigiLens column width. In the case of speckle tracking the detector lens aperture defines the limiting speckle size. The detector field of view is determined by the detector size and the detector lens focal length. However, the invention could be applied with any currently available imaging sensor technology. In one embodiment the DigiLens provides 25 SBG scrolling columns×17 SBG readout elements. The Agilent device can be programmed to switch 2300 fps So a complete scan of the FOV will take (25×17)/2300 s.=185 ms. However, in practice the eye tracker will use a more sophisticated X-Y search process that localizes the pupil using column and readout element coordinates. It is anticipated that on average around 10 search steps may be needed to converge on the pupil position resulting in a latency of 4.3 ms. On this basis the latency of the tracker is potentially ×100 lower than that of comparable image processing-based Purkinje-type eye trackers. It is also anticipated that the correlation process will be implemented in hardware resulting in a relatively modest data processing latency. The detected eye signature is stored and compared with other saved patterns to determine the eye gaze trajectory and to make absolute determinations of the gaze direction (bore sighting). Initial calibration (that is, building up the database of saved patterns) is carried out by directing the user to look at test targets at predefined points in the field of view (FOV) over which the eye gaze is to be tracked. Since the frames are of low resolution large numbers of samples may be collected without significant computational overhead.

Although the invention may be used to detect any type of eye signature, speckle is attractive because it avoids the image analysis problems of identifying and tracking recognizable features of the eye that are encountered in Purkinje imaging schemes. Prerequisites for measuring eye displacement vectors (rotational and/or translational) include achieving an adequate level of speckle contrast (after detector noise and ambient light have been subtracted from the detected signal) and being able to resolve individual speckle grains. A high signal to noise ratio (SNR) is essential for detecting variations in speckle properties at required angular resolution. The SNR depends on the speckle contrast, which is defined as the ratio of the root means square (rms) variation of the speckle intensity to the mean intensity. The speckle contrast lies between 0-1 assuming Gaussian statistics. The detector should have low noise and a short integration time. If the motion of the eye is appreciably faster than the exposure time of the CCD camera rapid intensity fluctuations of the speckle pattern will occur, the average of the detected patterns resulting in a blurred image with reduced speckle contrast. The smallest speckle size is set by the diffraction limit. Applying the well-known formula from diffraction theory: w=~2.44D/a (assuming: a detector lens to detector distance D~70 mm.; IR wavelength l=785 nm.; and detector lens aperture a~3 mm) we obtain a diffraction limited speckle diameter w at the detector of ~64 microns. The resolution of a typical mouse sensor is around 400-800 counts per inch (cpi), with rates of motion up to 14 inches per second (fps). Hence the limiting speckle size is equivalent to one count per 64 micron at 400cpi which is roughly compatible with the expected speckle size.

The proposed strategy for processing speckle data captured by the eye tracker is based on the following assumptions.

Speckle patterns provide unique "fingerprints" of regions of the cornea and retina.

Unlike speckle interferometry which requires that the speckle motion is less than speckle size, speckle imaging using a detector array requires that the speckle displacement from frame to frame is greater than the speckle size A displacement of the cornea and retina relative to the detector will result in a shift of the speckle pattern by the same amount The shifts of the corneal and retinal speckle patterns will be in opposite directions.

The motion of the speckles can be determined from the correlation of two consecutive frame speckle patterns. This information together with the relative motion of the corneal and retinal speckle patterns can be used to determine eye displacement vectors.

The correlation and image analysis processes may take advantage standard techniques already developed in applications such as radar, biological imaging etc.

The speckle contrast and speckle size at the detector are compatible with the detector resolution and SNR.

The following characteristics of the speckle image may also be used to assist the tracking of the eye use speckle: speckle grain size; speckle brightness (either individual or collective brightness); speckle shape; rate of change of any of the preceding characteristics with ocular movement; and relative directions of corneal and retinal bema displacements. It is further recognized that each of these aspects of the speckle image will be dependent on the illumination beam direction (scanning or static); the detection optics and the focal length of the imaging optics. The rate of change of the corneal versus retinal speckles will depend on the focal length.

Figure 30:
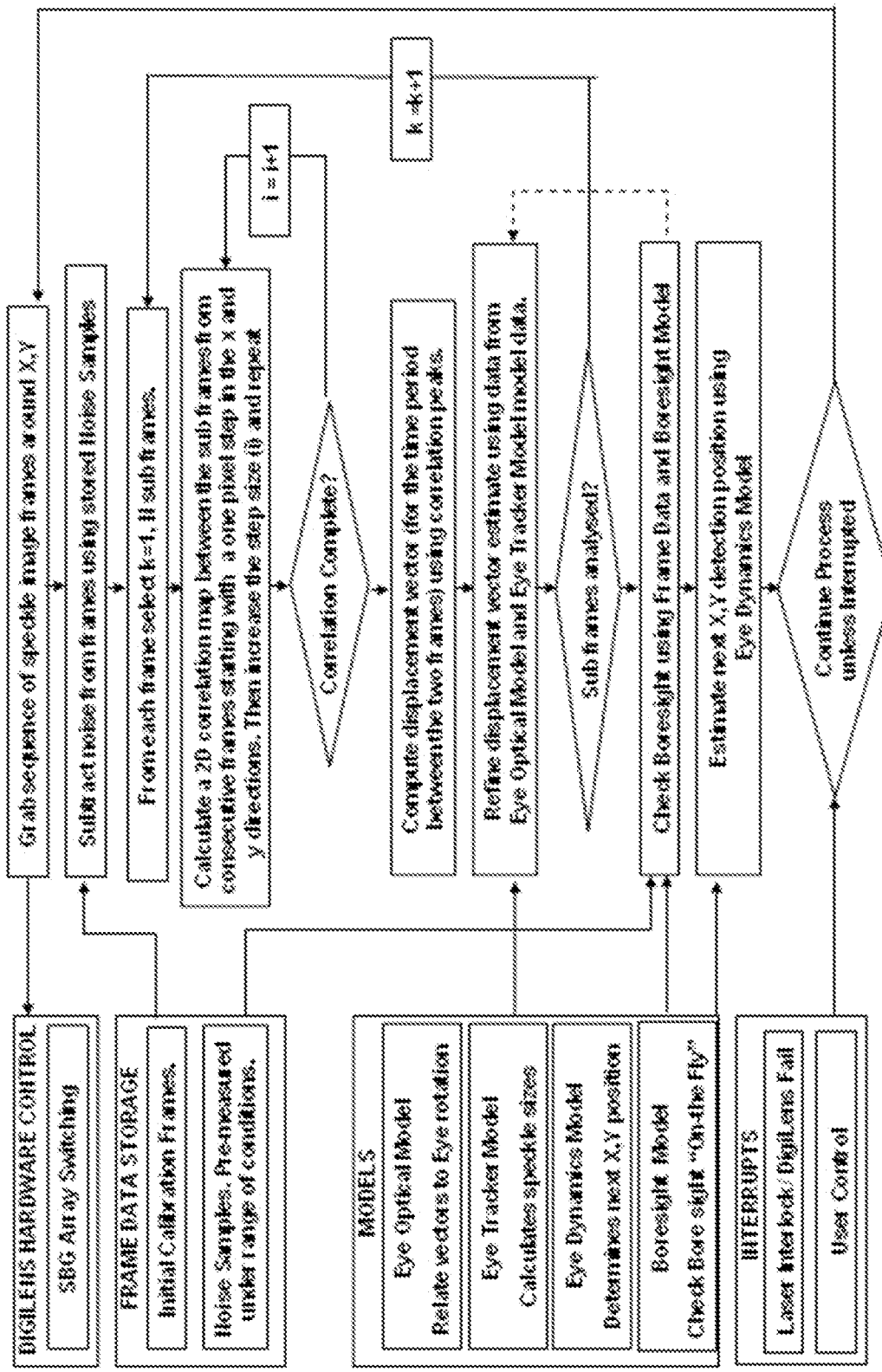
FIG. 30 is a flow chart showing the process for determining eye displacement vectors from the recorded speckle data.

The flow chart in FIG. 30 summarizes the process for determining eye displacement vectors from the recorded speckle data. The process relies on a database of frame data collected during initial calibration and noise characteristics. The calculation of the displacement vectors uses inputs from a suite of mathematical models that simulate the first order eye optics, the eye tracker optics and the eye dynamics. The process may be interrupted by the user or automatically when a DigiLens failure occurs. The process also includes DigiLens hardware control to enable X,Y addressing of DigiLens columns and readout elements. The correlation process for obtaining the eye displacement vector from two detected frames in one embodiment may be summarized as follows. Each frame is subdivided into small sub frames. The sub-frame coordinates may be predefined or alternatively may be determined by an interactive scheme using the output from an Eye Dynamics Model. A 2D correlation map between the sub images from the two frames is calculated starting with a one pixel step in the x and y directions and repeat the calculation increasing the step size by one pixel at a time. Other statistical metrics may also be computed at this stage to assist in refining the calculation. We then repeat the correlation process for another selected frame region. A displacement vector is then computed using (for the time period between the two analyzed frames) using the peaks of the correlation maps. Ideally the sub frames should be entirely within the corneal or retinal fields, the two being distinguished by their opposing directions. Data which does not yield clear separation of the two will be rejected) at this stage. The calculation is refined using data from an Eye Optical Model which models of the eye dynamics and an Eye Tracker Model which models the optical system. The verified displacement vector is used to determine the next search X,Y coordinates (ie SBG column, row) for the Eye Tracker using predicted gaze trajectory calculated using an Eye Dynamics Model. The basic ray optics used in the Eye Model in particular the relationship of the first order corneal and retinal reflection paths of the eye may be modelled using ray-tracing programs such as ZEMAX. Standard eye models well known to those skilled in the art will be adequate for this purpose. Further models may be used to simulate speckle from the retina and the cornea. The Eye Dynamics Model carries out a statistical analysis of the displacement vectors from previous frames to determine the most optical next X,Y search location (ie the columns and readout elements to be activated in the DigiLens.

Figure 31A:
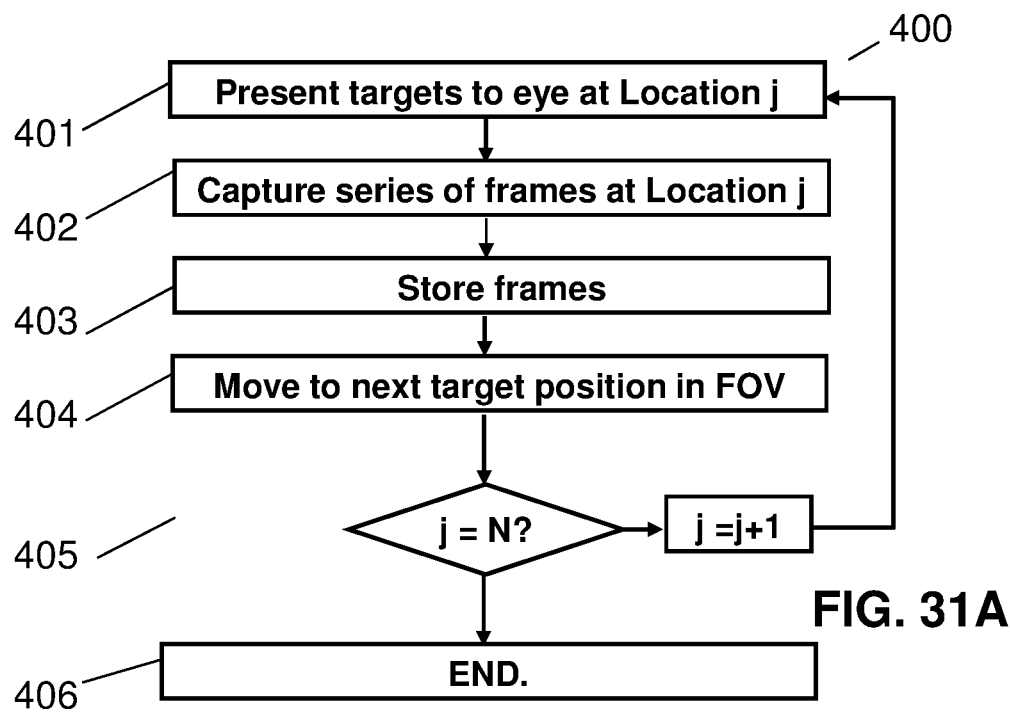
FIG. 31A is a flowchart for a calibration process for an eye tracker using common illumination and imaging gratings in one embodiment of the invention.
Figure 32:
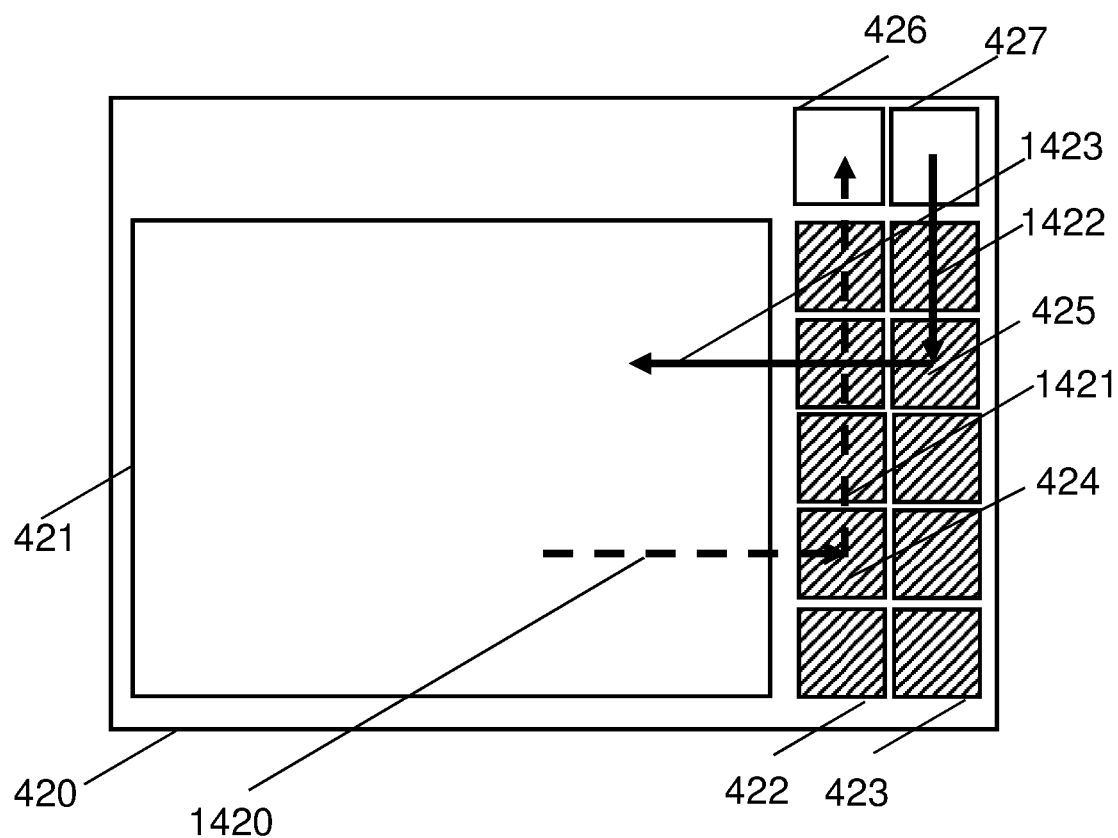
FIG. 32 is a schematic plan view of an eye tracker including an illumination sampling grating and an image sampling grating each based on gratings with grating vectors substantially aligned parallel to the waveguide plane in one embodiment of the invention.

Initial calibration is carried out by directing the user to look at test targets at predefined points in the FOV. The bore-sighting process is illustrated in FIG. 32 which shows a flowchart (FIG. 32A) and a schematic illustrates of the initial calibration procedure (FIG. 32B). According to FIG. 31A the bore sighting procedure 400 comprises the following steps:

At step 401 present targets to the eye at location j;
At step 402 capture a series of frames at location j;
At step 403 store the capture frames;
At step 404 move to the next target position in the field of view (FOV);
At step 405 repeat the process while j is less than a predefined integer N; otherwise end the process (at step 406).

Figure 31B:
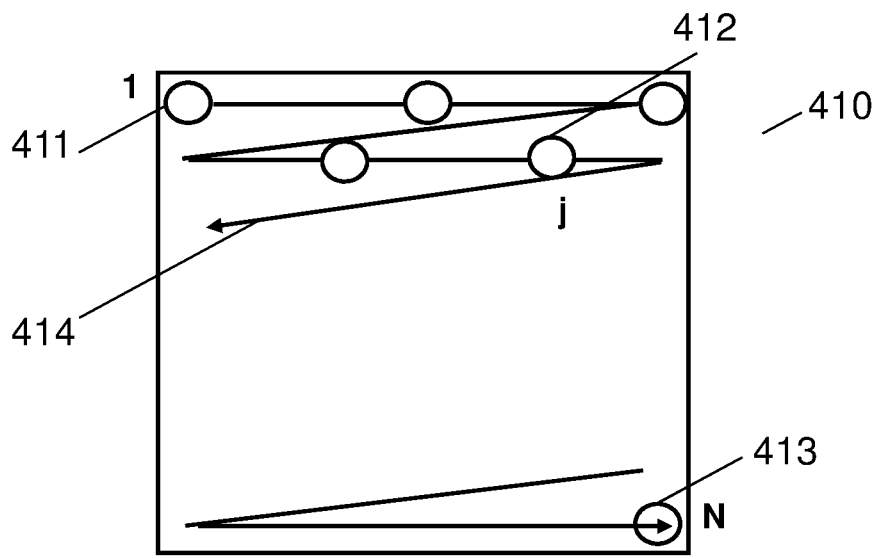
FIG. 31B is a schematic illustration of the initial calibration procedure used for an eye tracker in one embodiment of the invention.

Referring to FIG. 31B we see that initial calibration will be carried by presenting targets (typically lights sources, resolution targets etc.) to the viewer at different points $1 \leq j \leq N$ in the field of view 410 (the point also being labelled as 411-413) and capturing and storing frames of signature images at each location. The targets may be presented sequentially along the sweep path labelled by 414. However, other presentation schemes may be used. The stored frames will be processed to enhance SNR and extract statistical metrics (such as histograms, probability density functions for speckle size etc.) for subsequent "on-the-fly" frame comparison. Each frame provides a "fingerprint" for the region of the FOV concerned. The signatures will vary in: relative positions of the corneal and retinal reflections, or where speckle patterns are used: speckle contrast; and speckle size distribution (which is linked to optical magnification).

In relation to the embodiment of FIG. 25 we have described the use of an image sampling grating overlaying the output grating. The image sampling grating comprises a linear array of switchable grating elements, each element when in its diffracting state sampling a portion of the light in the waveguide and deflecting it along the image sampling grating towards said detector. In a similar fashion an illumination sampling grating overlays the input grating. The illumination sampling grating is optically coupled to the light source and comprises a linear array of switchable grating elements. Each element when in its diffracting state deflects light from the illumination sampling grating into the waveguide. Turning to FIG. 32 we next consider an embodiment that implements image and illuminations sampling grating using a single grating layer. The eye tracker 420 comprises a DigiLens 420, image sampling gating 422 illumination sampling grating 423 containing elements such as 424 and 425 respectively. Output and input gratings 426,427 link the sampling gratings to the detector and light sources respectively. As indicated by the shading pattern of the grating elements each element comprising a switchable grating with Bragg fringes slanted at 45 degrees with grating vectors in the plane of the drawing; that is, in a plane parallel to the waveguiding surfaces. The inventors refer to these gratings as turning gratings. Hence illumination ray 1422 undergoing TIR in the DigiLens is deflected through an angle of ninety degrees by the active element 425 into the ray direction 1423. Similarly the image ray 1420 is deflected through an angle of ninety degrees in the direction 1421 by the active element 424. It should also be apparent from consideration of the drawing that all of the gratings may be formed in a single layer in a single waveguide (with the appropriate electrode patterning of the sandwiching substrates. It should also be apparent that the turning grating principle may be applied in any of the above described embodiments including those in which the DigiLens comprises separated overlapping illumination and imaging gratings. The sampling gratings may overlap. The design of the turning gratings may be based on the teachings of U.S. Pat. No. 8,233,204 entitled OPTICAL DISPLAYS which is incorporated herein by reference in its entirety.

Figure 33A:
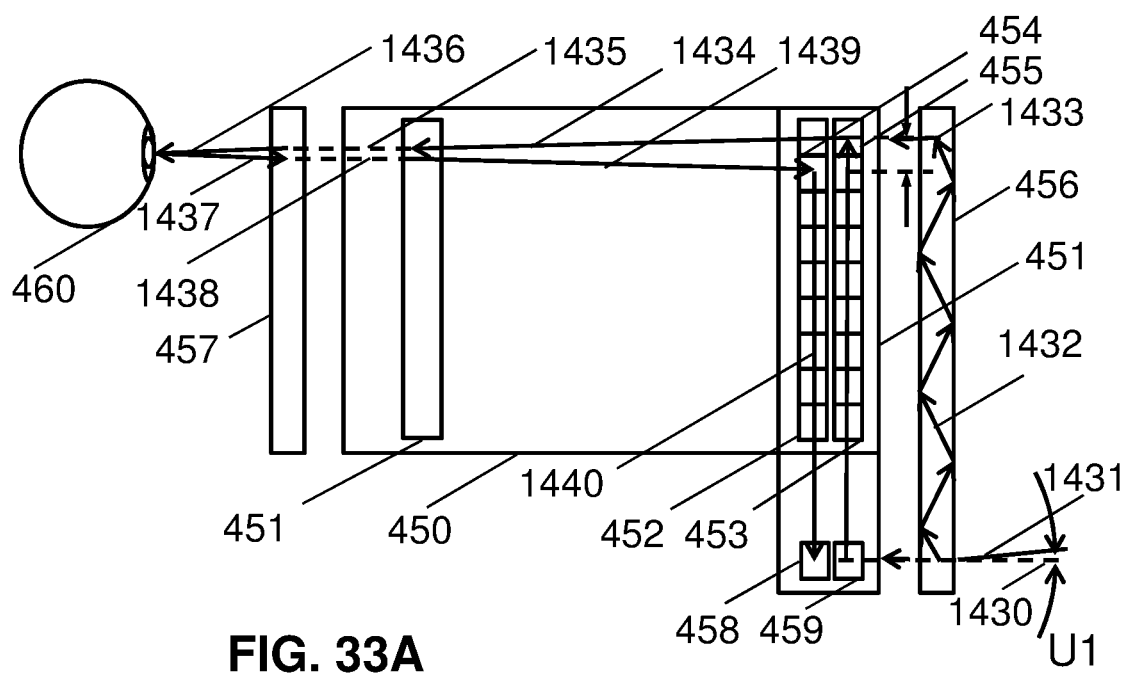
FIG. 33A is a schematic plan view illustrating a first aspect of an eye tracker including an illumination sampling grating and an image sampling grating in which the illumination light is angularly offset from the image light.
Figure 33B:
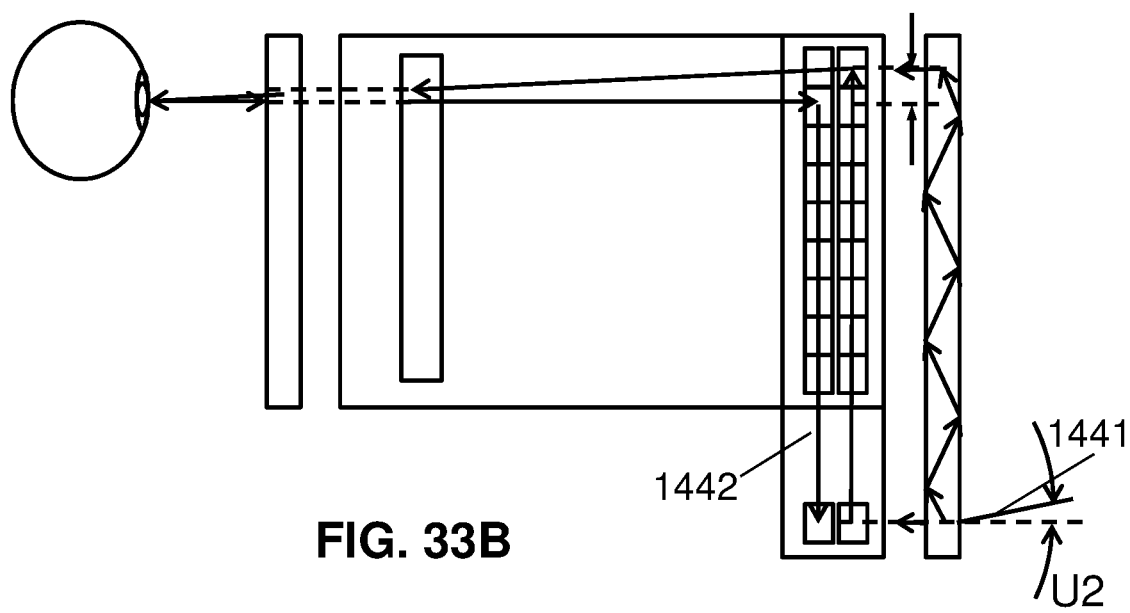
FIG. 33B is a schematic plan view illustrating a second aspect of an eye tracker including an illumination sampling grating and an image sampling grating in which the illumination light is angularly offset from the image light.

A challenge in a single layer eye tracker design of the type described above is to provide adequate eye illumination without compromising the ability of the DigiLens to collected scattered light from the eye. Most attempts to use gratings for light management in bi-directional waveguides fail because of the fundamental principle of grating reciprocity. In practical terms this means that some of the image light almost always ends up getting coupled into the illumination path to the source by the input grating. In the reciprocal process some of the illumination light is diffracted into the imaging path to the detector by the output grating. The amount of this cross coupling will depend on the beam divergence and waveguide dimensions. The proposed solution which is illustrated in FIG. 33 assumes the common illumination and imaging waveguide architecture discussed above and, in particular, the one illustrated in FIG. 25. The apparatus comprises the DigiLens 450 which comprises an array of SBG columns such as 451 and a waveguide component 451 comprising the illumination sampling and imaging sampling gratings 452,453 and containing grating elements (which we may refer to as pixels) such as 454,455. A cross section of the illumination sampling grating is provided by 456. The cross section of the DigiLens is also shown and is indicated by 458. Gratings for coupling the image and illumination light to the detector and laser are indicated by 458,459. Finally, an eye is represented by 460. The input and output gratings, which will typically overlap the sampling gratings as discussed earlier, are not illustrated. We next consider the ray paths, first defining a normal to the illumination waveguide as indicated by 1430. The path of an incident beam at an angle U1 up the eye is indicated by the rays 1431-1436 comprising the TIR path 1432, coupling into the DigiLens via the active element 455 as indicated by the ray 1433, propagating up to the active column element 451 as indicated by ray 1434, diffraction towards the eye along 1435, and light 1436 striking a surface of the eye. The reflection light path from the eye to the detector is indicated by the rays 1437-1440 with scattered light from the eye indicated by 1437 entering the DigiLens as 1438 and propagating along the path 1439 before being diffracted into the image sampling grating via the element 454 and proceeding along the path 1440 leading the detector. FIG. 33B shows the corresponding ray paths 1441,1442 for an incident ray 1441 launched at the angle U2 (greater than U1) which terminates at the detector, the ray paths following the logic of FIG. 33A. In one embodiment of the invention the method illustrated in FIG. 33 eliminates unwanted light coupling by applying a small tilt to the input beam angle by an amount equivalent to at least 1 pixel of the eye tracker imaging matrix, for a specular beam. In other embodiments larger pixel offsets may be useful for better discrimination. A similar tilt is required in the case of diffuse beams. Gratings are currently the preferred option for producing the tilt. However, alternative methods based on prisms may be used. In one embodiment the method illustrated in FIG. 33 is used to provide different grating tilts for the upper and lower halves of the waveguide, thereby preventing over sizing of the lower portion of the waveguide.

Figure 34:
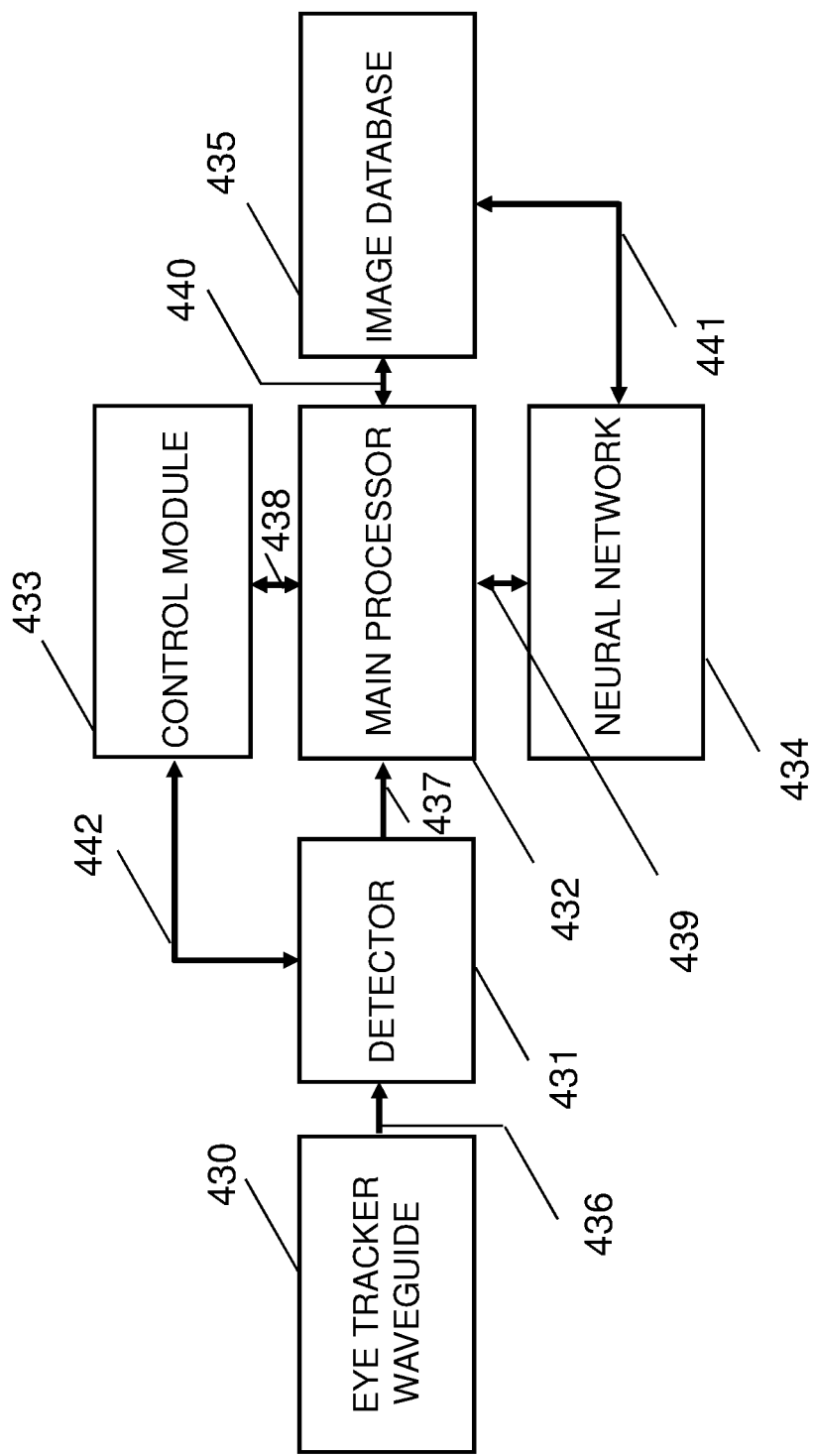
FIG. 34 is a block diagram showing the principal modules of an eye tracker system including a neural network in one embodiment of the invention.
Figure 35:
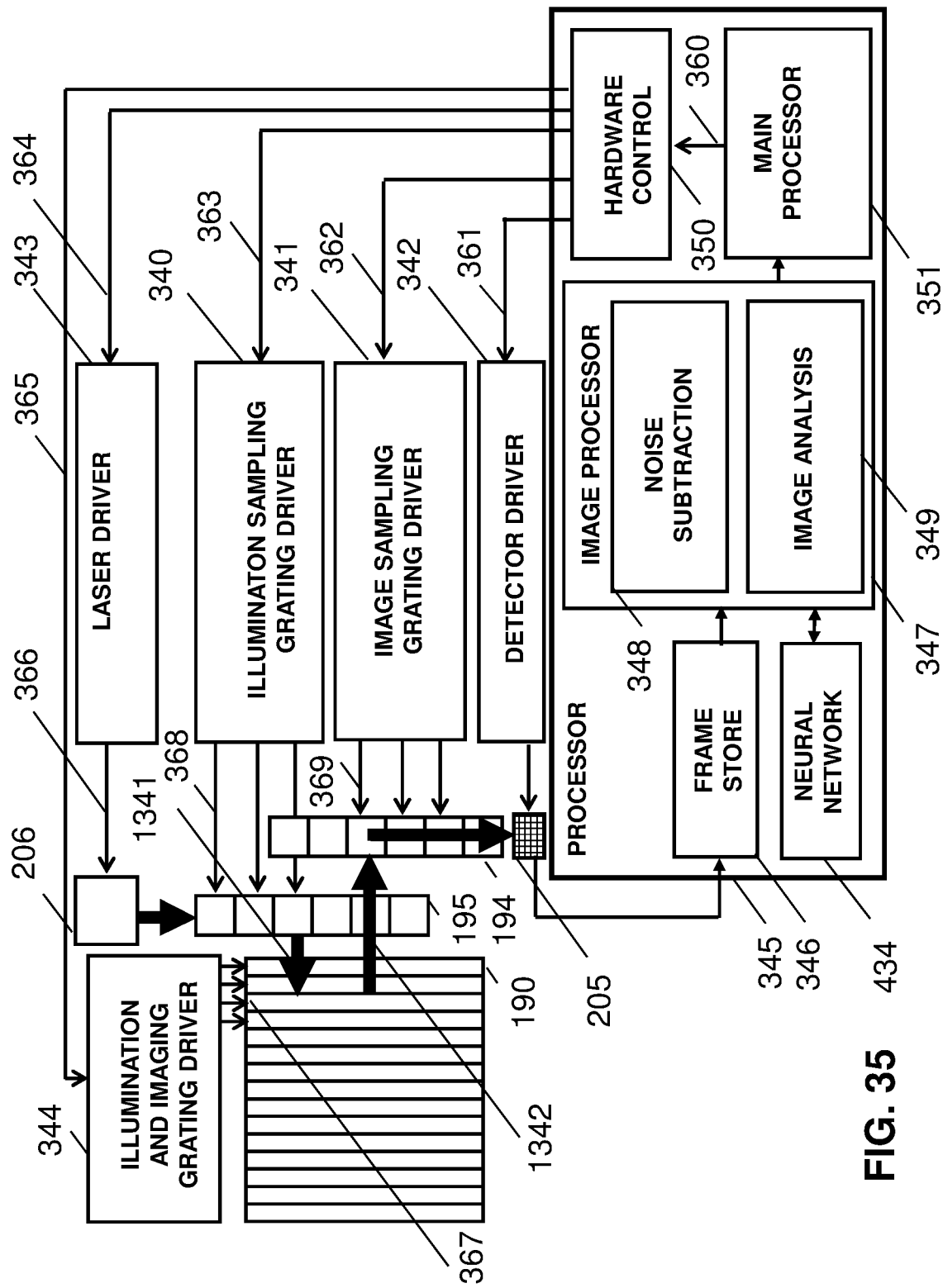
FIG. 35 is a block diagram showing the principal modules of an eye tracker system based common illumination and imaging grating in which the processing system includes a neural network in one embodiment of the invention.

In the description of the eye tracker data processing architecture we have discussed how initial calibration will be carried by presenting targets (typically lights sources, resolution targets etc.) to the viewer at different points in the field of view and capturing and storing frames of speckle pattern images at each location. These images are used aid the processing of live data when the eye tracker is normal use. It is proposed that the process could be aided by incorporating an artificial neural network within the processor. The bore sighting process would correspond to training the networks. The network could be used to compensate at least part of any systematic measurements errors occurring in the processing. In one embodiment of the invention shown in the block diagram of FIG. 34 the eye tracker system comprises the eye tracker waveguide 430, detector 431, processor comprising: main processor 432, waveguide SBG control module 433, neural network 434 and image database 435. The system modules are connected by communication and control links referenced by numerals 436-442. A more detailed architecture incorporating a neural network is shown in FIG. 35 This is architecture is intended for use with a common illumination and imaging grating eye tracker designs such as the one of FIG. 25.

Although the description of the invention has emphasized the detection of speckle patterns it should be apparent from consideration of the description and drawings that the same optical architecture and indeed many features of the processing architecture may be used to perform eye tracking using other optical signatures from the eye. For example features such as bright or dark pupils and glint may provide suitable signatures. The blurring of the eye feature being tracked does not present an impediment providing that the detected image contains enough content for correlations to be made between captured frames and stored images capture in the bore sighting (or neural network training) stage.

The optical design requires careful balancing of the high source flux needed to overcome throughput inefficiencies arising from the small collection angles, low transmission thorough the DigiLens and the low reflectivity of the eye (~2.5% at the surface of the cornea) with the requirement for eye-safe IR illumination levels. Typically, for applications in which the eye tracker is used for hours at a time under continuous IR exposure the eye irradiance should not exceed around 1 mW/cm2. The appropriate standards for eye safe infrared irradiance are well known to those skilled in the art. Since the proposed eye tracker scrolls the illumination across the eye the cornea and retina are not exposed to continuous IR exposure allowing higher exposures levels to be used leading to higher speckle contrast level and therefore higher SNR at the detector. In a switchable grating based design there is the risk of a switching malfunction causing the laser beam scanning to freeze resulting in all of the available output laser power being concentrated into a small area of the eye. To overcome this problem a safety interlock may be provided to switch off the laser when no tracking activity has been detected for a predefined time of, typically, a few minutes. During this dead time the IR exposure may be allowed to increase significantly without exceeding the safety threshold.

The proposed eye tracker avoids the cost and complexity of implementing classical Purkinje imaging methods by tracking eye signatures using low resolution high speed image sensors. The signatures do not need to be images of eye features such as pupil edges but can be random structures such as speckle patterns. However, it is important that whatever signature is tracked has a strong spatio-temporal variation with gaze direction. Conventional iris image capture systems are an indicator the level of processing that will be required in an eye tracker. The iris image is typically acquired by a camera using infrared light in the 700 nm-900 nm band resolving in the region of 100-200 pixels along the iris diameter. The first step is usually to detect and remove stray light before proceeding to determine the boundaries of the iris. Typically the centers and radii of iris and pupil are approximated initially by applying a circular edge detector. High accuracy and rapid response times require high-performance and high-cost microprocessors that are beyond the scope of consumer products. Traditional image processing designs based on software are too slow. It is known that significant improvements may result from an iris recognition algorithms based on a hardware-software co-design using low-cost FPGAs. The system architecture consists of a 32-bit general purpose microprocessor and several dedicated hardware units. The microprocessor executes in software the less computationally intensive tasks, whereas the coprocessors speed-up the functions that have higher computational cost. Typically, depending on the function implemented, coprocessors speed-up the processing time by a factor greater than 10 compared to its software execution. However, the best latency achieved with hardware-software co-designs, is typically in the range 500-1000 ms. It should be noted that an eye tracker is a much more demanding proposition for an image processor. Detecting a clean iris image is only the first step. Applying the edge detection algorithms as the eye moves around the eye box will require several frames to be analyzed adding to the overall latency.

The proposed eye tracker is compatible with many display applications in consumer products, avionics and other fields such as Augmented Reality by enabling the features of: wide field of view; large exit pupil; thin form factor; low inertia; and easy integration with near-eye display technologies.

It should be emphasized that the drawings are exemplary and that the dimensions have been exaggerated. For example thicknesses of the SBG layers have been greatly exaggerated.

In any of the above embodiments the waveguides may be curved or formed from a mosaic of planar or curved facets.

An eye tracker based on any of the above-described embodiments may be implemented using plastic substrates using the materials and processes disclosed in PCT Application No.: PCT/GB2012/000680, entitled IMPROVEMENTS TO HOLOGRAPHIC POLYMER DISPERSED LIQUID CRYSTAL MATERIALS AND DEVICES.

Advantageously, the SBGs are recorded in a reverse mode HPDLC material in which the diffracting state of SBG occurs when an electric field is applied across the electrodes. An eye tracker based on any of the above-described embodiments may be implemented using reverse mode materials and processes disclosed in PCT Application No.: PCT/GB2012/000680, entitled IMPROVEMENTS TO HOLOGRAPHIC POLYMER DISPERSED LIQUID CRYSTAL MATERIALS AND DEVICES.

While the invention may be applied with gratings of any type including switching or non-switching gratings based on Bragg (volume) holograms, or surface-relief gratings the preferred grating technology is a SBG, which offers the advantages of fast switching, high optical efficiency and transparency and high index modulation.

With regard to the use of grating arrays it should be appreciated the number of elements used in an array need not be very large, depending on the FOV over which gaze is to be tracked.

It should also be noted that the gratings used in the eye tracker are not necessarily all switching gratings. Switching gratings may be used in combination with passive grating technologies. As has been indicated by the description and drawings more than one grating layer (lamina) may be used. The grating layers discussed above are SBGs disposed between internal waveguide surfaces (or in other words sandwiched between transparent substrates that combine to form the waveguide. However in equivalent embodiments some of the gratings layers could be applied to external waveguide surfaces. This would apply in the case of surface relief gratings.

A glass waveguide in air will propagate light by total internal reflection if the internal incidence angle is greater than about 42 degrees. Thus the invention may be implemented using transmission gratings if the internal incidence angles are in the range of 42 to about 70 degrees, in which case the light extracted from the light guide by the gratings will be predominantly p-polarized.

Using sufficiently thin substrates the eye tracker could be implemented as a long clear strip appliqué running from the nasal to ear ends of a HMD with a small illumination module continuing laser dies, light guides and display drive chip tucked into the sidewall of the eyeglass. A standard index matched glue would be used to fix the display to the surfaces of the HMD.

The method of fabricating the SBG pixel elements and the ITO electrodes used in any of the above-described embodiments of the invention may be based on the process disclosed in the PCT Application No. US2006/043938, entitled METHOD AND APPARATUS FOR PROVIDING A TRANSPARENT DISPLAY.

The invention does not rely on any particular methods for introducing light from a laser source into the eye tracker and directing light scattered from the eye onto a detector. In the preferred embodiments of the invention gratings are used to perform the above functions. The gratings may be non switchable gratings. The gratings may be holographic optical elements. The gratings may be switchable gratings. Alternatively, prismatic elements may be used. The invention does not rely on any particular method for coupling light into the display.

It should be understood by those skilled in the art that while the present invention has been described with reference to exemplary embodiments, it is to be understood that the invention is not limited to the disclosed exemplary embodiments. Various modifications, combinations, sub-combinations and alterations may occur depending on design requirements and other factors insofar as they are within the scope of the appended claims or the equivalents thereof.

What is claimed is:

1. An apparatus for tracking the movement of an eye, comprising:
   a first waveguide;
   a light source for illuminating said eye;
   at least one detector optically coupled to said waveguide;
   disposed within said waveguide, at least one grating layer comprising at least one grating elements with a grating prescription for diffracting light reflected from said eye into a total internal reflection (TIR) path to said detector; and
   a processor configured to receive signals output from said detector,
   wherein said detector is configured to record a first optical signature resulting from a first gaze direction and to record a second optical signature resulting from a second gaze direction, and wherein said processor is configured to determine changes in gaze direction by correlating said first optical signature and said second optical signature.

2. The apparatus of claim 1, wherein each of said first optical signature and said second optical signature results from at least one of reflection or scatter from at least one of an optical surface or an ocular medium of said eye.

3. The apparatus of claim 1, wherein each of said first optical signature and said second optical signature is characterized by at least one of signature feature spatial size or signature feature spatial distribution.

4. The apparatus of claim 3, wherein each of said first optical signature and said second optical signature is further characterized by at least one of speckle or glint.

5. The apparatus of claim 1, wherein said first waveguide contains a grating or prism for coupling illumination from said source into an illumination TIR path in said first waveguide and a grating for coupling light out of said illumination TIR path onto said eye.

6. The apparatus of claim 1, further comprising a second waveguide supporting a grating or prism for coupling illumination from said source into an illumination TIR path in said second waveguide and a grating for coupling light out of said illumination TIR path onto said eye.

7. The apparatus of claim 1, wherein at least one of said first plurality of grating elements or said second plurality of grating elements comprises at least one switchable grating element having a diffracting state and a non-diffracting state.

8. The apparatus of claim 1, wherein at least one of said first plurality of grating elements or said second plurality of grating elements comprises at least one switchable grating element having a diffracting state and a non-diffracting state, wherein said element in said diffracting state deflects light reflected from said eye into at least one of said first or second TIR paths.

9. The apparatus of claim 1, wherein at least one of said first plurality of grating elements or said second plurality of grating elements comprises an array of elongate elements.

10. The apparatus of claim 1, wherein at least one of said first plurality of grating elements or said second plurality of grating elements is a two-dimensional array.

11. The apparatus of claim 1, wherein saki grating layer comprises at least one of a switchable Bragg grating, a switchable grating recorded in a reverse mode holographic polymer dispersed liquid crystal, a switchable grating recorded in a reverse mode holographic polymer dispersed liquid crystal, a surface relief grating or a non-switching Bragg grating.

12. The apparatus of claim 1, wherein said eye surface is at least one of a cornea, front or rear lens surface, iris, sclera or retina.

13. The apparatus of claim 1, wherein said detector is a two-dimensional array.

14. The apparatus of claim 1, further comprising at least one grating with at least one of optical power or diffusing properties.

15. The apparatus of claim 1, wherein said detector is connected to at least one of an image processing apparatus for determining at least one spatio-temporal characteristic of an eye movement or an image processing system including a neural network.

16. The apparatus of claim 1, wherein said detector is coupled to said waveguide by a grating or a prism.

17. The apparatus of claim 1, integrated within a HMD or HUD.

18. The apparatus of claim 1, further comprising a turning grating.

19. The apparatus of claim 1, wherein said source is a laser or a light emitting diode.

20. The apparatus of claim 1, wherein the processor is configured to determine changes in the gaze direction using the relative displacements of a detected optical signature resulting from light being scattered from the retina and a detected optical signature resulting from light being scattered from the cornea.

* * * * *